United States Patent
Stockmaster et al.

(10) Patent No.: US 10,478,371 B2
(45) Date of Patent: Nov. 19, 2019

(54) MEDICAL REHAB BODY WEIGHT SUPPORT SYSTEM AND METHOD WITH HORIZONTAL AND VERTICAL FORCE SENSING AND MOTION CONTROL

(71) Applicant: Gorbel, Inc., Fishers, NY (US)

(72) Inventors: James G. Stockmaster, Sodus, NY (US); Brian G. Peets, Fairport, NY (US); Benjamin A. Strohman, Henrietta, NY (US); Alexander Z. Chernyak, Pittsford, NY (US); Blake Reese, Honeoye Falls, NY (US); Dean C. Wright, Fairport, NY (US); Yi Luo, Rochester Hills, MI (US); Li-Te Liu, Taiwan (TW); Betty Dolce, Rochester, NY (US); Thomas R. Fischer, Williamsville, NY (US); Chris Bierl, East Aurora, NY (US); Judy Powers, Orchard Park, NY (US); Don Sacilowski, Lancaster, NY (US)

(73) Assignee: Gorbel, Inc., Fishers, NY (US)

( * ) Notice: Subject to any disclaimer, the term of this patent is extended or adjusted under 35 U.S.C. 154(b) by 0 days.

(21) Appl. No.: 15/014,679

(22) Filed: Feb. 3, 2016

(65) Prior Publication Data
US 2016/0256346 A1    Sep. 8, 2016

Related U.S. Application Data

(63) Continuation-in-part of application No. 14/160,613, filed on Jan. 22, 2014, now Pat. No. 9,510,991.
(Continued)

(51) Int. Cl.
*A61H 3/00*    (2006.01)
*G16H 40/63*    (2018.01)
(Continued)

(52) U.S. Cl.
CPC .......... *A61H 3/008* (2013.01); *A61B 5/1117* (2013.01); *G06F 19/3481* (2013.01);
(Continued)

(58) Field of Classification Search
CPC .......... A61H 3/008; A61H 2201/5061; A61H 2201/5038; A61H 2201/5092;
(Continued)

(56) References Cited

U.S. PATENT DOCUMENTS

| 1,961,119 A | 5/1934 | Ettinger |
| 2,590,739 A | 3/1952 | Hugo |

(Continued)

FOREIGN PATENT DOCUMENTS

| DE | 102013222371 A1 | 5/2015 |
| EP | 2402279 | 4/2012 |

(Continued)

OTHER PUBLICATIONS

PCT/US2014/012434 An Unofficial International Search Report and Written Opinion dated Jun. 18, 2014 for PCT/US2014/012434 filed Jan. 22, 2014, Inventor James G. Stockmaster, et al.
(Continued)

*Primary Examiner* — Sundhara M Ganesan
*Assistant Examiner* — Shila Jalalzadeh Abyaneh
(74) *Attorney, Agent, or Firm* — Duane C. Basch; Basch & Nickerson LLP

(57) ABSTRACT

A body-weight support system is disclosed, including an improved body weight support apparatus and method. The system enables not only the support of patients undergoing rehabilitation therapies, but exercise modes that are both customizable and dynamic in nature, including alternative functionality at differing locations.

21 Claims, 41 Drawing Sheets

Related U.S. Application Data

(60) Provisional application No. 62/182,410, filed on Jun. 19, 2015, provisional application No. 62/111,288, filed on Feb. 3, 2015, provisional application No. 61/755,007, filed on Jan. 22, 2013.

(51) Int. Cl.
   *A61B 5/11*   (2006.01)
   *G06F 19/00*   (2018.01)

(52) U.S. Cl.
   CPC ..... *G16H 40/63* (2018.01); *A61H 2201/0173* (2013.01); *A61H 2201/1215* (2013.01); *A61H 2201/1659* (2013.01); *A61H 2201/5007* (2013.01); *A61H 2201/5023* (2013.01); *A61H 2201/5035* (2013.01); *A61H 2201/5038* (2013.01); *A61H 2201/5043* (2013.01); *A61H 2201/5058* (2013.01); *A61H 2201/5061* (2013.01); *A61H 2201/5092* (2013.01); *A61H 2201/5097* (2013.01)

(58) Field of Classification Search
   CPC .... A61H 2201/1215; A61H 2201/5097; A61H 2201/5043; A61H 2201/5035; A61H 2201/1659; A61H 2201/0173; A61H 2201/5058; A61H 2201/5023; A61H 2201/5007; G06F 19/3481; G16H 40/63; A61B 5/1117
   USPC ............................... 482/1, 4, 6–8, 142, 143
   See application file for complete search history.

(56) References Cited

U.S. PATENT DOCUMENTS

| | | | |
|---|---|---|---|
| 3,222,029 A | 12/1965 | Hildemann | |
| 3,252,704 A | 5/1966 | Wilson | |
| 3,330,154 A | 7/1967 | Habern et al. | |
| 3,654,922 A | 4/1972 | Outcalt | |
| 3,699,809 A | 10/1972 | Komatsu | |
| 4,106,335 A | 8/1978 | Shatto | |
| D269,701 S | 7/1983 | Miller | |
| 4,602,619 A | 7/1986 | Wolf | |
| D285,137 S | 8/1986 | Svensson | |
| 4,607,625 A | 8/1986 | Schenck | |
| 4,776,581 A | 10/1988 | Shepherdson | |
| 4,907,571 A | 3/1990 | Futakami | |
| 4,981,307 A | 1/1991 | Walsh | |
| 5,054,137 A | 10/1991 | Christensen | |
| 5,080,191 A | 1/1992 | Sanchez | |
| 5,190,507 A | 3/1993 | Iijima | |
| D372,982 S | 8/1996 | Williams | |
| 5,632,723 A | 5/1997 | Grim | |
| 5,660,445 A | 8/1997 | Murray | |
| 5,850,928 A | 12/1998 | Kahlman et al. | |
| 5,893,367 A | 4/1999 | Dubats et al. | |
| 5,898,111 A | 4/1999 | Blankenship et al. | |
| 5,988,315 A | 11/1999 | Crane | |
| 5,996,823 A | 12/1999 | Dyson | |
| 6,079,578 A | 6/2000 | Dyson | |
| 6,125,792 A | 10/2000 | Gee | |
| 6,135,928 A | 10/2000 | Butterfield | |
| 6,204,620 B1 | 3/2001 | McGee et al. | |
| 6,269,944 B1 | 8/2001 | Taylor | |
| 6,313,595 B2 | 11/2001 | Swanson et al. | |
| 6,315,138 B1 | 11/2001 | Dyson | |
| 6,367,582 B1 | 4/2002 | Derby | |
| 6,378,465 B1 | 4/2002 | Austin | |
| 6,464,208 B1 | 10/2002 | Smith | |
| 6,612,449 B1 | 9/2003 | Otani et al. | |
| 6,668,668 B1 | 12/2003 | Peshkin | |
| 6,738,691 B1 | 5/2004 | Colgate et al. | |
| 6,813,542 B2 | 11/2004 | Peshkin et al. | |
| 6,907,317 B2 | 6/2005 | Peshkin et al. | |
| 6,928,336 B2 | 8/2005 | Peshkin et al. | |
| 6,942,630 B2 | 9/2005 | Behan | |
| 7,043,337 B2 | 5/2006 | Colgate et al. | |
| 7,120,508 B2 | 10/2006 | Peshkin et al. | |
| 7,185,774 B2 | 3/2007 | Colgate et al. | |
| 7,298,385 B2 | 11/2007 | Kazi et al. | |
| 7,381,163 B2 | 6/2008 | Gordon et al. | |
| 7,461,753 B1 | 12/2008 | Gatta et al. | |
| 7,526,847 B1 | 5/2009 | Arthur et al. | |
| 7,608,847 B2 | 10/2009 | Rees | |
| 7,756,601 B1 | 7/2010 | Van Dyke et al. | |
| 7,832,711 B2 | 11/2010 | Miyoshi et al. | |
| 7,883,450 B2 | 2/2011 | Hidler | |
| 7,973,299 B2 | 7/2011 | Rees | |
| 8,221,293 B2 | 7/2012 | Hoffman et al. | |
| 8,528,866 B2 | 9/2013 | Fradet | |
| 8,844,904 B2 | 9/2014 | Bogh-Sorensen | |
| D749,226 S | 2/2016 | Cooper et al. | |
| 2001/0027149 A1 | 10/2001 | Bingham | |
| 2002/0066711 A1 | 6/2002 | Taylor | |
| 2002/0100642 A1 | 8/2002 | Mehrman et al. | |
| 2003/0015905 A1 | 1/2003 | Sappei et al. | |
| 2003/0057408 A1 | 3/2003 | Kazerooni et al. | |
| 2003/0153438 A1 | 8/2003 | Gordon et al. | |
| 2005/0192159 A1 | 9/2005 | Jackson et al. | |
| 2006/0229164 A1 | 10/2006 | Einav | |
| 2007/0004567 A1 | 1/2007 | Shetty et al. | |
| 2007/0256890 A1 | 11/2007 | Petzl | |
| 2007/0278036 A1 | 12/2007 | Barta et al. | |
| 2008/0287268 A1* | 11/2008 | Hidler .................... A61H 3/008 482/69 |
| 2009/0215588 A1 | 8/2009 | Riener et al. | |
| 2010/0137772 A1 | 6/2010 | Tanaka et al. | |
| 2011/0017546 A1 | 1/2011 | Nichols, Jr. | |
| 2011/0100249 A1 | 5/2011 | Ipsen | |
| 2012/0000876 A1 | 1/2012 | Bergenstrale et al. | |
| 2012/0018249 A1 | 1/2012 | Mehr | |
| 2012/0283794 A1 | 11/2012 | Kaib et al. | |
| 2013/0153334 A1 | 6/2013 | Crew et al. | |
| 2014/0206503 A1 | 7/2014 | Stockmaster et al. | |
| 2014/0276306 A1 | 9/2014 | Dreske | |
| 2015/0320632 A1 | 11/2015 | Vallery et al. | |

FOREIGN PATENT DOCUMENTS

| | | |
|---|---|---|
| GB | 1207697 | 10/1970 |
| JP | 04202972 | 8/1994 |
| JP | 11004858 | 1/1999 |
| JP | 2005279141 | 3/2004 |
| WO | WO 2014/131446 A1 | 9/2014 |

OTHER PUBLICATIONS

PCT/US2016/016414 An Unofficial International Search Report and Written Opinion dated Jun. 2, 2016 for PCT/US2016/016414 filed Feb. 3, 2016, Inventor James G. Stockmaster et al.
U.S. Appl. No. 14/160,613—Co-Pending US Patent Application filed Jan. 22, 2014.
EP14742789.2—A European Search Report and Search Opinion dated Jul. 4, 2016.
PCT/US2016/038353 An unofficial International Search Report and Written Opinion dated Dec. 28, 2016 for PCT/US2016/038353 filed Jun. 20, 2016.
U.S. Appl. No. 14/160,613 Co-Pending US Patent Application filed Jan. 22, 2014, U.S. Pat. No. 9,510,991 Issued Dec. 6, 2016, Inventor James G. Stockmaster et al.
Unofficial Chinese Office Action dated Dec. 12, 2016 for Chinese Application CN201480017417.7.
International Family Information for CN101595055A.
International Family Information for CN102123687A.
PCT/US2016/038353 An Unofficial Invitation to Pay Additional Fees Sep. 6, 2016.
An Unofficial Korean Office Action dated Aug. 11, 2016 for Korean Application 10-2015-7022342 dated Aug. 11, 2016.
EP16747213.3—An Unofficial European Search Report and Written Opinion Dated Sep. 4, 2018 for European Patent Application EP16747213.3 dated Sep. 4, 2018.

(56) References Cited

OTHER PUBLICATIONS

BESI, Inc., BESI and Universal Securement Vests, Mar. 8, 2010, http://www.besi-inc.com/securements.html Mar. 8, 2010.
Unofficial Japanese Office Action dated Jun. 19, 2018 for Japanese Application 2015-555223 dated Jun. 19, 2018.
An Unofficial English translation of a Korean Office Action dated Oct. 22, 2018 for Korean Application 10-2017-7024743 dated Oct. 22, 2018.

* cited by examiner

MEDICAL REHAB BODY WEIGHT SUPPORT SYSTEM AND METHOD WITH HORIZONTAL AND VERTICAL FORCE SENSING AND MOTION CONTROL

This application claims priority under 35 U.S.C. § 119 from U.S. Provisional Patent Application No. 62/111,288 for a MEDICAL REHAB BODY WEIGHT SUPPORT SYSTEM AND METHOD WITH HORIZONTAL AND VERTICAL FORCE SENSING AND MOTION CONTROL, filed Feb. 3, 2015 by James Stockmaster et al. and from U.S. Provisional Patent Application No. 62/182,410 for a BODY HARNESS, filed Jun. 19, 2015 by Betty Dolce et al. This application is also a continuation-in-part of, and also claims priority under 35 U.S.C. § 119 from, U.S. patent application Ser. No. 14/160,613 for a MEDICAL REHAB LIFT SYSTEM AND METHOD WITH HORIZONTAL AND VERTICAL FORCE SENSING AND MOTION CONTROL, filed Jan. 22, 2014 by James Stockmaster et al. and from U.S. Provisional Application No. 61/755,007 for a MEDICAL REHAB LIFT SYSTEM AND METHOD WITH HORIZONTAL AND VERTICAL FORCE SENSING AND MOTION CONTROL, filed Jan. 22, 2013 by James Stockmaster et al., and where all of the above-identified applications are hereby incorporated by reference in their entirety.

The system disclosed herein relates to a body-weight support system, and more particularly to an improved support system, and method including exercise modes that are customizable or configurable and dynamic in nature, and which may include multiple configurations for a track system, where the system is capable of providing alternative functionality at differing locations, an adjustable and variable supportive force for users based upon, for example, a portion (e.g., percentage) of sensed body weight. The disclosed system further provides a user-interface that may be employed in a fixed, mobile, wired or wireless manner, and will enable the use of multiple support devices on a single track system.

BACKGROUND AND SUMMARY

The process of providing rehabilitative services and therapy to individuals with significant walking deficits and other physical impairments presents a challenge to even the most skilled therapists. For example, patients suffering from neurological injuries such as stroke, spinal cord injury, or traumatic brain injury often exhibit an inability to support themselves, poor endurance or walking patterns that are unstable. Such deficiencies make it difficult, at best, for the patient and therapist to engage in particular exercises, therapies, etc. Accordingly, it is increasingly common for such therapies to involve some sort of body-weight support system to reduce the likelihood of falls or other injuries, while enabling increased intensity or duration of the training or therapy.

Some existing support systems obstruct a therapist's interaction with the patient, by presenting barriers between the patient and the therapist. Other stand-alone support systems require assistance, or the patient, to manage the horizontal movement of the support system, rather than focusing on their own balance and preferred form of the therapy. In other words, the patient may be forced to compensate for the dynamics of the support system. Such a confounding effect could result in the patient's development of abnormal compensatory movements that persist when the patient is removed from the support system.

Yet a further problem with some systems is that under static unloading, the length of the supporting straps is set to a fixed length, so the subject either bears all of their weight when the straps are slack or no weight when the straps are taught. Static unloading systems are known to produce abnormal ground reaction forces and altered muscle activation pattern. Moreover, static unloading systems may limit the patient's vertical excursions (e.g., up and over steps, stairs and the like) and thereby prevent certain therapies where a large range of motion is required. Another problem observed with systems that are programmed to follow the patient's movement are significant delays in the response of the system (often the result of mechanics of sensors, actuators and system dynamics), where the patient feels that they are exerting greater force than necessary just to overcome the support system—resulting in the patient learning adaptive behaviors that may destabilize impaired patients when they ultimately begin self-supported activities for which they are being trained.

In light of the current body-weight support systems there is a need for a medical rehab support system and method that overcomes the limitations of the systems characterized above.

Disclosed in embodiments herein is a body-weight support system having an improved support system and method including exercise modes that are customizable or configurable and dynamic in nature, including numerous configurations for a track system, wherein the system is capable of providing alternative functionality at differing locations, an adjustable and variable supportive force for users based upon, for example, a percentage of sensed body weight. The disclosed system further provides a user-interface that may be employed in a fixed, mobile, wired or wireless manner, and the system will allow the use of multiple units on a single, possibly looped, track without collision or interference between adjacent units.

Further disclosed in embodiments herein is a system for supporting the weight of a person, comprising: a track or similar support structure including an indexed portion thereon (could also be supported by an arm or a gantry with ability to programmatically define a path over which the gantry trolley can move); a movable support operatively attached to the track, the support being movable along a path defined by the track and in a first direction and in a second direction generally opposite to the first direction; a first drive attached to the movable support, said first drive moving the support along the path defined by the track, wherein the first drive is operatively coupled to the indexed portion on the track to reliably control the horizontal position of the support along the track; an actuator attached to the movable support, said actuator including a second drive for driving a rotatable drum, said drum having a first end of a strap (or other flexible, braided member) attached thereto and the strap wound about an outer surface of the drum, with a second end of the strap being coupled to a support harness (or similar supportive/assistive device) attached to support a person; a first sensor for detecting a horizontal force applied to the support via the strap; a second sensor for sensing a vertical force applied to the strap; and a control system configured to receive signals from the first and second sensors and a user interface and to control the movement of at least the first and second drives to facilitate the support and movement of the person, where the control system dynamically adjusts the amount of support provided to the person by altering at least the vertical force applied to the strap via the drum and second motor.

Also disclosed in embodiments herein is a system for supporting the weight of a person, comprising: a track including a plurality of extruded members joined end-to-end, and a plurality of electrical rails arranged longitudinally along an interior portion of the track for each portion of track, wherein at least one extruded member includes a generally planar upper surface extending in a longitudinal direction, opposing sides extending longitudinally and downward from each side of the upper surface, and where a combination of the upper surface and downward-extending sides form the interior portion of the track; each of said opposing sides further including a shoulder extending in an outward direction therefrom; a movable support unit operatively attached to the track, the movable support unit being movable along a path defined by the track in a first direction and in a second direction generally opposite to the first direction; a first drive attached to the movable support unit, said first drive moving the support along the path defined by the track, wherein the first drive is frictionally coupled to a surface of the track to control the horizontal position of the support along the track, wherein said first drive is maintained in frictional contact with the interior portion of the track and where the movable support unit is suspended from rollers resting on each of the shoulders extending from the opposing sides of the track; an actuator attached to the movable support unit, said actuator including a second drive for driving a rotatable drum, said drum having a first end of a strap attached thereto and the strap wound in an overlapping coil fashion about an outer surface of the drum, and a second end of the strap being coupled to a support harness attached to support a person; a first sensor for detecting a horizontal force applied to the movable support unit via the strap, including a strap guide operatively attached to and extending from said movable support unit, said strap guide being attached to a load cell in a manner causing a change in the load cell output when the strap is pulled in a direction forward from or backward from vertical; a second sensor for sensing a vertical force applied to the strap, including at least one pulley between the drum and the person supported by the strap, wherein the pulley is connected on one end of a pivoting arm, said arm being pivotally attached near its midsection to a frame member coupled to the movable support, and where an opposite end of said pivoting arm is operatively associated with a load cell such that the load cell is placed only in compression in response to a load suspended on the strap; and a control system configured to receive signals from the first and second sensors, and a user interface, and to control the movement of at least the first and second drives to facilitate the support during movement of the person, where the control system dynamically adjusts the amount of support provided to the person by moving the moveable support unit horizontally along the track to follow the person, thus minimizing the effect on the person, and by altering the vertical force applied to the person via the strap, the drum and second motor, to be suitable for a given patient.

Further disclosed in embodiments herein is A method for supporting the weight of a person for purposes of rehabilitation therapy, comprising: providing a track, the track including a plurality of extruded members joined end-to-end, and a plurality of electrical rails arranged longitudinally along an interior portion of the track for each portion of track, wherein at least one extruded member includes a generally planar upper surface extending in a longitudinal direction, opposing sides extending longitudinally and downward from each side of the upper surface, and where a combination the upper surface and downward-extending sides form the interior portion of the track; each of said opposing sides further including a shoulder extending in an outward direction therefrom; operatively attaching a movable support unit to the track, the movable support unit being movable along a path defined by the track in a first direction and in a second direction generally opposite to the first direction; moving the support unit along the path defined by the track using a first drive attached to the movable support unit, wherein the first drive is operatively coupled to a surface of the track to control the horizontal position of the support along the track, and where the movable support unit is suspended from rollers resting on each of the shoulders extending from the opposing sides of the track; controlling the vertical position of the person using an actuator attached to the movable support unit, said actuator including a second drive for driving a rotatable drum, said drum having a first end of a strap attached thereto and the strap wound in an overlapping coil fashion about an outer surface of the drum, and a second end of the strap being coupled to a support harness attached to support the person; detecting a horizontal force applied to the movable support unit via the strap using a first sensor, the first sensor including a strap guide operatively attached to and extending from the movable support unit, the strap guide being attached to a load cell in a manner causing a change in the load cell output when the strap is pulled in a direction forward from or backward from vertical; sensing a vertical force applied to the strap using a second sensor, the second sensor including at least one pulley between the drum and the person supported by the strap, wherein the pulley is connected on one end of a pivoting arm, said arm being pivotally attached near its midsection to a frame member coupled to the movable support, and where an opposite end of said pivoting arm is operatively associated with a load cell such that the load cell is placed only in compression in response to a load suspended on the strap; and providing a control system configured to receive signals from the first and second sensors, and a user interface, and to control the movement of at least the first and second drives to facilitate and support movement of the person, where the control system dynamically adjusts the amount of support provided to the person by moving the moveable support unit horizontally along the track to follow the person.

Figure 1:
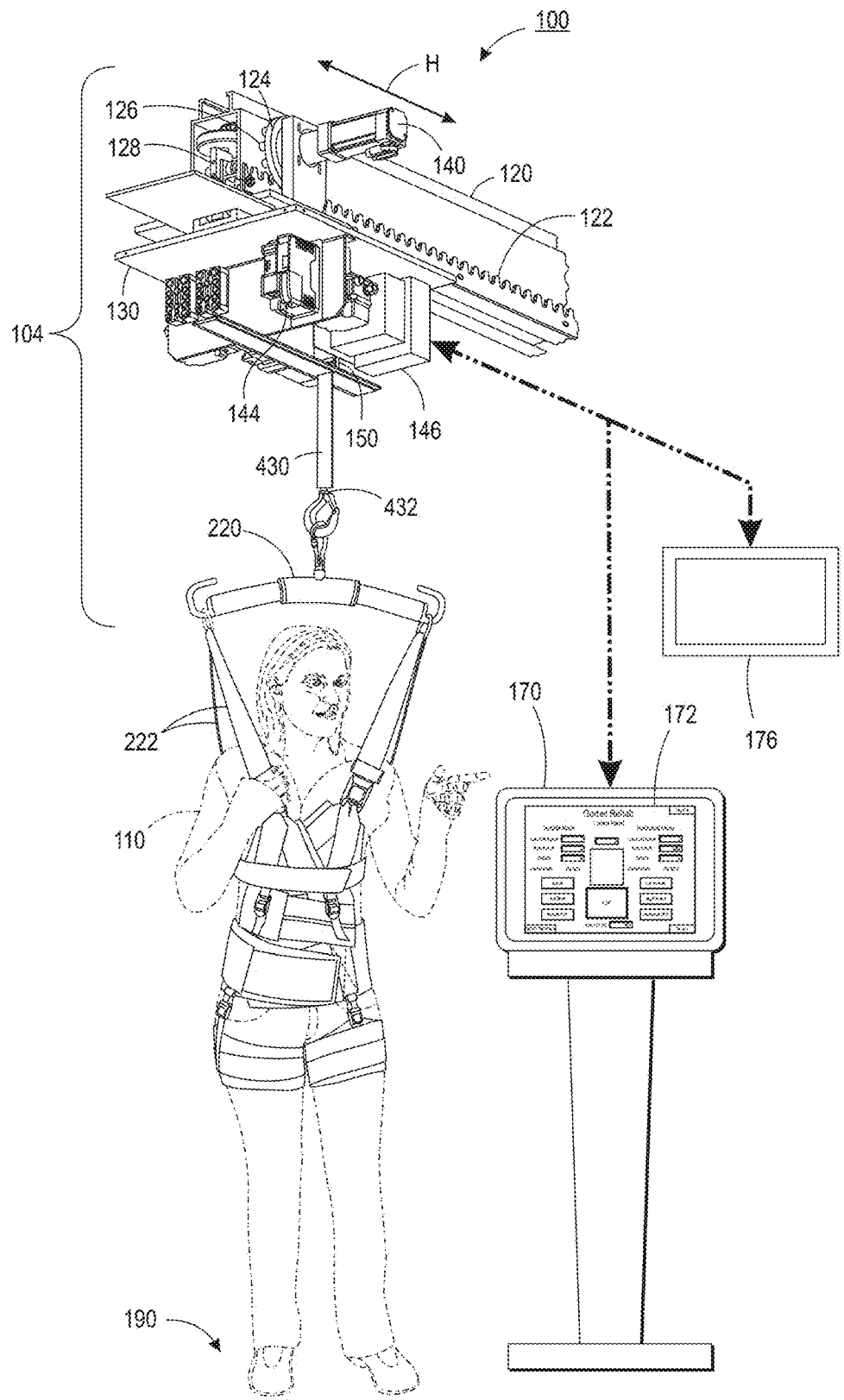
FIG. 1 is a representation of an exemplary rehab support system.
Figure 2:
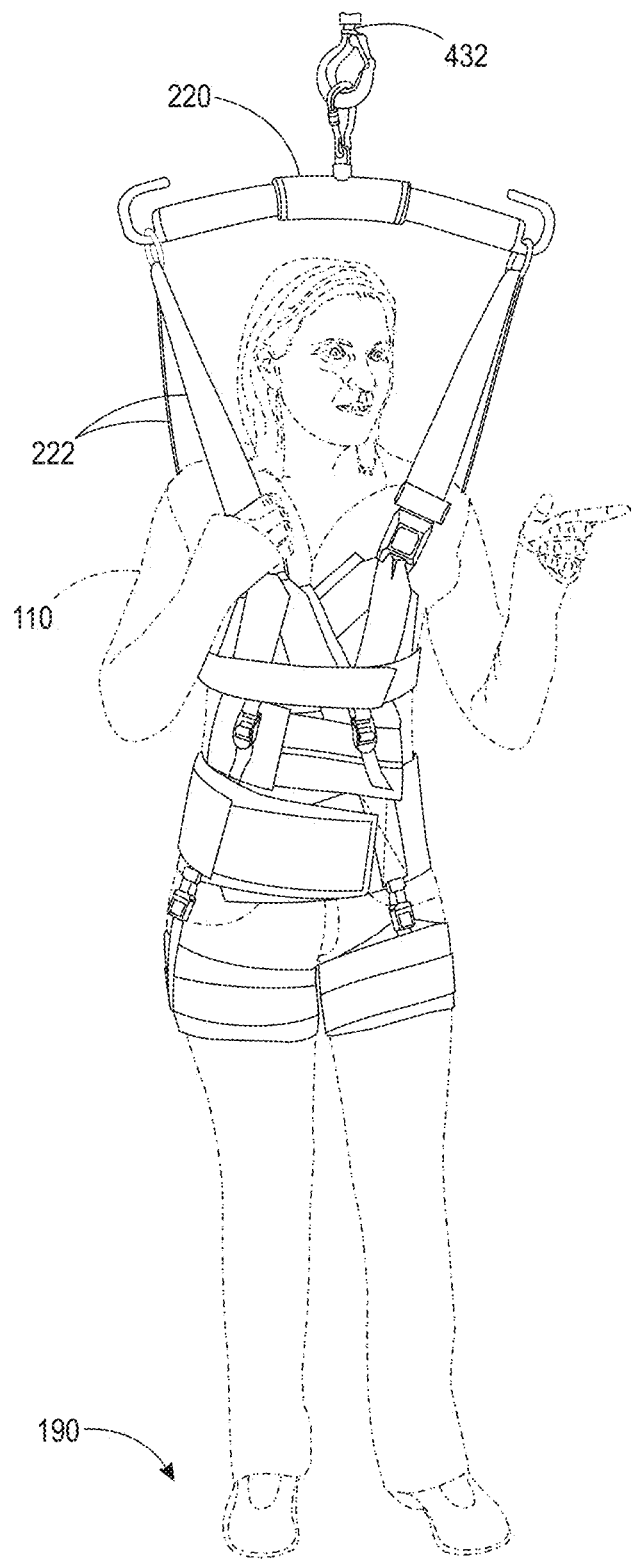
FIG. 2 is an illustration of a support harness assembly with a person in the harness.
Figure 3:
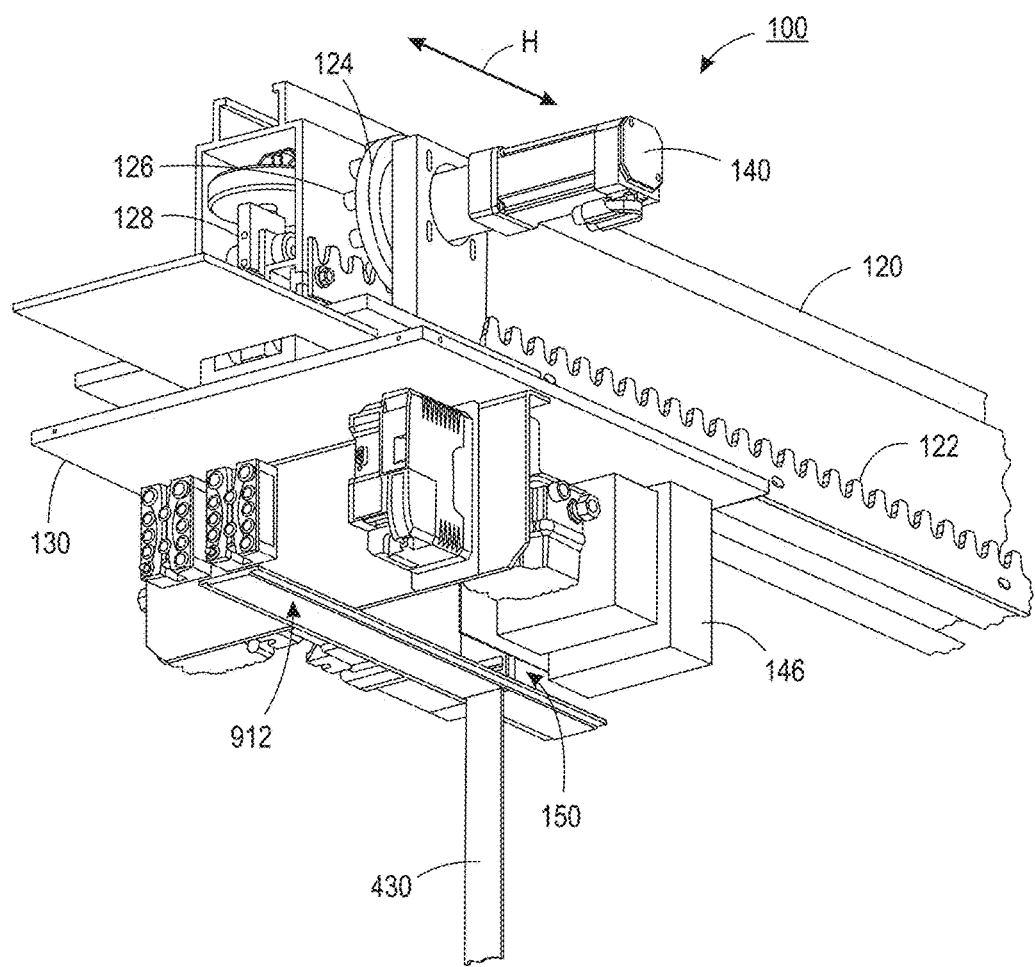
FIG. 3 is a view of a support on a section of track in accordance with a disclosed embodiment.
Figure 4:
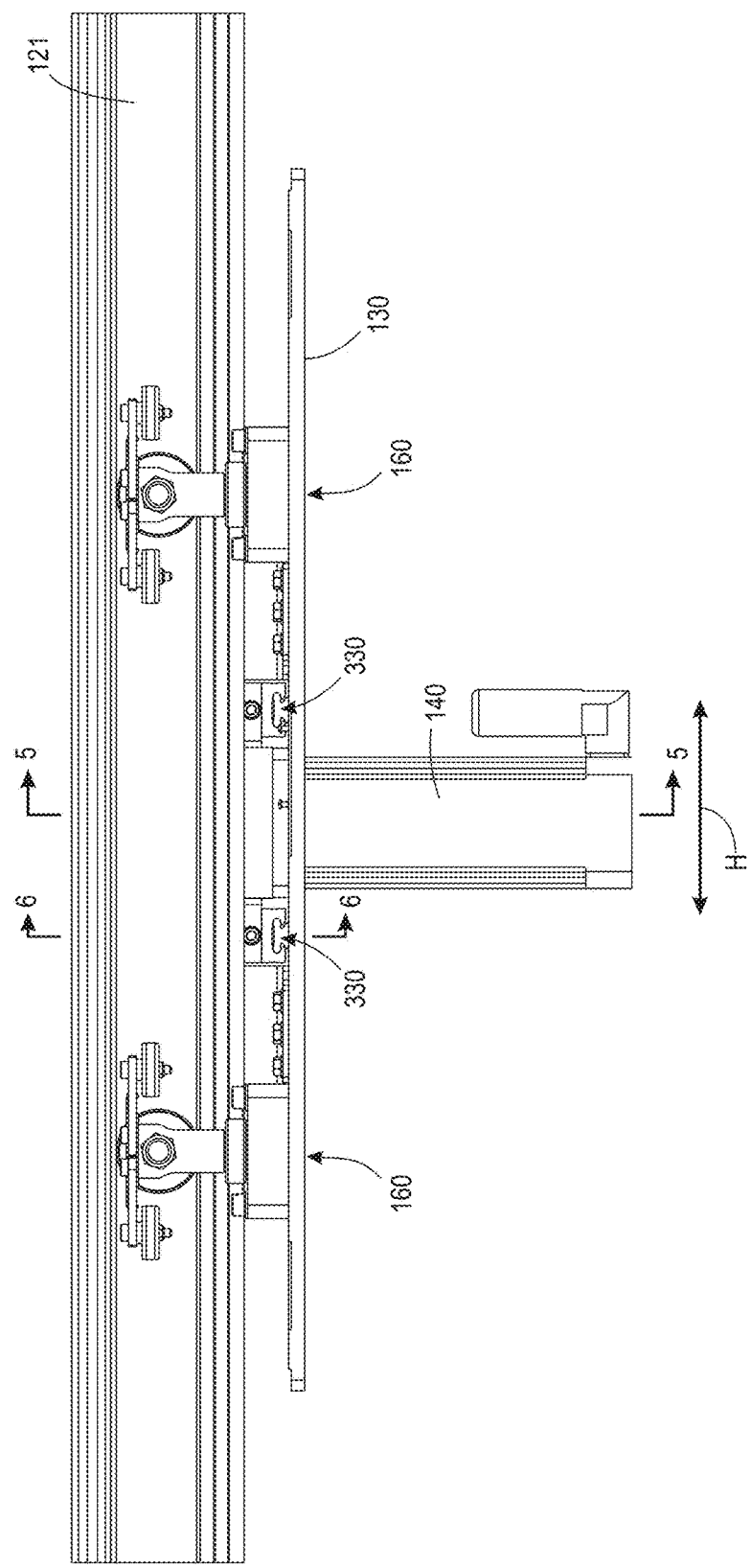
FIG. 4 is a side view of a support on a section of track in accordance with an alternative embodiment.

The various embodiments described herein are not intended to limit the disclosure to those embodiments described. On the contrary, the intent is to cover all alternatives, modifications, and equivalents as may be included within the spirit and scope of the various embodiments and equivalents set forth. For a general understanding, reference is made to the drawings. In the drawings, like references have been used throughout to designate identical or similar elements. It is also noted that the drawings may not have been drawn to scale and that certain regions may have been purposely drawn disproportionately so that the features and aspects could be properly depicted.

DETAILED DESCRIPTION

Figure 17:
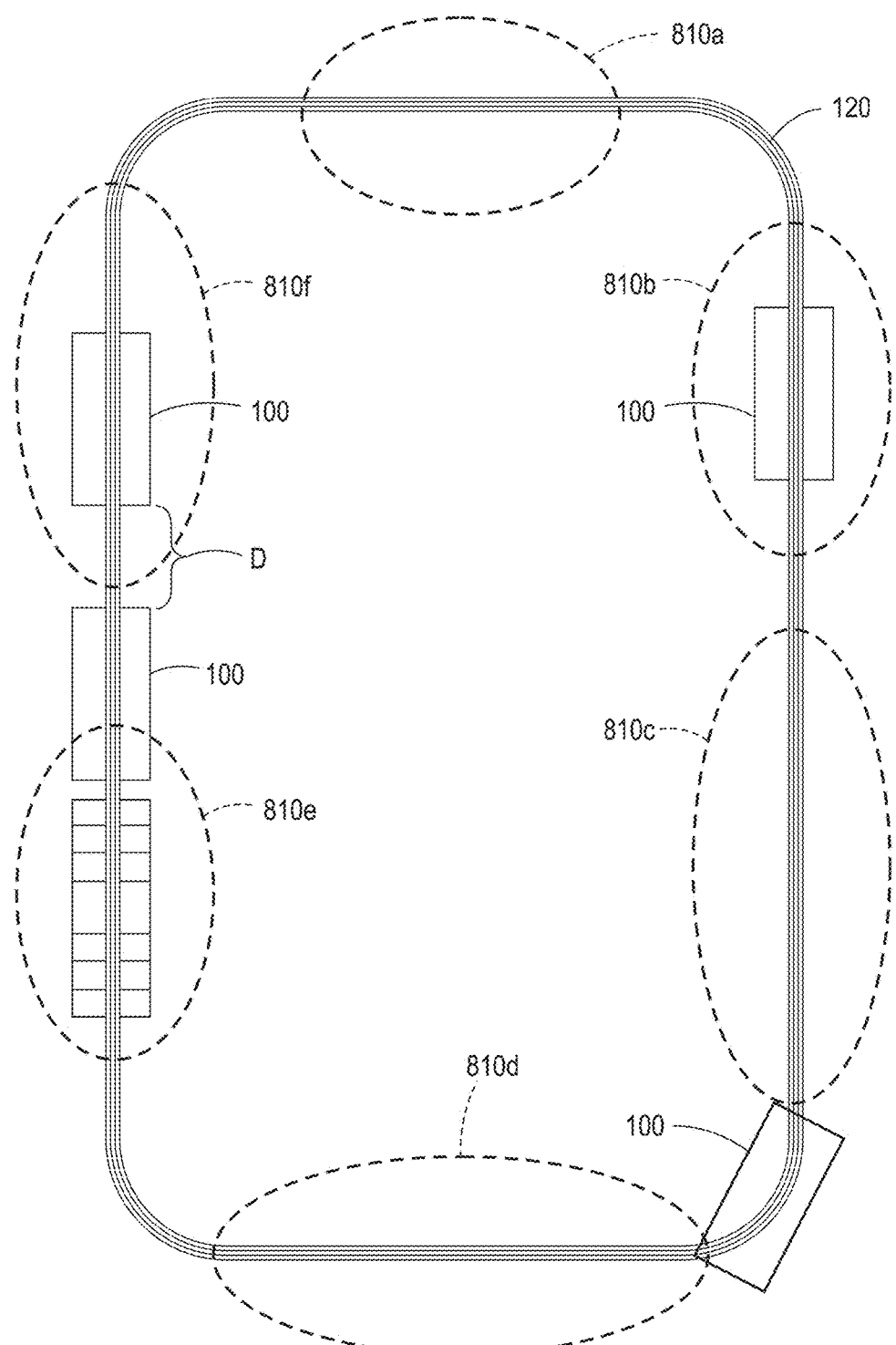
FIGS. 17 and 18 are exemplary illustrations of a generally rectangular track system.
Figure 18:
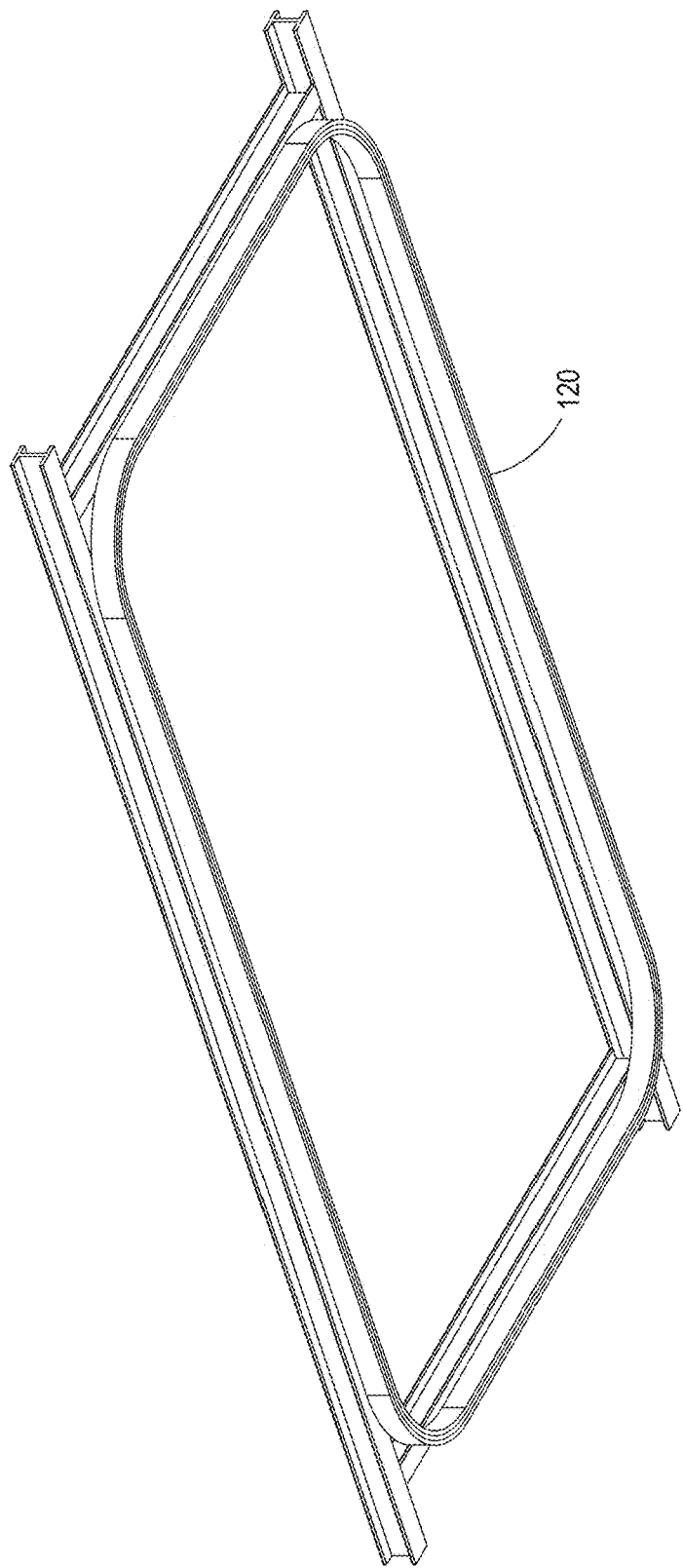

Referring to FIG. 1, depicted therein is a system 100 (e.g., SafeGait™ 360° Balance and Mobility Trainer system) for supporting a selectable portion (e.g., percentage) of the weight of a person or patient 110. In a general sense, the system comprises a track 120. Although the following disclosure is largely directed to a track-type system, for example a looped track path as illustrated in FIGS. 17-18 (e.g., no-beginning or end), various aspects and features of the disclosed system and associated methods are contemplated as being supported by alternative support structures such as an arm (e.g., Jib crane, Gorbel EasyArm™), a cantilevered track section, and perhaps even a gantry with the ability to programmatically define a path over which the gantry trolley can move. In such alternative embodiments, a movable support unit or truck 104 includes a movable support or base 130, where the support 130 may be fixed to another movable member or may itself be movable relative to a supporting structure. The movable support unit further includes other components such as a horizontal drive 140, actuator 400, etc. as will be further described below (e.g., FIGS. 11, 14).

The movable support 130 is, in the embodiment of FIG. 1, operatively attached to the track 120, the support being movable along a path defined by the track. Moreover, the generally horizontal movement (H) of the support relative to the track or path along a longitudinal or central axis of the track or track section, and may be in both a first direction and in a second direction generally opposite to the first direction. While illustrated as a horizontal track over which the support 130 travels, also contemplated is a track system where one or more portions or sections of track 120 may be raised or lowered relative to the remainder of the track and/or where a surface or flooring 190 beneath the track is raised or lowered at varying positions, so as to provide or simulate typical scenarios where the person is proceeding up or down an incline, stairs, curbs, etc.

Continuing with FIG. 1, a first or horizontal drive 140 is attached to the movable support, and the first drive includes, in one embodiment, a pinion 124 configured to interact with the toothed indexing portion or rack and in response to the rotational motion of the drive 140, the support is moved along the path defined by the track. As will be appreciated, the horizontal drive is thereby operatively coupled to the indexed portion on the track to reliably control the horizontal position of the support along the track. Using an appropriate drive, for example a servo drive motor provided by B&R (Model #8LS35), it is possible to be relatively precise in both controlling and monitoring the position of the drive and support. More specifically, due to the relationship of the pins or lugs 126 on the pinion 124, and the direct coupling of such pins to the "teeth" on the rack 122, any angular rotation of the pinion under the control of the motor will advance or retract the position of the support along the track.

In contrast, in the alternative embodiment depicted in FIGS. 4-10, the horizontal drive 140 may be frictionally engaged with a surface (e.g., interior wall) of track 120. By driving along an interior wall, the system reduces the likelihood of debris interfering with the frictional drive. As will be appreciated, the operation of the horizontal drive 140 is controlled by a AC servo drive 144, or similar device that is both under programmatic control and further receives signals controlling its operation, for example via a horizontal force sensing assembly 150 and/or via a programmable device such as an industrial PC 170 including a user interface 172 such as that depicted by reference numeral 170 in FIG. 1. Power is supplied to the servo drive 144 via power supply 146.

Although depicted as a floor-mounted device, industrial PC 170 may take one or more forms and may be portable, floor-mounted, and may also include remote-control devices such as tablet 176. For example, controller 170 may be a programmable logic controller, available from B&R (Model #PP500). In one embodiment, while there may be a main or centralized control point, that control point may consist of or include a wireless transceiver to communicate with one or more hand-held devices (smart phones, tablets, or customizable controllers) that are able to remotely control the operation of the system. Controller 170 may further include memory or storage devices suitable for recording information relating to system usage, patient information, etc. Wireless communications techniques may employ one or more radio frequencies (e.g., Bluetooth), as well as other bandwidth spectrums such as infrared. In one embodiment, the disclosed system may employ an Ethernet or similar communication protocol and technology to implement communications between the various system components. In this manner, a therapist or person attending the patient 110 may be able to control the operation of the device, select, set or modify a program for the patient, etc. as further represented in FIGS. 22-56. In other words, the therapist may be able to modify or change parameters associated with a patient on the fly using a kiosk, handheld tablet, etc., where using the touch-screen display of interface 172 or similar wireless remote interface 176 the operation of the movable support 104 may be controlled or adjusted. It is also contemplated that the communications may be of a wired nature between a controller 170 and AC servo drive 144.

The following is an exemplary representation and description of an exemplary software design of the SafeGait™ 360° Balance and Mobility Trainer system 100.

1 Introduction 1.1 Scope

This description provides design detail for the custom software modules of the SafeGait 360° Balance and Mobility Trainer system (see "System Overview," below). Specifically disclosed are designs of the interfaces, structures, and implementation specifics of the Kiosk (e.g., 170) and Remote (e.g., 176) user interfaces (e.g. 2900) and the supporting software components upon which they depend for integrating and functioning within the system as a whole.

1.2 Objectives

This document is intended to provide the implementation details of the software components of the system, the reasoning for their design structure, and how these modules integrate with the SafeGait hardware and firmware.

2 Design 2.1 Considerations and Constraints

Several constraints exist for this system, as defined within the system requirements (SRS), which drove the design: (1) The user interfaces support a touchscreen; (2) The Kiosk and Remote hardware may not run the same operating system platform; (3) Aside from providing a TCP communications interface, the Actuator is considered a black box; (4) The system may accommodate future "smart" technologies, (e.g., Google Glass, Smart Watch, etc.); (5) The system should be capable of supporting future Kiosk and Remote hardware; and (6) The system should support future use cases, such as data concurrency between multiple systems at a single facility. Together, these considerations lead to the architecture of a cross-platform, web-based approach based on loose coupling between software and hardware components, a top-level model-view-controller (MVC) component structure, and the use of industry-standard technologies to ease integration and expandability.

2.2 Top-Level Approach

The requirements noted above may require the user interfaces to change if operating platforms change or are added, the data modeling strategy to change if a centralized data store becomes necessary, or the interface to the black box Actuator to change. As such, being able to decouple one software component from another based on their roles within the system becomes a critical requirement—the user interface should not embed communications code or data management code within its source. Instead, the user interface should invoke another component, using an agreed-upon contract, to execute a message to the Actuator, or fetch a record from the data store. Thus, the design approach takes advantage of the fact that the software system can effectively be segregated into the following MVC categories: Kiosk and Remote User Interfaces ("view"); Patient and User Data Store ("model"); and Communications and Background/ Supporting Tasks ("controller")

The top-level separation of concerns (SoC) outlined above allow any piece of the various software components comprising the system to be updated, changed, or even re-written with minimal impact on the rest of the components. This organization is summarized in FIG. 27, with the component labeled "Service" managing the requests and responses from the other components of the system (this component will be discussed in detail later in the document).

Figure 27:
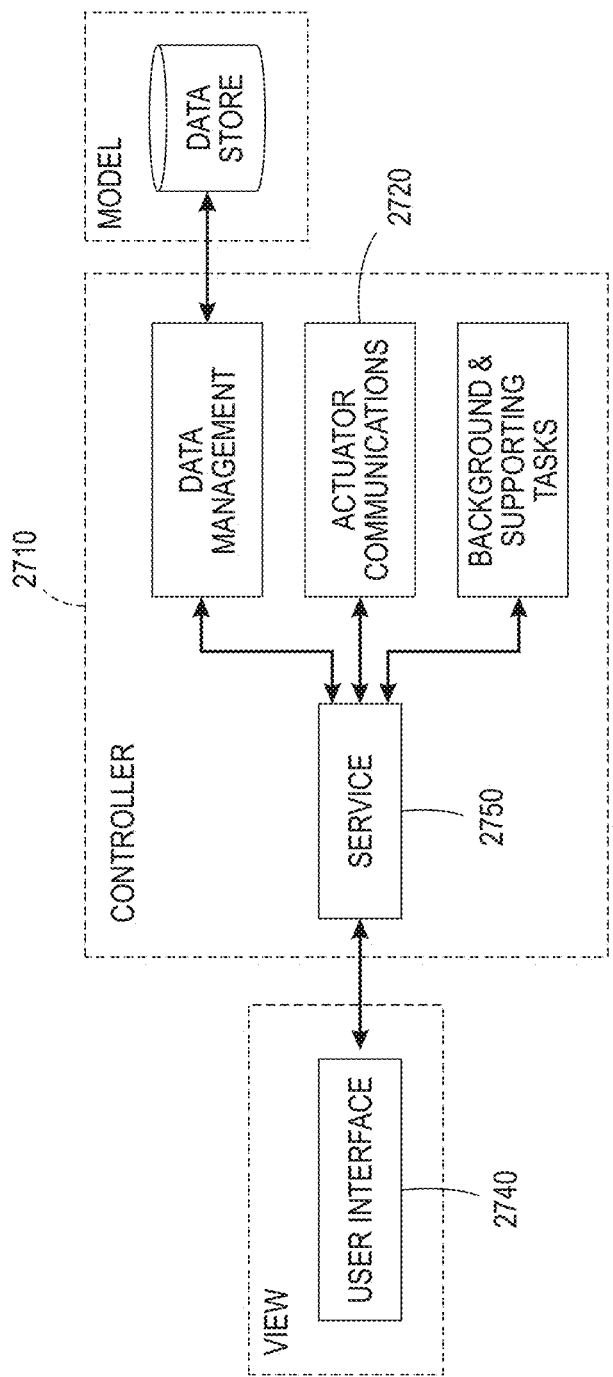
FIGS. 27-31 are illustrations of a software environment for embodiments including a kiosk and remote applications for system control and data storage.

As characterized by FIG. 27, which depicts the MCV software architecture, within each model-view-controller category, the same SoC paradigm is also maintained. For instance, within the controller component 2710, the communications module 2720 that interfaces with the Actuator will be maintained as a different entity (e.g., library) from the module that communicates with the user interfaces 2740. This allows for the Actuator's protocols to change without needing to change the entire controller component. This also presents the software as a service design pattern, wherein a specific module or entity is only activated when its tasks are required. This type of segregation also lends itself well to the use of web-based technologies, which is also a favorable approach to multiple aspects of the elucidated set of system requirements:

1. When considering that the operating systems utilized by the Kiosk and Remote hardware components may differ, a web-based user interface better lends itself toward a consistent look and feel and functional behavior across platforms;
2. Web technologies are designed to communicate between different systems—many different data formatting protocols as well as transport protocols are built into the web platforms;
3. Web technologies provide comprehensive support for many types of data storage platforms; and
4. Web technologies guarantee scalability to more systems, more components, and more data.

Thus, the controller component is implemented as a web service (e.g., the "Service" module 2750 in FIG. 27), to which the web application comprising the user interface sends requests and receives responses, and which invokes the functions necessary for data and system management. The details of the implemented structure of these components are elucidated in the "System Overview" section below.

2.3 Privacy and Security Risks

As a training device, patient privacy and patient data security is always of concern. This category of risks may be mitigated both by user training as well as within the software and its configuration, including the following: Persistent data stores will segregate identifiable fields (e.g. name, date of birth, etc.) into their own tables, and pursue the identification of a patient throughout the system using unique, secondary identifiers; Persistent data stores will encrypt fields that may be considered identifiable; The user interfaces will require authentication and authorization to access system data; The system will run on a closed, secured, private network; and The user interface will not display sensitive, identifiable information when not necessary.

2.4 Development Platforms

In one exemplary embodiment, the Kiosk platform is based upon a Windows 8.1 Professional, 64-bit computer. This selection drives the technology baseline of the architecture. For example, for the purpose of better integrating with Microsoft technologies, the following configurations and their corresponding software components may be used:

Microsoft .NET 4.5 Framework with C#

Frameworks:

Entity Framework 6—Used for data modeling and management

WebAPI Framework—Used for Web Service implementation

Infrastructure:

Internet Information Services (IIS) 7.0—Used to host web service

SQL Server 2014 Express—Used as data store

Chrome Browser 39 or later

Because the user interfaces are essentially web applications that are compiled to different target platforms, Microsoft technologies may not be suitable. Instead, a more platform-agnostic development configuration is considered such that the cross-compilation toolchain, Cordova, may be used to create native application packages for the target environments, where applicable. Additionally, the use of a responsive design template (e.g., Bootstrap) allows for automatic reconfigurations of the user interface depending on the detected screen size, such as between the Kiosk 170 and the Remote 176.

The combination of these technologies—generic web application, responsive styling template, and a cross-compiling toolchain—enables code reuse between the Kiosk and Remote components and easier source code maintenance. The following underlying frameworks are used for the user interfaces:

Web Application:
HTML5—Used for screen layouts
CSS3 (with Bootstrap 3 template)—Used for user interface look and feel
JavaScript—Used as the backend infrastructure as well as for client-side behavior
jQuery—Core library of common function (dependency of many libraries used)
AngularJS application infrastructure with the following plugins:
  ngResource (angular-resource)—For interacting with RESTful services
  ngCookies (angular-cookies)—For reading/writing browser cookies
  ngSanitize (angular-sanitize)—For operating with well-formed HTML
  ngAnimate (angular-animate)—For support for CSS3 animations
  ngTouch (angular-touch)—For touch event support (i.e., touchscreens)
  uiRouter (angular-ui-router)—For managing navigation hierarchies
  uiMask (angular-ui-utils)—For input validation
  angular-base64—For supporting Base64 encoding
Date/Time tools:
  MomentJS—Parsing, validating, and displaying dates
Charting tools:
  C3 charts (using D3 technology)
Other utilities:
  MathJS—Used for formatting and calculations not provided by default
Cordova for cross-compiling to Kiosk and Remote operating platforms 3 Environmental Configurations 3.1 Kiosk Hardware The Kiosk and/or the Remote hardware may be a Windows 8.1 Professional tablet that supports a touchscreen. It needs to have IIS installed and be configured with the capability of running the web service component of the system such that external entities may connect to it.

Specific Kiosk configuration details include tasks such as operating system restrictions, installation of software, and configuration of users, rights, and privileges. From a software systems perspective, the kiosk's wireless network adapter will be set up to automatically connect to the "SafeGait" network broadcasted by the wireless router (mentioned below.) The kiosk will be configured to use a defined IP address and subnet mask.

3.2 Remote Hardware

The Remote hardware should be small enough such that a user can comfortably hold it in one hand, thereby leaving the other hand free to assist the patient. Additionally, the software platform running on the Remote hardware should have the following capabilities:

Connecting to the "SafeGait" wireless (WiFi) network
Setting a static Internet Protocol (IP) address
Touchscreen support
Supported by Cordova 3.3 Wireless Router A standard wireless router will be used to create the private network between the actuator, kiosk, and remote. The router will be configured with a known SSID and WPA key. The router's IP address and subnet will be predefined.

3.4 Network Attached Storage (NAS)

The Network Attached Storage is designed to be used as a data storage and backup unit and will employ configuration restrictions similar to the Kiosk and Remote operating platforms.

4 Software System Design 4.1 System Overview

Figure 28:
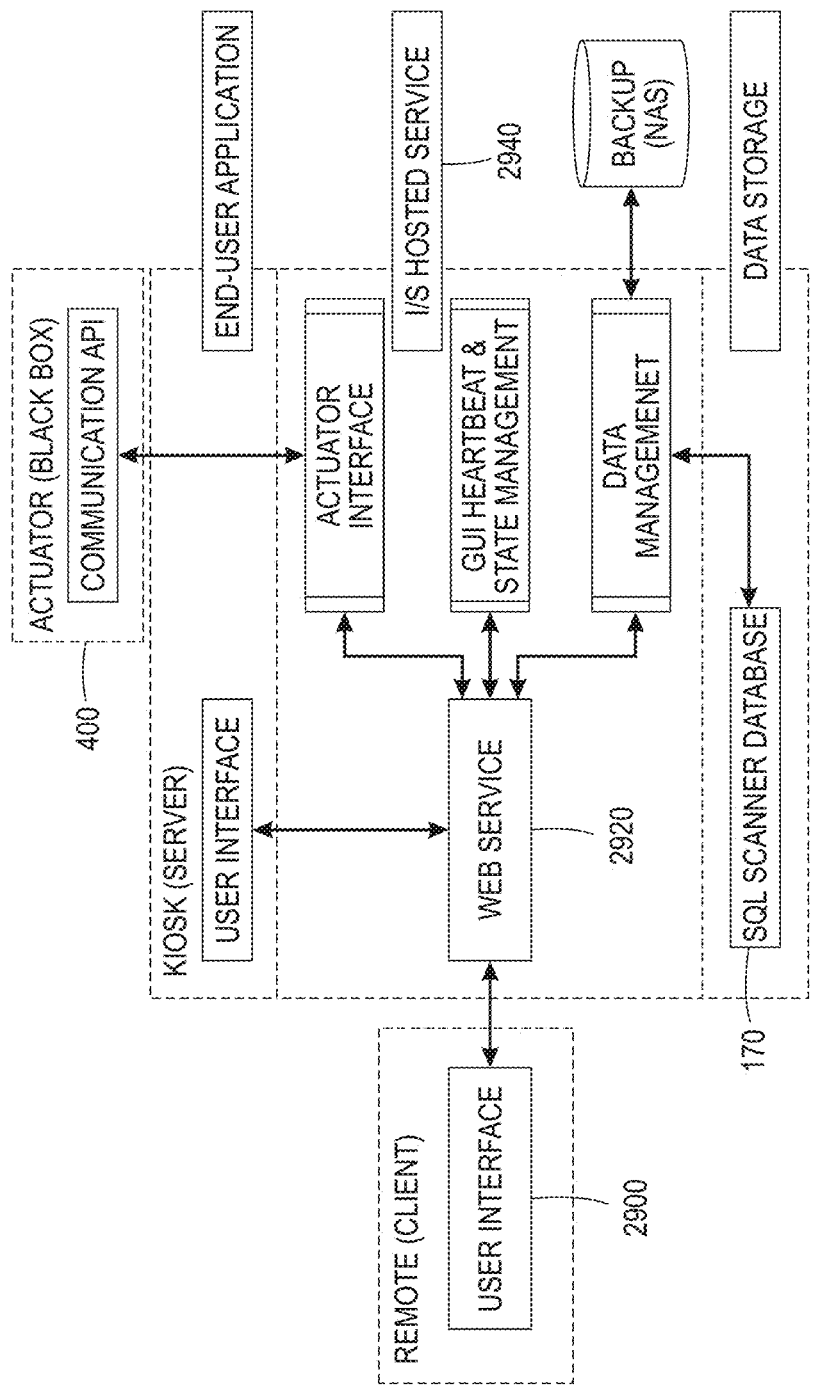

Based on the system requirements, the SafeGait 360° software system was designed with the components of FIG. 28. FIG. 28 illustrates major components by their task responsibilities and where they reside in the hierarchy of modules. It is important to note that within the "IIS Hosted Service" space 2940, the items labeled "Actuator Interface," "GUI Heartbeat & State Management," and "Data Management" may be physically separate (e.g., the Actuator Interface DLL), or structurally part of the web service (e.g., GUI State Management). The key is that the Web Service component 2920 is responsible for exposing and managing multiple backend tasks relegated to the server (Kiosk) within the system.

Not pictured in the diagram is a logging module, which may be a separate entity that is invoked by multiple sub-components of the system. The logging module writes files to the database in a looped structure, such that the most recent information regarding actions undertaken within the system may be reviewed. Further details on each of the components depicted in FIG. 28 may be found in the sections below.

4.1.1 Safety Considerations

As a training device whose use requires that a live patient be attached to the system, safety is of utmost concern. The software components are not directly responsible for how the harnessed individual is managed while the system is in use insofar as it is the Actuator's firmware that has direct control. However, the system serves to relay requests from the therapist to the Actuator, thereby indirectly impacting safety. Thus, the following safety considerations, as defined within the system requirements, are reiterated here:

1. The system must always be aware of whether the Actuator is present;
2. There must be a way to forcibly and immediately tell the Actuator to stop movement;
3. There must be a way to know which user interface (Kiosk versus Remote) has control of the Actuator;
4. Should auxiliary control interfaces (e.g., the Remote) lose connection, a primary control interface (e.g., the Kiosk) needs to automatically regain control;

5. The user interface must adequately be able to display any perceived issues from any system component to the end user; and
6. As an audit trail, actions taken by the software system should be logged for offline evaluation.

4.2 System Interfaces

As seen in FIG. 27, the various software components of the system require the capability to communicate with each other to relay information, to command the Actuator, and to persist system data. Specifically, the user interfaces on the Kiosk and Remote utilize the Web Service to interface with the rest of the system. The Web Service, in turn, invokes various different modules in order to relay messages to and from the Actuator, send and retrieve data from the data store (e.g., database), and to manage various other low-level system states and tasks.

To affect the communications, the system is designed to communicate over the TCP/IP protocol, within a closed, wireless network. In one embodiment the Web Service uses JSON-formatted text as the scheme for message transmission over HTTP. Details on the Web Service's design, responsibilities, and functions are discussed below. It will, however, be appreciated that alternate schemes may be employed for message transmission and communications between or within the system components.

Communications with the Actuator (2720) employs the creation of connectionless, UDP-style datagram packets as defined by the provided (black box) Actuator API before being pushed over a TCP transport layer. Communications with the backend database is accomplished using Microsoft's built-in data frameworks. However, the underlying technology behind the transmission of data functions also utilizes TCP. This layer is not discussed in detail as it is encapsulated through Microsoft's programming libraries. The structure and design of the data layer itself, however, is discussed below.

4.3 Background Tasks

4.3.1 Admin Service

This windows service is responsible for handling the exit and shutdown requests from the Kiosk user interface. When the user interface receives a request to exit or shutdown, it is forwarded to the Web API, which sends the command signal to the windows service. The windows service then performs the necessary action under the appropriate privileges. This service is automatically started when the operating system boots up.

4.3.2 Database Backup Scheduled Task

The data store for patient and session information is routinely backed up to the attached NAS unit. This is a system-level configuration to run the backup procedure as a Windows-level Scheduled Task. Thus, the operating system becomes responsible for the execution of backup, and logs successes and failures automatically.

4.4 WebAPI

The WebAPI is the entity responsible as the communications pipe between the different components of the software, as well as between the software and the Actuator. This is a managed set of libraries that are divided into functional groups, as described below. In one embodiment live documentation of each API function, as well as its usage, can be found on the server on the Kiosk by navigating to an appropriate URL.

4.4.1 User Management

.NET SimpleMembership may be used to support or administer the user accounts of the system. Three roles will be created to restrict access to certain features of the system: Therapist (user); Admin (admin); and Service Technician (superuser).

4.4.1.1 User Account API Resources 4.4.1.1.1 Login

Log user into system. This user is given system control.

4.4.1.1.2 Logout

Log user out of system. Since there is no longer system control, the system is disconnected from the actuator.

4.4.1.1.3 Add User

Add a new user account to the system. Admin or Service Technician role required.

4.4.1.1.4 Update User

Update existing user account details. Admin or Service Technician role required.

4.4.1.1.5 Reset Password

Reset user account password to known default password; Admin or Service Technician role required.

4.4.1.1.6 Change Password

Allow any user to change their password.

4.4.1.1.7 Disable/Enable User

Disable/Enable user accounts. This has the effect of preventing users from logging into the system. Admin or Service Technician role required.

4.4.2 Data Management 4.4.2.1 Patient API Resources

The patient resources are provided to allow the management or administration of patient information as may be stored in the database.

4.4.2.1.1 Add Patient

Add a new patient record.

4.4.2.1.2 Update Patient

Update an existing patient record.

4.4.2.2 Session API Resources 4.4.2.2.1 Add Session

Associate a new session, or "Plan of Care," with an existing patient record.

4.4.2.2.2 Update Session

Update an existing patient session.

4.4.2.3 Predefined and Custom Tasks API Resources 4.4.2.3.1 Get Tasks

Retrieve a listing of predefined tasks that can be performed by the patient.

4.4.2.3.2 Add Custom Task

Add a new custom task to the set of available tasks.

4.4.2.4 Historical Data API Resources 4.4.2.4.1 Get Patient Sessions

Retrieve a listing of the completed patient sessions, and their performed tasks.

4.4.2.4.2 Get Patient Goals (by task type)

Retrieve a historical listing of the patient's goals by task type.

4.4.2.4.3 Get Session Task Metrics (by task type)

Retrieve a historical listing of task metrics by a given task type.

4.4.3 System Management 4.4.3.1 Background Tasks 4.4.3.1.1 Heartbeat Monitor The heartbeat monitor task tracks the last heartbeats from the kiosk and remote user interfaces. If either the kiosk or the remote has control of the system, and the monitor does not receive a heartbeat in a required interval, system control is released from that device. The monitor logs any of these notable events to the database.

4.4.3.1.2 Actuator Connectivity Monitor

The actuator activity monitor is responsible for tracking two system events. In order for the system to be connected to the actuator, a user needs to be logged in at the kiosk. If the system loses actuator connectivity while a user is logged in, this task attempts to re-establish connectivity with the actuator. If a user logs out of the kiosk, this task also ensures that the system disconnects from the actuator.

4.4.3.2 System API Resources

4.4.3.2.1 Kiosk/Remote Heartbeat

The kiosk and remote user interfaces will invoke this API resource to report into the system. The response to this request is a snapshot of the system's state: who is logged in, what device has control, and the UI session data of the controlling source. This is how synchronization is facilitated between the kiosk and remote.

4.4.3.2.2 Grab System Control

Only one device, kiosk or remote, may have control of the system at a time. Either device can take control from the other. This API resource is used to take control of the system.

4.4.3.2.3 Throw System Control

Throwing system control is typically performed when a device's heartbeat is lost. When this happens, this API resource is used to notify the other user interface that it can automatically regain control of the system.

4.4.3.2.4 Get/Set Application Settings

Retrieve and update application settings.

4.4.3.2.5 Exit App/Shutdown

Sends the exit or shutdown signal to the Admin Service.

4.5 Actuator Interface

Figure 29:
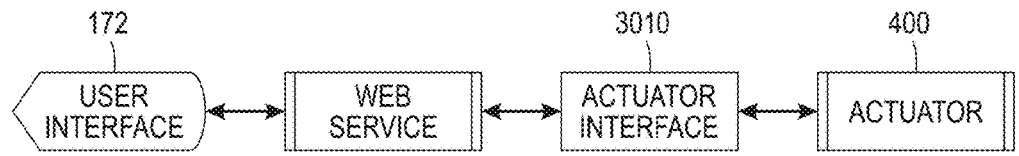

The Actuator Interface (AI) 3010 serves as the integration point between the Web Service and the Actuator. This integration is effectively the processing center where requests and their responses between the User Interfaces and the Actuator are encoded and decoded as they are relayed through the Web Service. FIG. 29 depicts the Actuator Communications Relay

4.5.1 Development Configuration

The AI may be written in C# using the Microsoft .NET 4.5 Framework. It is compiled as a library (DLL) and referenced by the Web Service.

4.5.2 Command Packets

Requests and responses are sent in the form of commands, comprising a header section followed by an optional data component. Together, the two components form a datagram package. For the packet formats the following applies:

Header Format:

Data Format:
- The data section may include information sent to, as well as received from, the Actuator
- The data section includes both read and write areas
- The data section comprises a fixed length, which is always sent in its entirety
- A command packet does not always contain a data section

4.5.3 Control Loop

Figure 30:
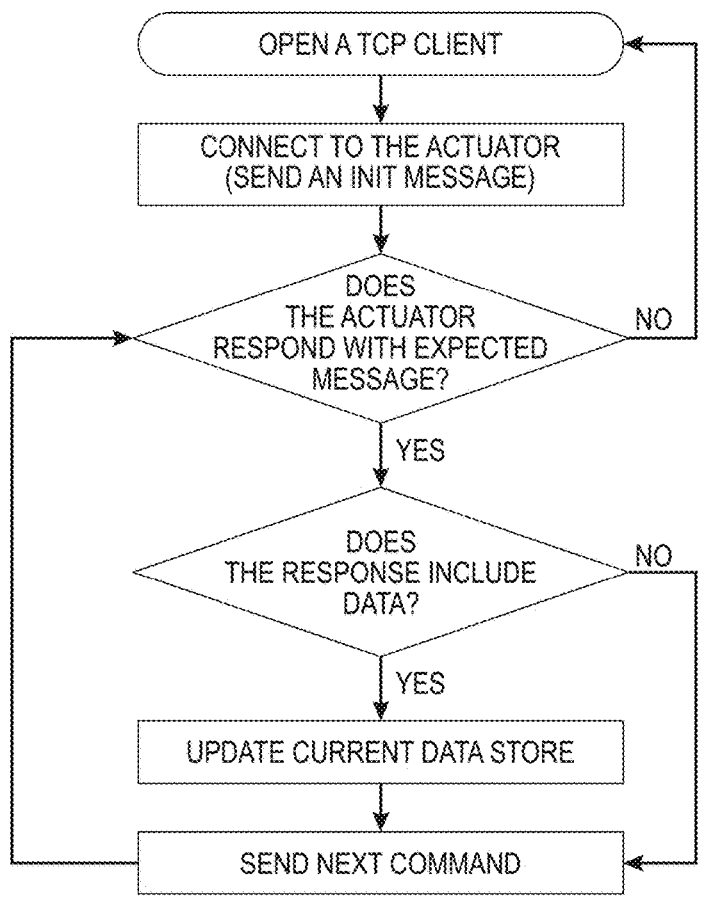
Figure 31:
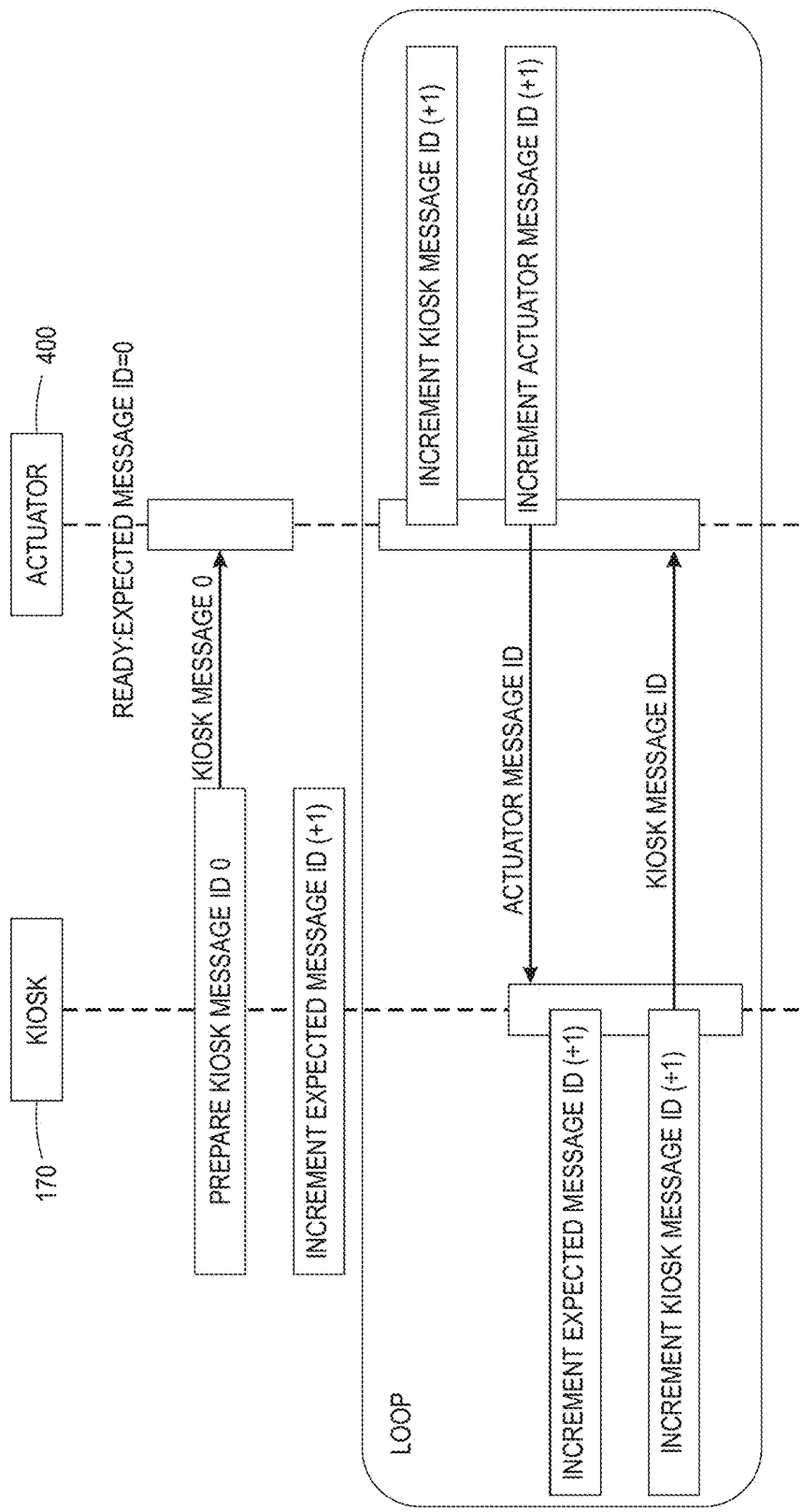

Upon initial communication with the Actuator 400, this interface establishes and maintains consistent communications with the Actuator, as depicted in detail in FIGS. 30-31. Note that the detail of the handling of special case commands, such as the Shutdown command, is not depicted in the figure.

4.5.3.1 System Heartbeat

As mentioned above (see section "Safety Considerations"), a system heartbeat is required for the various user-interfacing software components to remain active. The AI is responsible for initiating and maintaining the system heartbeat after initial communications with the actuator have been established.

To affect this heartbeat, the last good command (without data, if applicable) must be resent to the actuator at intervals of at most two (2) seconds.

4.5.4 Actuator Interface Functions

The Actuator is capable of many actions, of which the Kiosk and Remote user interfaces will only utilize a small subset. Actuator commands and capabilities include the following subset of commands used within this system:

4.5.4.1 Interrogate
Test network connectivity with actuator.

4.5.4.2 Connect
Create network connection with actuator and initiate heartbeat.

4.5.4.3 Disconnect
Stop heartbeat with actuator and terminate network connection.

4.5.4.4 Reset
Reestablish network connection and heartbeat with actuator.

4.5.4.5 StopAll
Send "stop all" command to actuator.

4.5.4.6 Move
Send directional move command (velocity mode) to actuator.

4.5.4.7 Stop
Send directional stop command (velocity mode) to actuator.

4.5.4.8 GetStatus
Retrieve overall status information: connectivity, settings, mode, and task status information.

4.5.4.9 GetVersion
Retrieve the actuator version information.

4.5.4.10 GetSerialNumber
Retrieve the actuator serial number.

4.5.4.11 BeginTask
Send the start task command (float mode) to actuator.

4.5.4.12 EndTask
Send the stop task command (float mode) to actuator.

4.5.4.13 EnableFloatMode
Toggle float mode enabled state.

4.5.4.14 EnableDescentLimit
Set descent limit enabled state in float configuration.

4.5.4.15 SetRepetitionLowerLimit
Send repetition lower limit "set" command to actuator.

4.5.4.16 SetRepetitionUpperLimit
Send repetition upper limit "set" command to actuator.

4.5.4.17 SetDescentLimitHeight
Set descent limit height in float configuration.

4.5.4.18 SetBodyWeightSupport
Set body weight support value in float configuration.

4.5.4.19 SetDfpSensitivity
Set DFP sensitivity level (high, medium, low) in float configuration.

4.5.4.20 ApplyBoost
Send boost command to actuator.

4.5.4.21 ClearError (or warning)
Clear the last error or warning flags.

4.5.4.22 ClearFall
Clear the last fall flag.

4.6 Database

Primary keys will be denoted with PK. Foreign keys will be denoted with FK. If a primary key cluster exists, multiple fields will be denoted with PK. All fields are required unless specified as "optional."

4.6.1 Configuration

ApplicationParameter

| Field | Datatype | Notes |
| --- | --- | --- |
| ParameterId | string | PK |
| Description | string | |
| DefaultValue | string | |

Site

| Field | Datatype | Notes |
| --- | --- | --- |
| SiteId | integer | PK (identity) |
| ShortName | string | unique |
| DisplayName | string | unique |

SiteParameter

| Field | Datatype | Notes |
| --- | --- | --- |
| SiteId | integer | PK, FK |
| ParameterId | string | PK, FK |
| Value | string | |

4.6.2 User Management

UserProfile

| Field | Datatype | Notes |
| --- | --- | --- |
| UserId | integer | PK (identity) |
| UserName | string | unique |
| Email | string | unique |
| FirstName | string | |
| LastName | string | |
| Title | string | optional |
| Disabled | boolean | |

4.6.2.1 .NET SimpleMembership Supporting Tables

SimpleMembership utilizes the default, auto-generated tables to complement the User Profile table. These tables are not described in detail, as they are the standard schemas provided by the .NET Framework: webpages_Membership; webpages_Roles; webpages_UserInRoles; andwebpages_OAuthMembership.

4.6.3 Patient Management

The following table tracks patient profiles.

Patient

| Field | Datatype | Notes |
| --- | --- | --- |
| PatientId | integer | PK (identity) |
| FirstName | string | |
| LastName | string | |
| DateOfBirth | date | |
| Gender | string | |
| Height | real | inches |
| Weight | real | pounds |

The following tables will support all the optional patient fields in the user interface.

PatientAttribute

| Field | Datatype | Notes |
| --- | --- | --- |
| AttributeId | string | PK |
| Description | string | optional |

PatientAttributeValue

| Field | Datatype | Notes |
| --- | --- | --- |
| PatientId | integer | PK, FK |
| AttributeId | string | PK, FK |
| Value | string | I |

4.6.4 Session Management

Session

| Field | Datatype | Notes |
| --- | --- | --- |
| SessionId | integer | PK (identity) |
| PatientId | integer | FK |
| UserId | integer | FK |
| StartTime | datetime | optional |
| EndTime | datetime | optional |

SessionTask

| Field | Datatype | Notes |
| --- | --- | --- |
| SessionTaskId | integer | PK (identity) |
| SessionId | integer | FK |
| TaskId | integer | FK |
| UserId | integer | FK |
| StartTime | datetime | optional |
| EndTime | datetime | optional |
| TimeGoal | real | optional |
| DistanceGoal | real | optional |
| RepetitionsGoal | int | optional |
| Notes | string | optional |

4.6.5 Task Management

Task

| Field | Datatype | Notes |
| --- | --- | --- |
| TaskId | integer | PK |
| Name | string | unique |
| Category | string | |
| Description | string | optional |
| HasDistance | boolean | |
| HasRepetitions | boolean | |

TaskMetric

| Field | Datatype | Notes |
| --- | --- | --- |
| MetricId | string | PK |
| Label | string | |
| Description | string | optional |

| TaskMetricValue | | |
|---|---|---|
| Field | Datatype | Notes |
| SessionTaskId | integer | PK, FK |
| MetricId | string | PK, FK |
| Value | real | |

4.6.6 Logging

| Log (log4net) | | |
|---|---|---|
| Field | Datatype | Notes |
| Id | integer | PK |
| Timestamp | string | |
| Thread | string | |
| Level | string | |
| Logger | string | |
| Message | string | |
| Exception | string | |

4.7 User Interface 4.7.1 Kiosk

The Kiosk user interface application is an AngularJS web application hosted locally on the kiosk laptop. AngularJS is a Javascript MVC framework used for building client-side web applications (apps that live in the browser). A typical AngularJS application is composed of HTML, CSS, images, and JavaScript files. The web application communicates with a locally hosted .NET 4.5 Web API responsible for the entire system's backend support. The Kiosk user interface is also supported by a Windows service responsible for handling the exit and shutdown requests from the user interface. Exemplary illustrations for the interface screens are depicted in FIGS. 32-56.

4.7.2 Remote

The remote user interface may be the same web application used for the Kiosk, with any deviations being strictly within the user interface components (i.e., the screens may not look identical). To achieve this, a separate set of Remote views (a.k.a. screens) is enabled within the web application when the Remote device is detected. From a functionality perspective, the Remote application utilizes the same controlling logic as the Kiosk. Cordova may be used to package the AngularJS web application as a native Android application.

4.7.3 Sitemap

The following sitemap is provided as a snapshot to the user interface design which was used to create the end-user applications for both the Kiosk and Remote. The associated figure numbers for each of the user interface screens/functions are provided.

Figure 32:
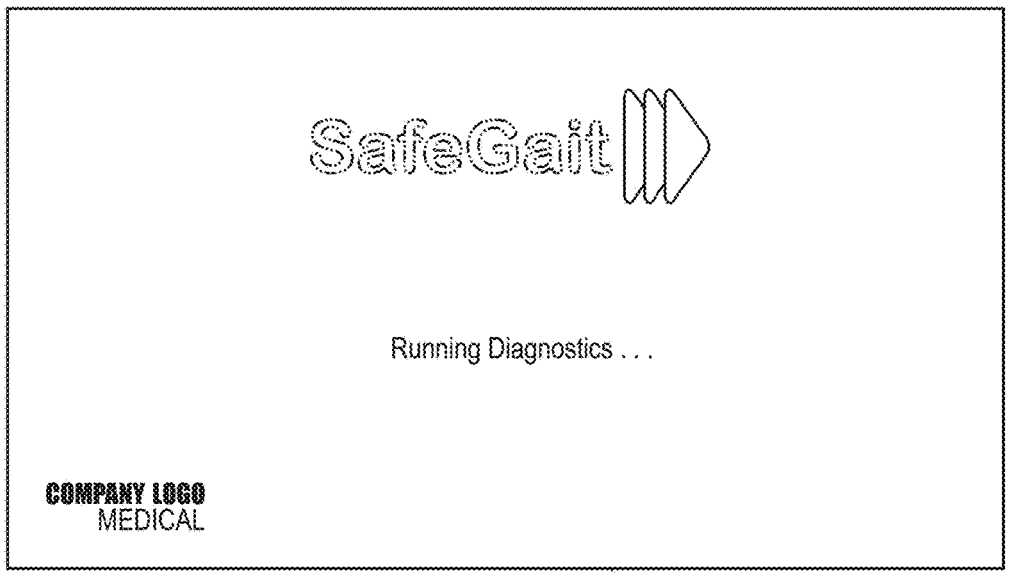
FIGS. 32-56 are illustrative screenshots for several features of the system that are available via embodiments including an interface such as the kiosk and/or remote application interfaces.
Figure 33:
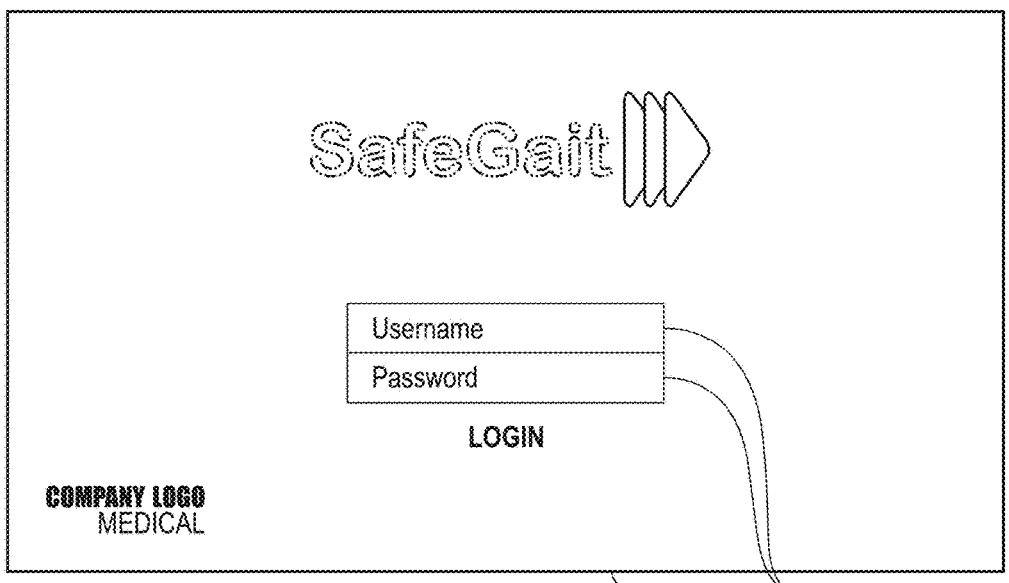
Figure 34:
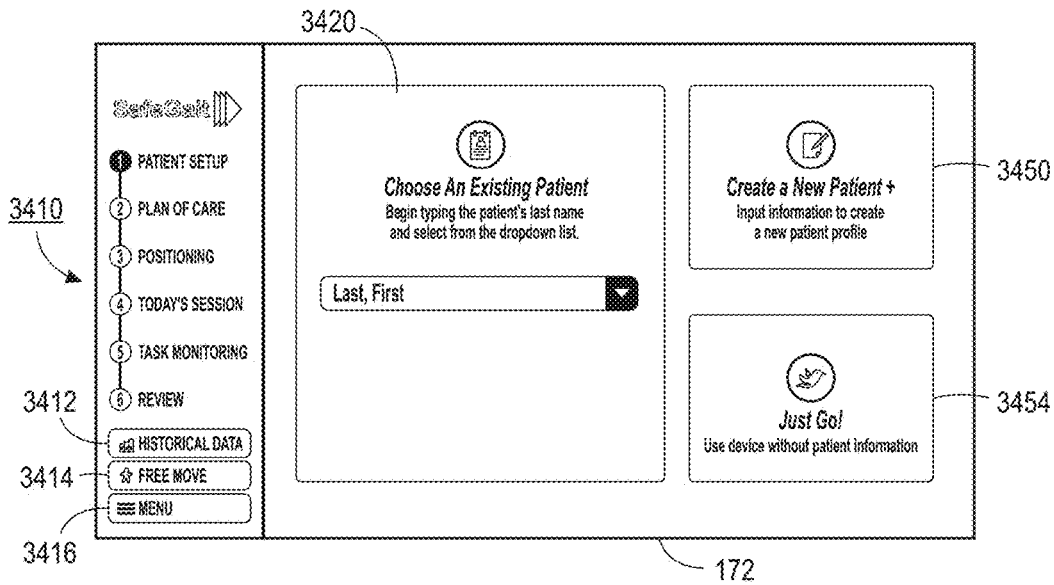
Figure 35:
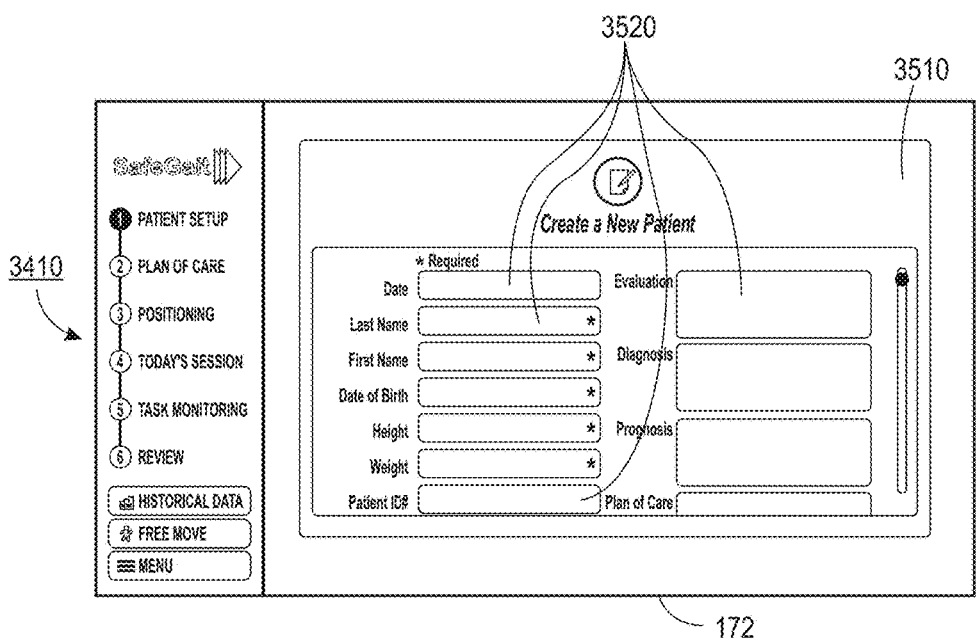
Figure 36:
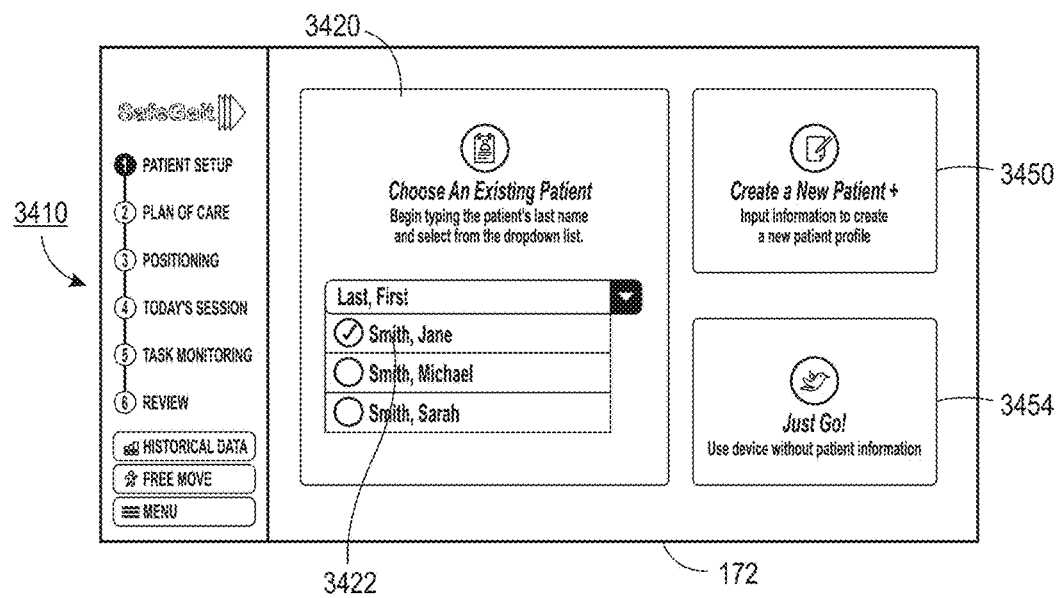
Figure 37:
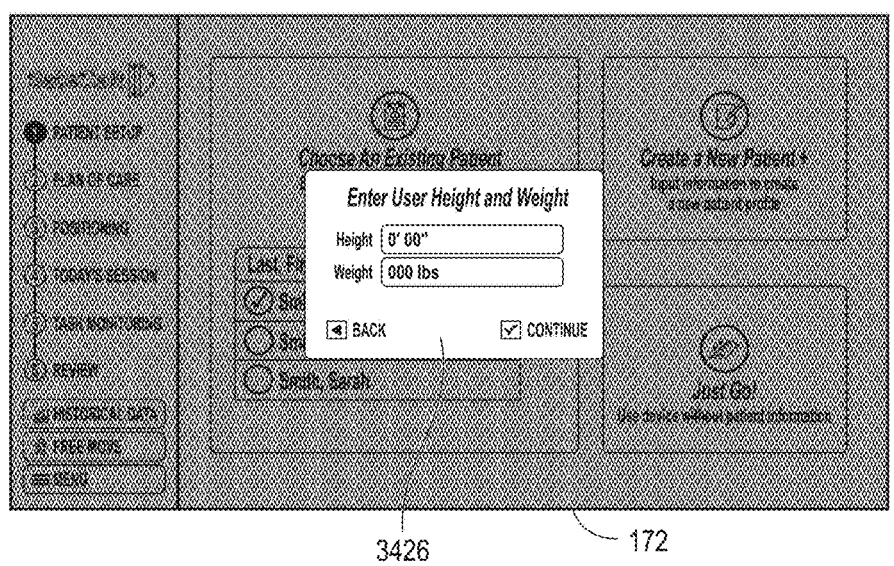
Figure 38:
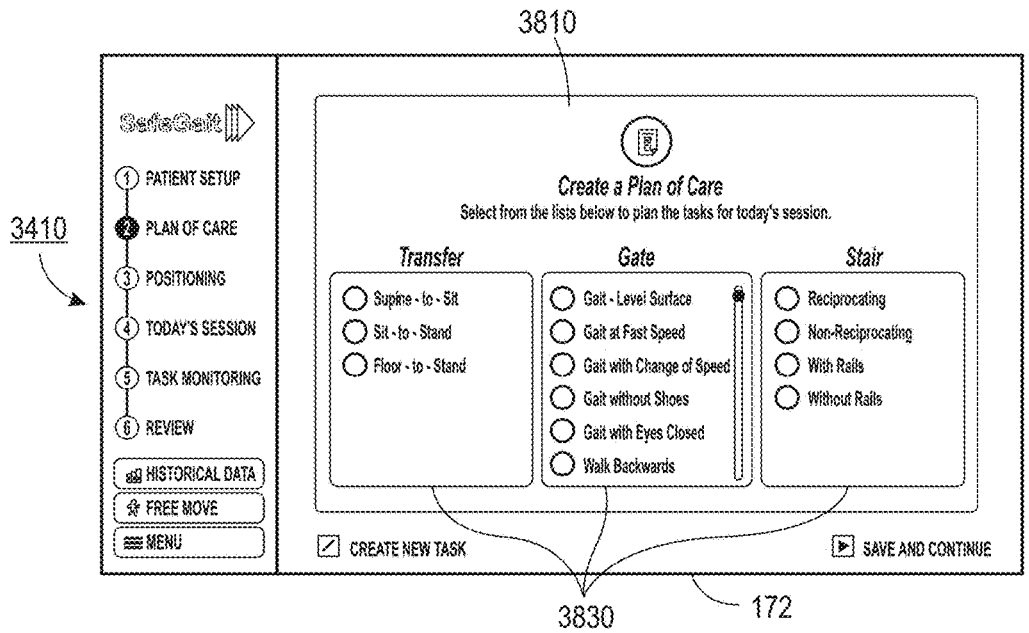
Figure 39:
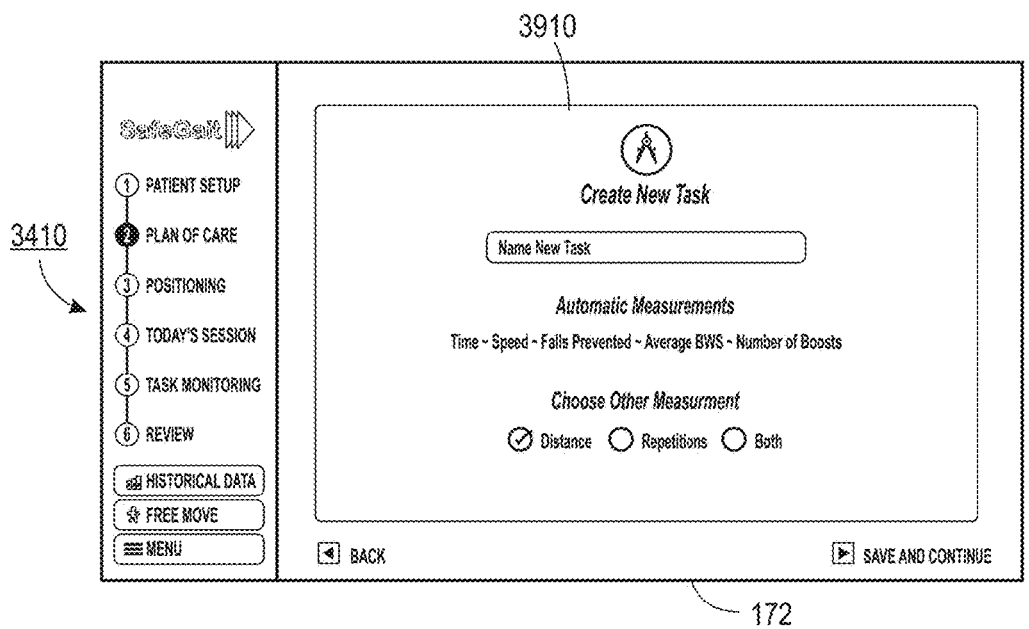
Figure 40:
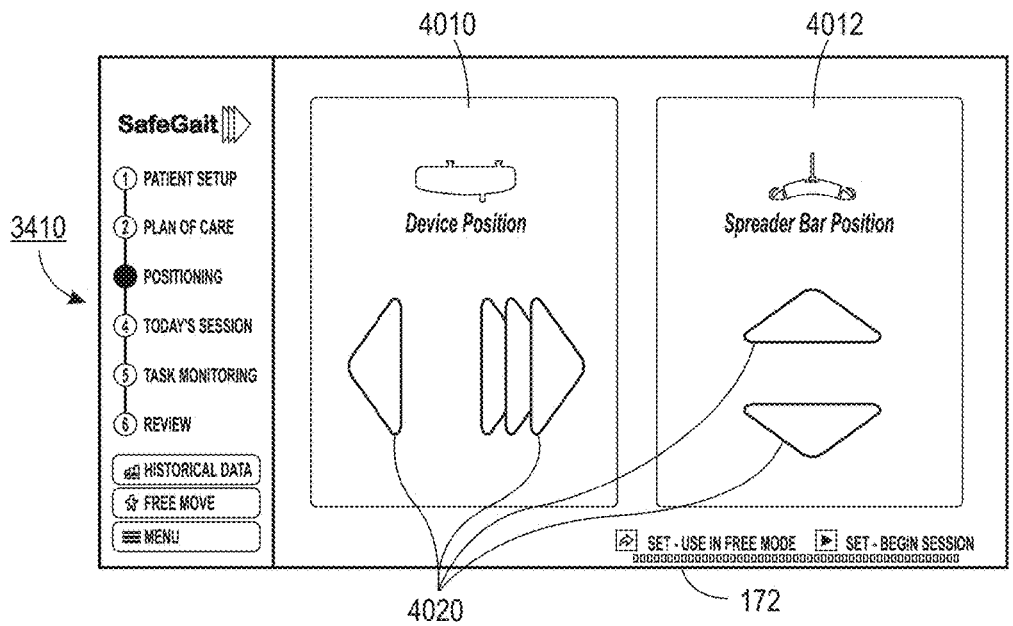
Figure 41:
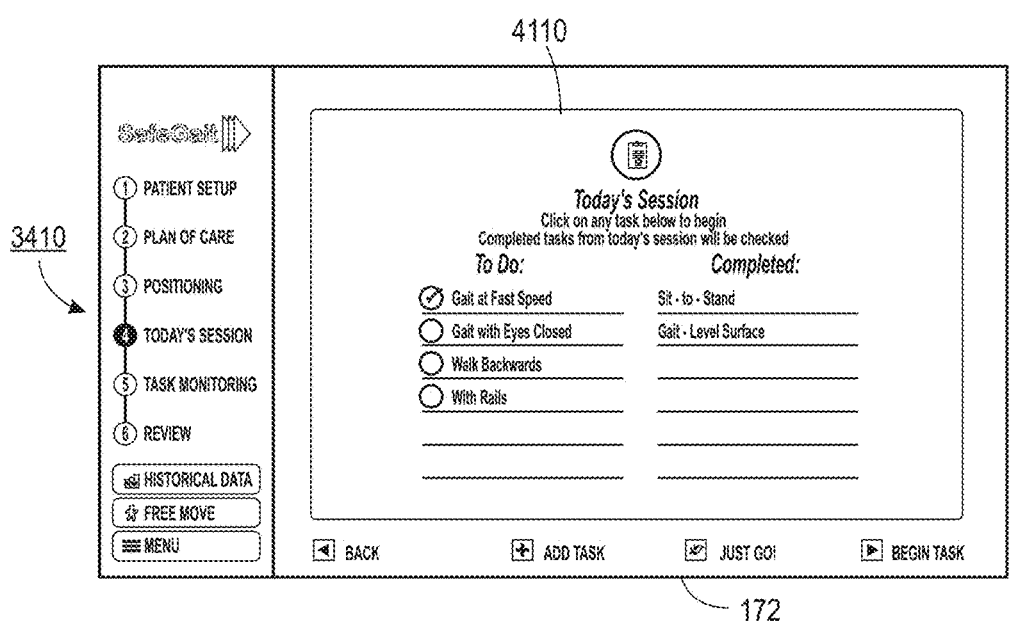
Figure 42:
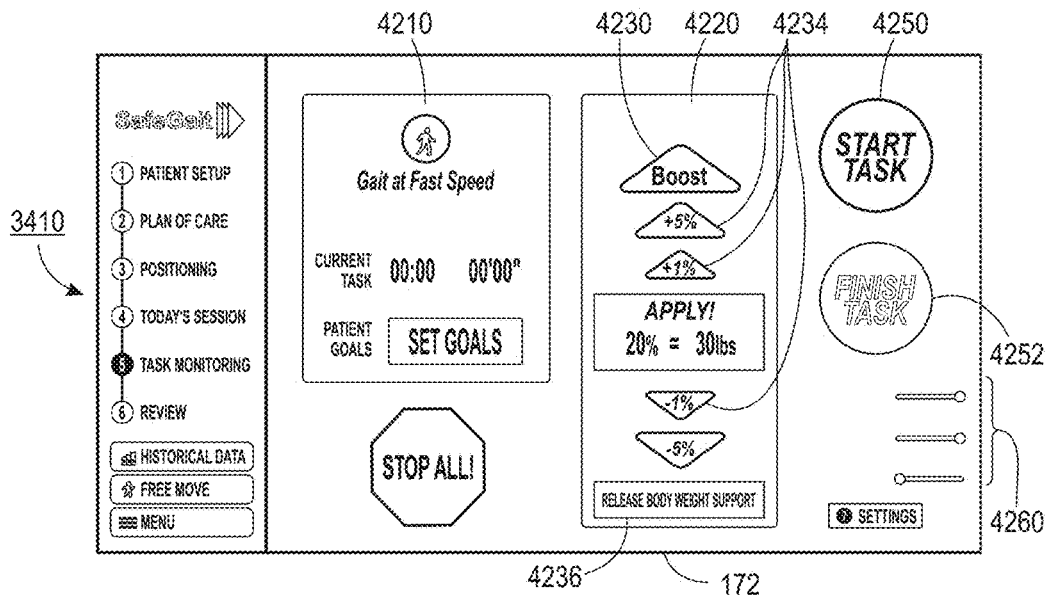
Figure 43:
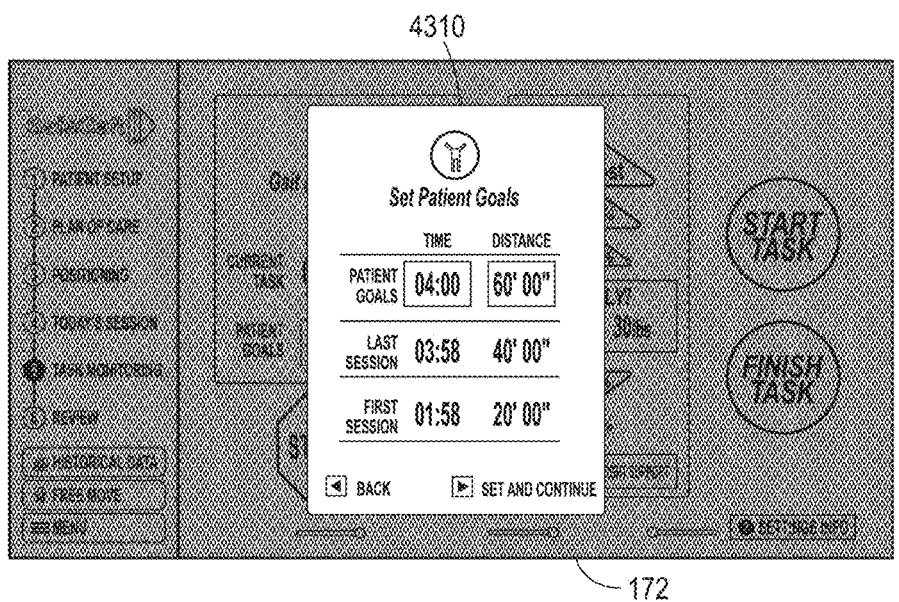
Figure 44:
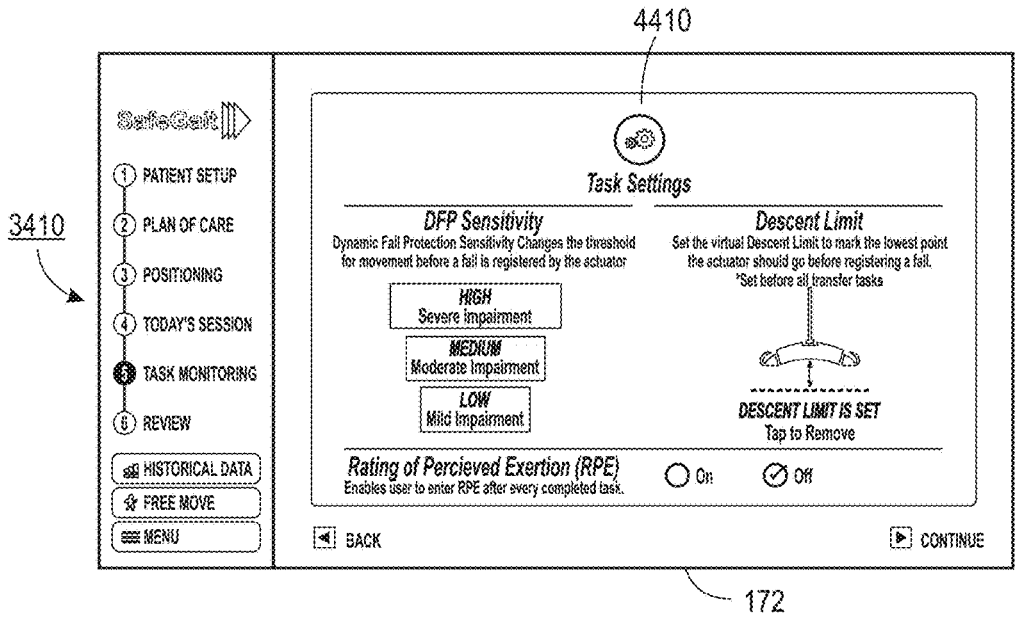
Figure 45:
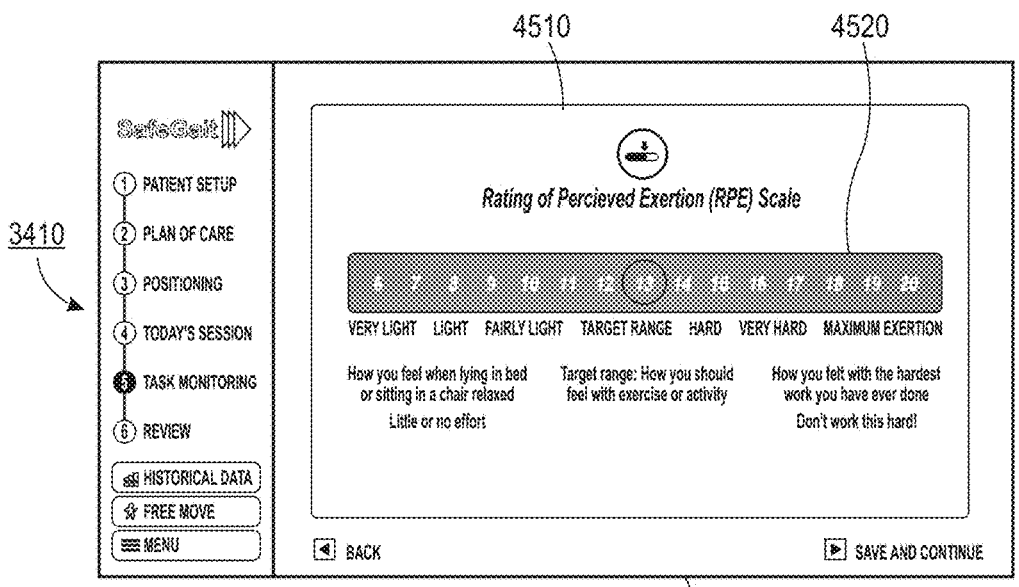
Figure 46:
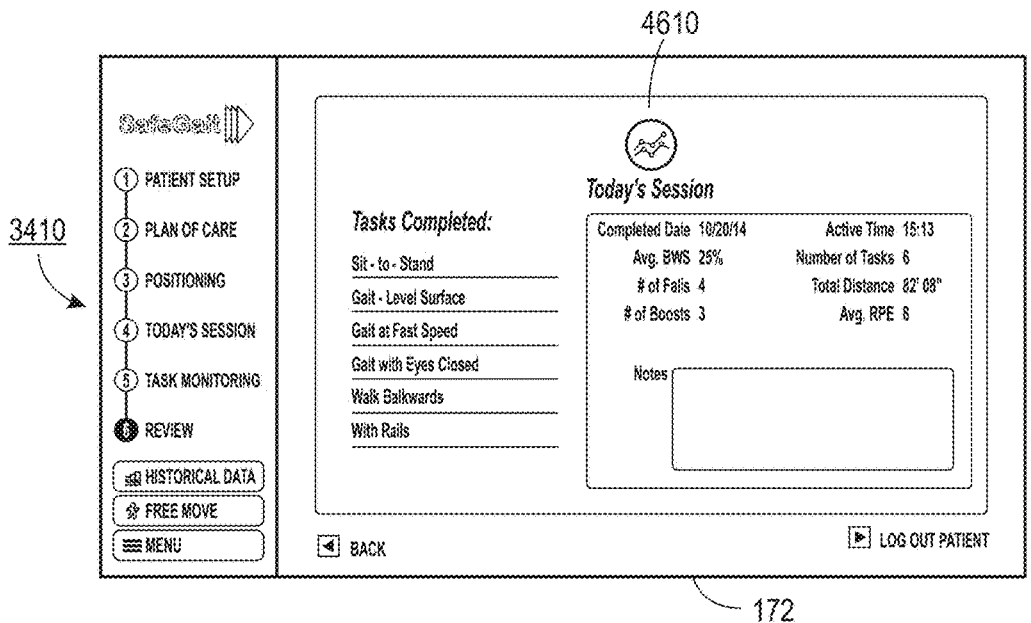
Figure 47:
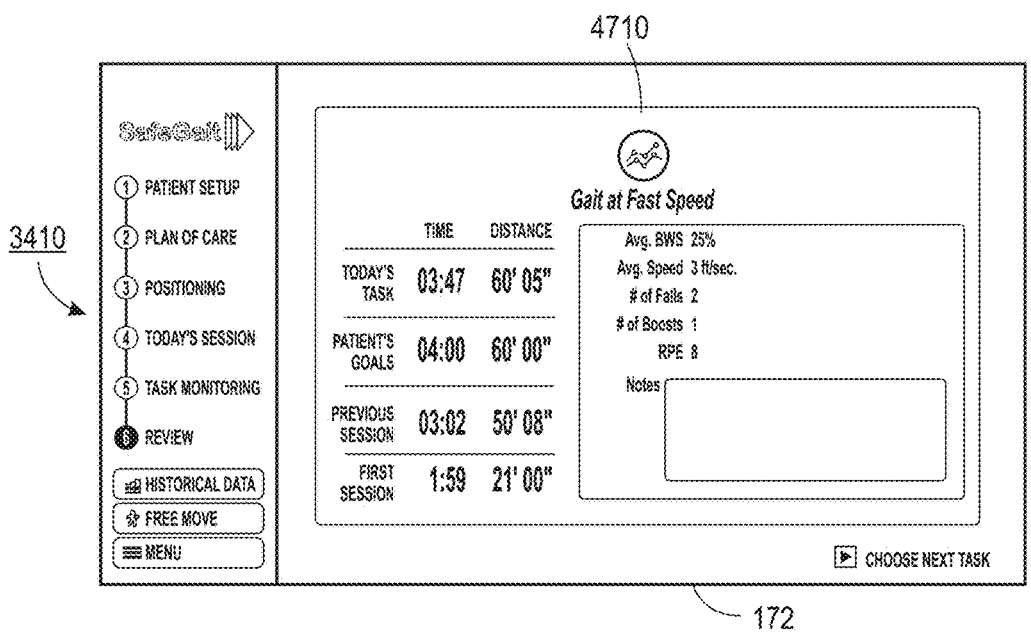
Figure 48:
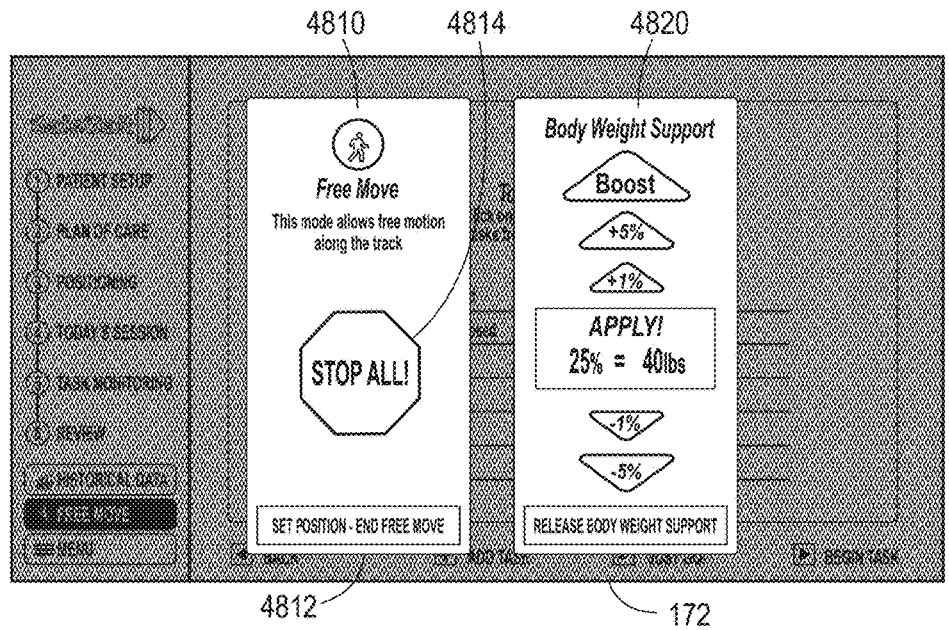
Figure 49:
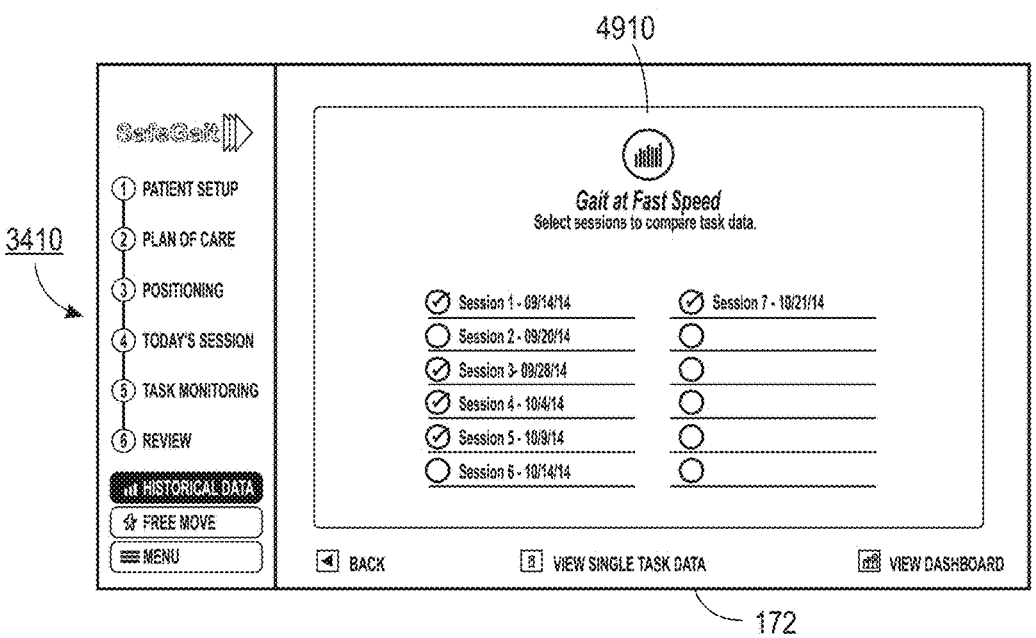
Figure 50:
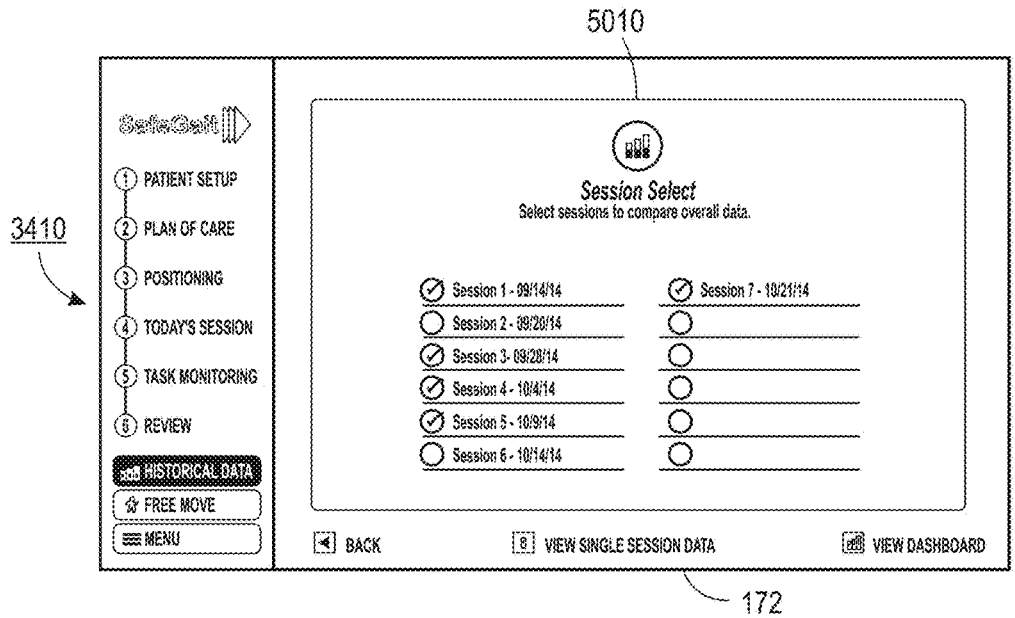
Figure 51:
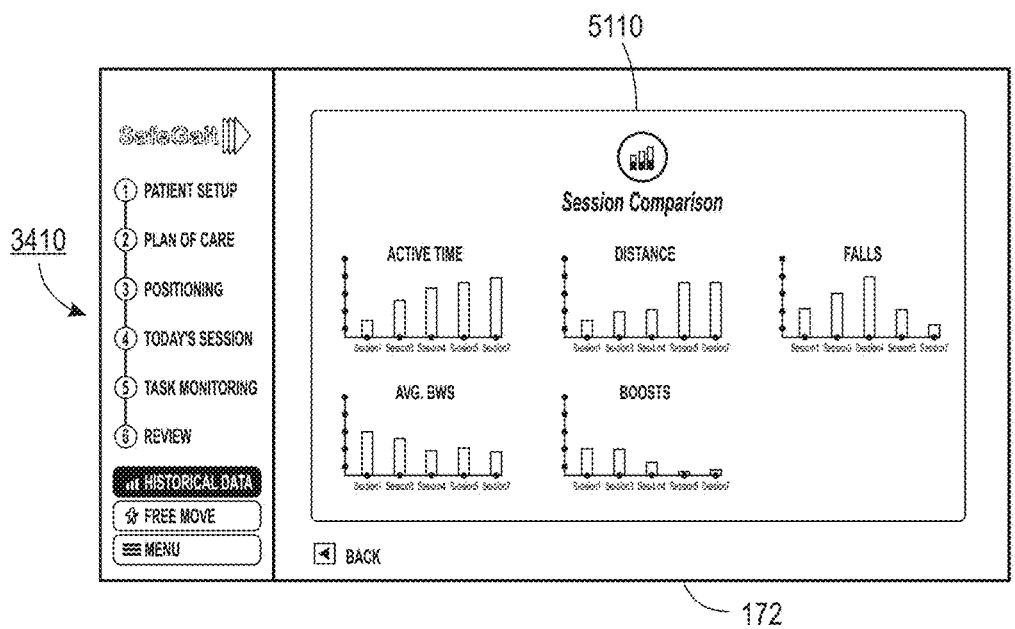
Figure 52:
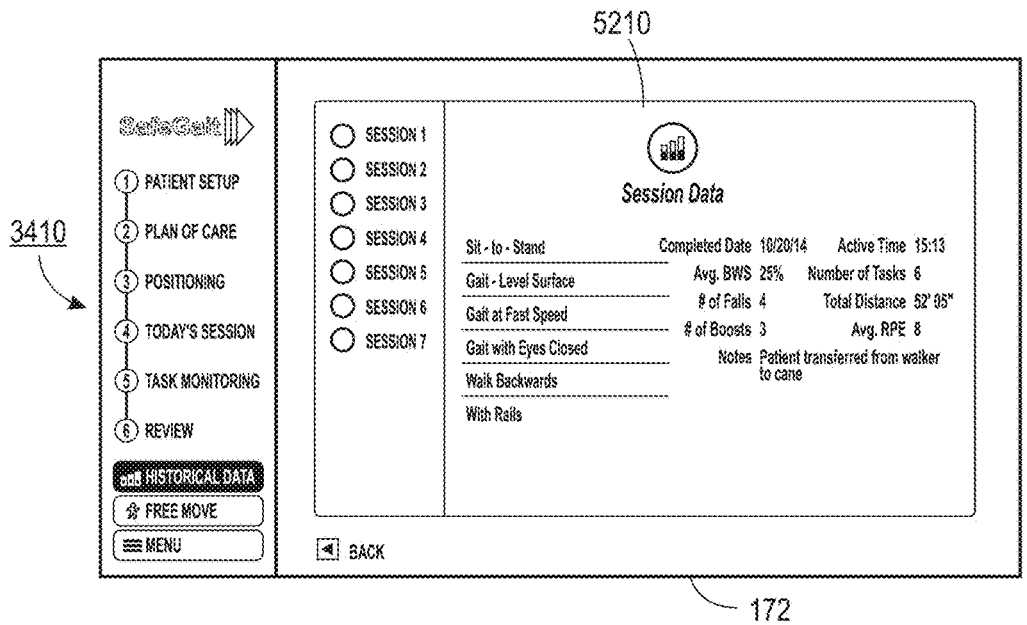
Figure 53:
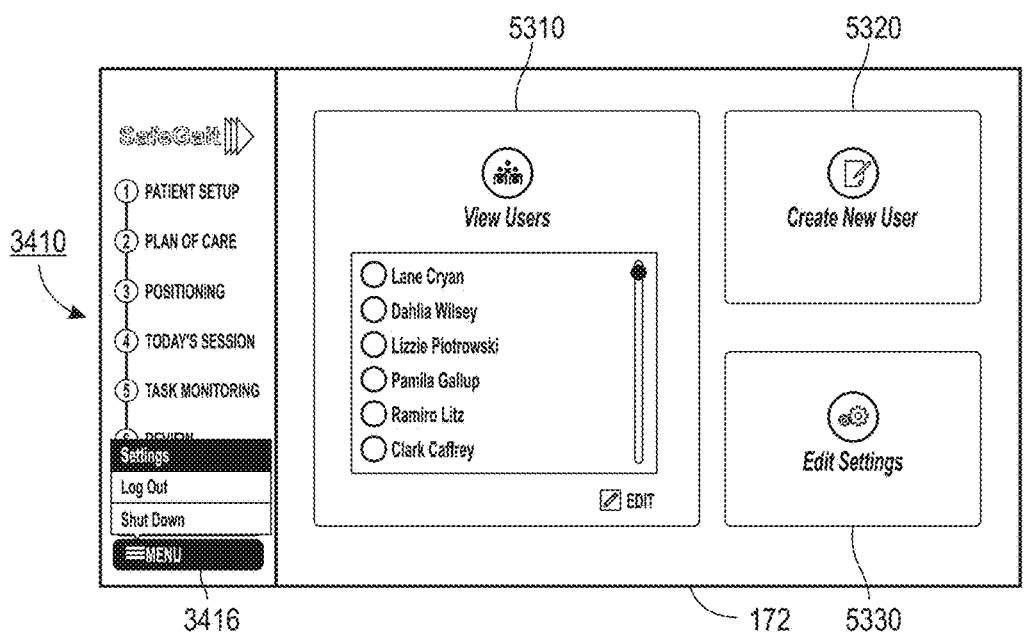
Figure 54:
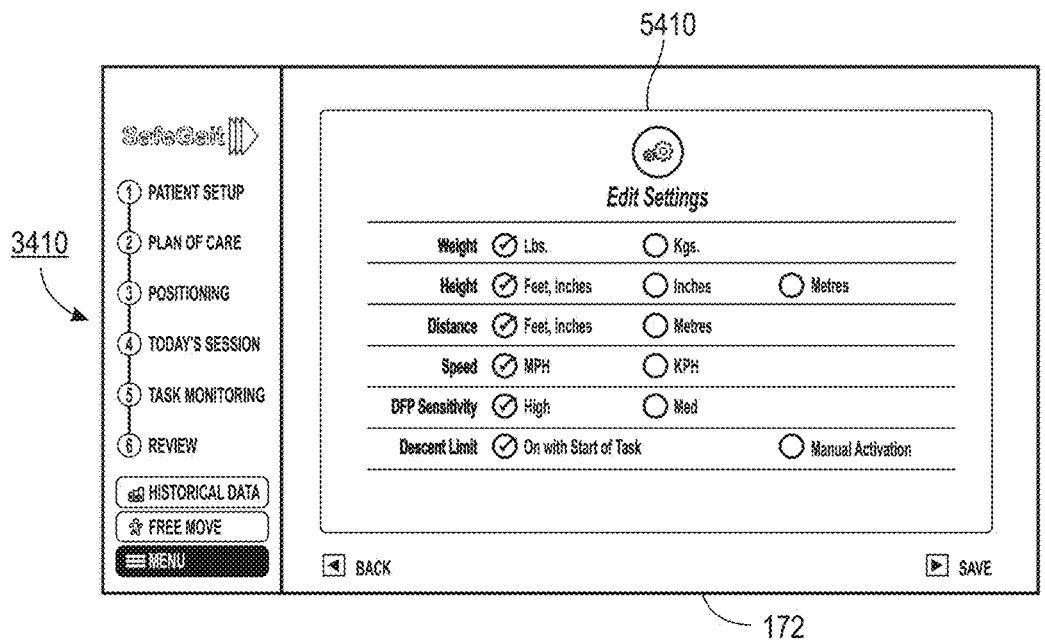
Figure 55:
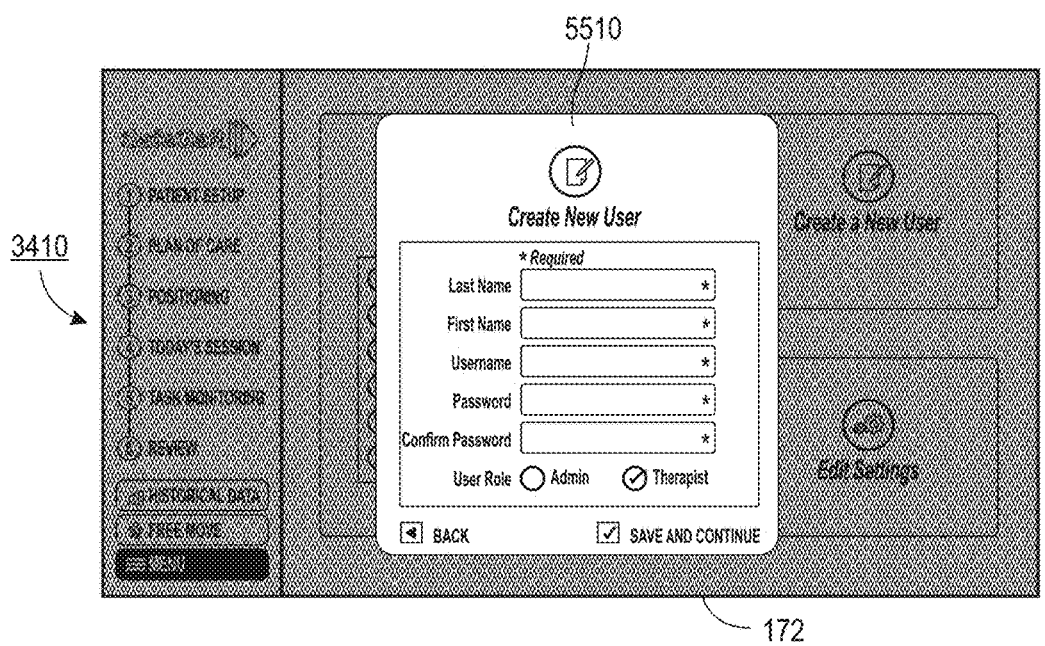
Figure 56:
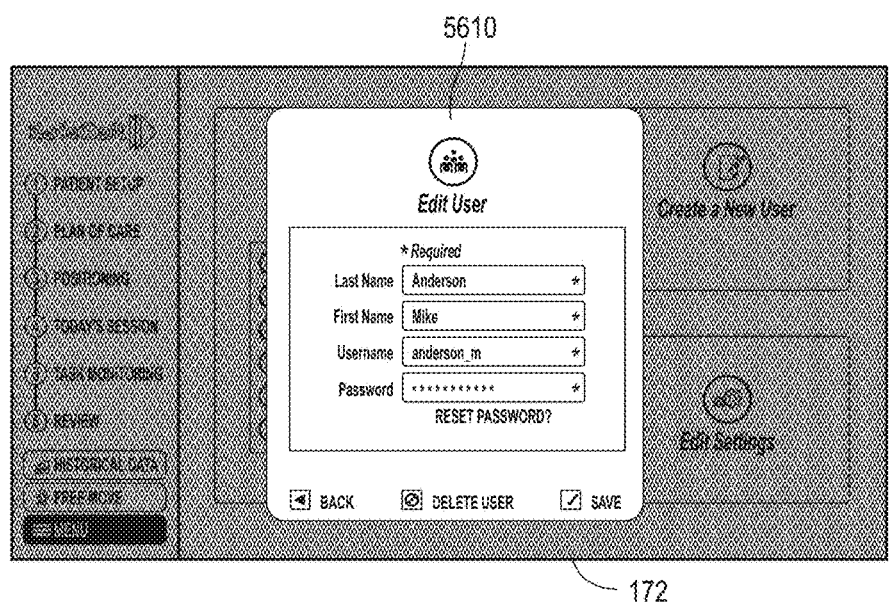

- 4.7.3.1 Startup—FIG. 32, the user interface 172 shows the status of the system during a start-up process;
- 4.7.3.2 Login—FIG. 33, in the user interface screen 172, username and password fields 3310 are provided for the user to enter data in order to log in to the system;
- 4.7.3.3 Patient Setup—FIG. 34, the user interface screen provides a navigational region 3410 on the left side to show a sequence of operations relative to a patient, as well as buttons to access data (3412), directly operate the actuator (3414), or display a menu (3416; also see FIG. 53); in the middle of the display is a field 3420 from which to enter/select a patient by name or other form of identification (e.g., patient ID number), and buttons 3450 to select new patient creation, or 3454 to just start a task without patient data;
- 4.7.3.3.1 New Patient—FIG. 35, in response to the selection of Creat New Patient 3450, the display of a patient information entry screen 3510 and related fields 3520 is facilitated on the interface 172, and once entered the data can be saved via button 3550 in the lower right corner of the interface;
- 4.7.3.3.2 Select Patient (Confirm Height & Weight)—FIG. 36, in combination with FIG. 37, illustrates a drop-down menu 3422 that facilitates the selection of an existing patient from the database records, and the selection may be followed by the presentation of one or more display windows 3426 that facilitate the entry of a patient's height and weight so that the information may be recorded in the database as well as used to facility setting of one or more of the system variables (e.g., limits, body weight support, boost, etc.);
- 4.7.3.3.3 Just Go (Confirm Height & Weight)—FIG. 37, as discussed above, provides an illustration of the patient height and weight entry window so that information can be input for either an identified patient or in response to the "Just Go" selection (3454) of FIG. 34;
- 4.7.3.4 Plan of Care—provides screens so that a therapist can develop a plan of care for the patient using the system;
- 4.7.3.4.1 Select Tasks—FIG. 38 provides the Plan of Care display window 3810, and includes fields and/or menus 3830 that facilitate the selection of particular components of a task(s) that the patient is to accomplish in the current, or a future, therapy session—where the selected components are also stored in association with the patient's record in the database;
- 4.7.3.4.2 Create Custom Task—FIG. 39 allows a user of the system to create or define a new task via window 3910 to be stored in the system database for use with one or more patients;
- 4.7.3.5 Positioning (Actuator Controller)—FIG. 40 allows the selection of arrow buttons 4020 within either window 4010 or 4012 to facilitate "manual" movement of the movable support or the strap, respectively;
- 4.7.3.6 Today's Session—provides interface screens related to a particular therapy session;
- 4.7.3.6.1 Select Task—FIG. 41 illustrates window 4110 that displays the selections for a particular therapy session and not only allows for the delection of particular tasks (left side), but also illustrates the completed tasks (right side), and the window is closed in response to one of the commands depicted along the bottom of the display in interface 172 (e.g., "Add Task" would add a task to the ToDo list;
- 4.7.3.7 Task Monitoring (Actuator Controller)—FIG. 42 is an exemplary display interface screen showing the information related to control of the actuator on the movable support, and includes display window 4210 showing a currently programmed task as well as the time and/or distance over which the task is performed, and display window 4220 that indicates the level of body weight support being supplied to the patient via the actuator and strap attached to the harness; also included in 4220 is a Boost button 4230 to facilitate a brief increase to the body weight support, buttons 4234 to adjust the level of body weight support, and button 4236 to release (0%) the body weight support feature; buttons 4250 and 4252 provide for respectively starting and stopping the programmed task, and sliding scales 4260 illustrate the setting levels for other parameters of the system;

4.7.3.7.1 Task Goals—FIG. 43 illustrates a display window 4310 that allows for the display of past patient performance metrics for the task being performed as well as setting goals for the current session 4.7.3.7.2 Actuator Settings—FIG. 44 provides a display window 4410 that permits the adjustment of machine (actuator) parameters such as dynamic fall prevention (DFP) sensitivity (low, medium, high), limits on the height (descent limit) at which the system declares the patient to be falling and triggers a stop to the descent, and means for allowing the system to track a user-entered exertion score (RPE) upon completion of each task (see FIG. 45);

4.7.3.7.3 RPE—FIG. 45 is a perceived exertion scale window 4510 and an associated selector (numeric indicator along a range bar 4520 that facilitates entry of a patient's perceived exertion level;

4.7.3.8 Review—provides the ability for the therapist or user to review particular sessions or tasks and data associated therewith;

4.7.3.8.1 Session—FIG. 46 is an exemplary illustration of a session summary display window 4610 that depicts not only the tasks completed but other information related to the therapy session;

4.7.3.8.2 Task—FIG. 47 provides a window 4710 that illustrates particular detail for each of the tasks indicated in the left side of window 4610, and thereby allows a user to scroll through the tasks and see additional information;

4.7.3.9 Free Move (Actuator Controller)—FIG. 48 is an illustrative example of a free movement display interface where the support system operates in a free movement mode 4810 and is available to provide an adjustable level of support for the patient, including button 4812 to set the position of the movable support (e.g., along a track), and Stop button 4814 and window 4820 to control the level of support like window 4220 described above;

4.7.3.10 Historical Data—provides screens by which the therapist or user can search or sort stored data within the database;

4.7.3.10.1 Select Task Filter—FIG. 49 illustrates a display window 4910 that permits the selection of particular sessions from the database for the comparison of historical performance data;

4.7.3.10.2 Select Sessions—FIG. 50 illustrates a display window 5010 that permits the selection of particular sessions from the database for the comparison of historical performance data 4.7.3.10.3 Chart Dashboard—FIG. 51 provides an illustrative example of the historical data from sessions selected in FIG. 49 in the nature of bar graphs presented in window 5110;

4.7.3.10.4 Session Details—FIG. 52 provides an illustrative example, in window 5210, of data retrieved from the database for a selected session 4.7.3.11 Manage—FIG. 53 is an exemplary representation of an interface screen 172 that permits the user to view and manage users, including not only selection of users (5310) but the creation of new users for the system (5320) and the editing of system and user settings (5330) as well as the menu associated with button 3416;

4.7.3.11.1 Application Settings—FIG. 54 is a representation of an edit setting window 5410 that would be presented in response to a user selection the edit settings operation in window 5330, and includes settings such as units and the selection of performance variables (e.g., DFP sensitivity, limits, etc.;

4.7.3.11.2 Create User—FIG. 55 is an exemplary representation of a new user creation display window 5510; and 4.7.3.11.3 Edit User—FIG. 56 is an exemplary representation of the edit user display window 5610.

4.8 Installation Packages

Installation packages may be created for the Kiosk software, which is an all-inclusive installer that manages the installation of the following software entities: WebAPI (web services); Database; Kiosk User Interface Application; A means to install the Remote software. Installation requires some configuration, and as stated previously, configuration of the Kiosk (and Remote) at the operating system level is believed to be within the scope of knowledge of one skilled in the art of programmable interface devices.

Having described the programmable user interface in accordance with an embodiment of the system, attention is returned to the general operation of the system. Although described above in relation to FIG. 1 as a rack and pinion type of indexing mechanism, it will also be appreciated that alternative methods and devices may be employed for reliably controlling the horizontal position of the support 130 relative to the track, including the friction drive mentioned and further described with respect to FIGS. 4-10.

In one embodiment, an optical receiver/transmitter pair and sensor may be employed to track the position of the support, where a sensor detects an encoded position along the track. As described in more detail, the ability to reliably control the position of the support enables the system to assure its position relative to stations or regions of the track/path (e.g., FIG. 17) are accurately determined. Accurate tracking of the movable support's position permits the potential for use of multiple units on a single track—thereby permitting a plurality of patients to use the same track simultaneously where the units can communicate with one another or with a central position control in order to assure that an appropriate spacing is maintained between adjacent units at all times. In an alternative embodiment, the individual support units themselves may include sensors or other control logic that prevents the units from coming into contact with one another while in operation.

It will be appreciated that although the horizontal position of support 130 is under the control of the horizontal drive, and the support itself otherwise freely slides or rolls along the path defined by the track 120. The support is connected to roller assembly 128 located on the interior of the track which provides rolling contact with at least the bottom interior of the C-shaped track, and the sides as well. Moreover, the interior of the track may be any conventional track, including a single piece of track or a collection of multiple pieces (e.g., oriented end-to-end). The track may also have electromechanical contacts therein (not shown) that are available to provide electrical power and/or signals to the drives and/or control mechanisms associated with the support. In other words, the roller assembly provides a means for operatively attaching the support to the track, yet minimizing friction using the associated roller assemblies.

Figure 5:
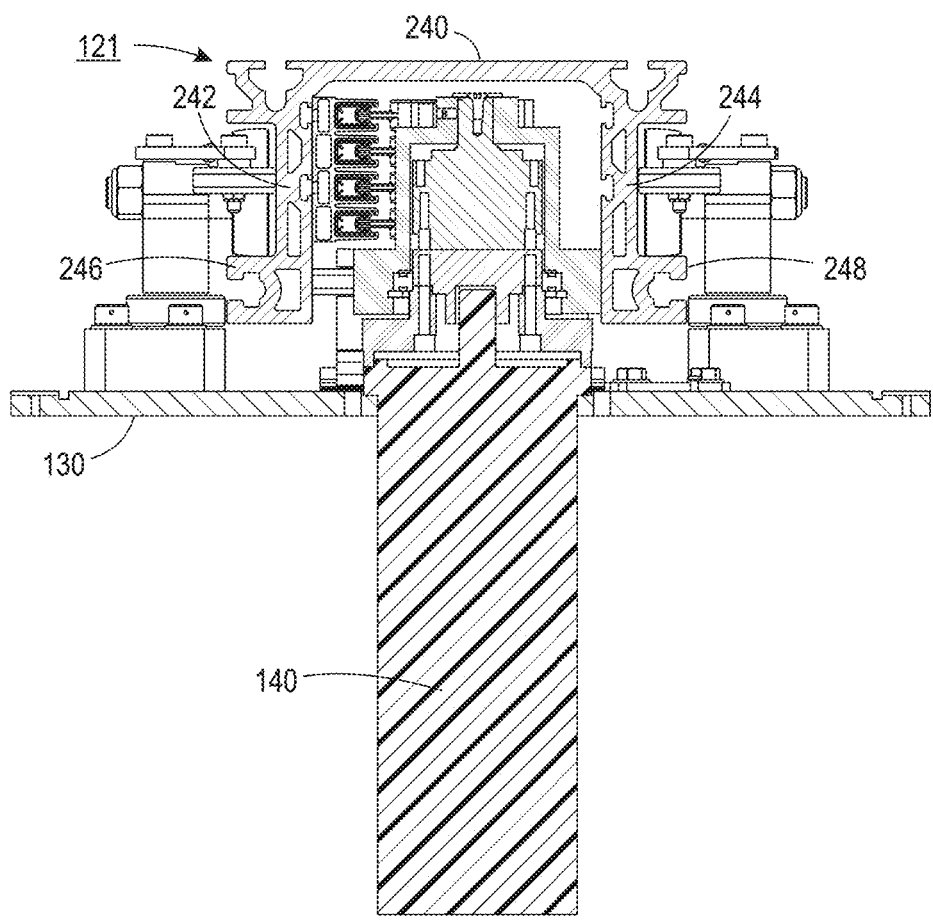
FIG. 5 is a cutaway end view along section 5-5 of FIG. 4.
Figure 6:
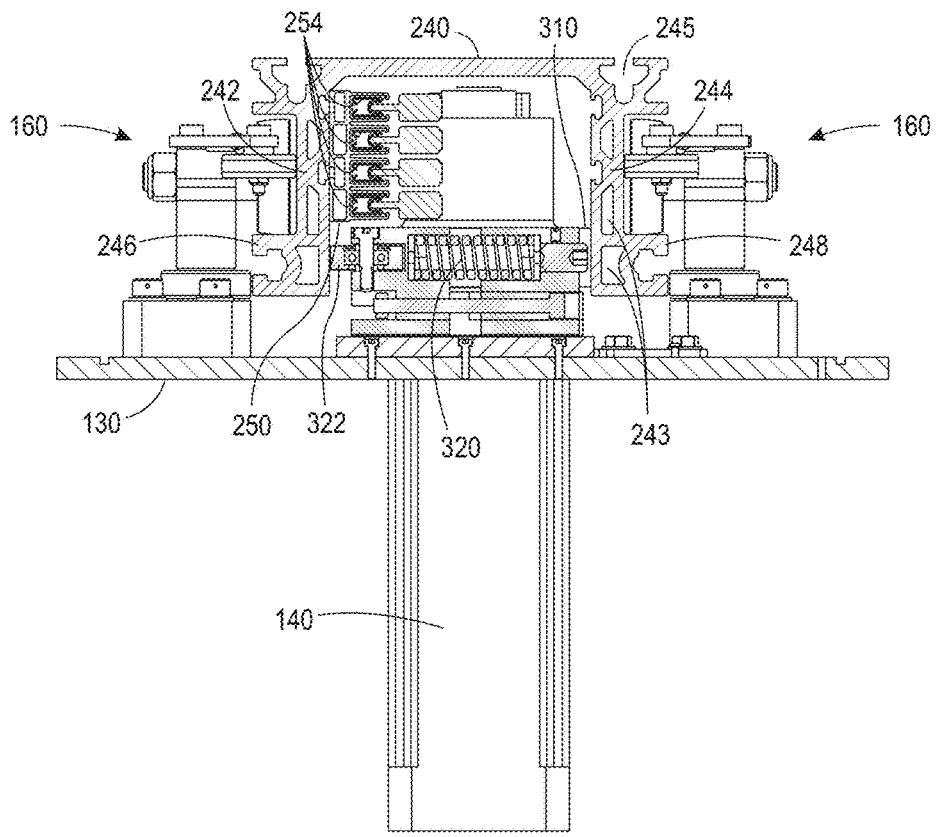
FIG. 6 is a cutaway end view along section 6-6 of FIG. 4.
Figure 7:
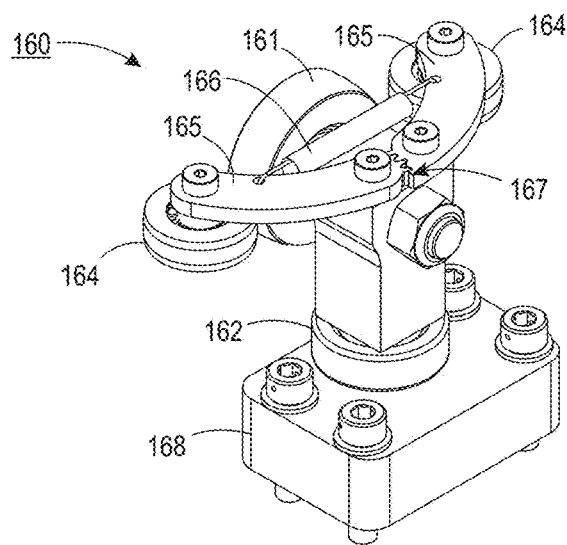
FIG. 7 is a perspective view of one of the support suspension assemblies of the embodiment of FIG. 4.
Figure 8:
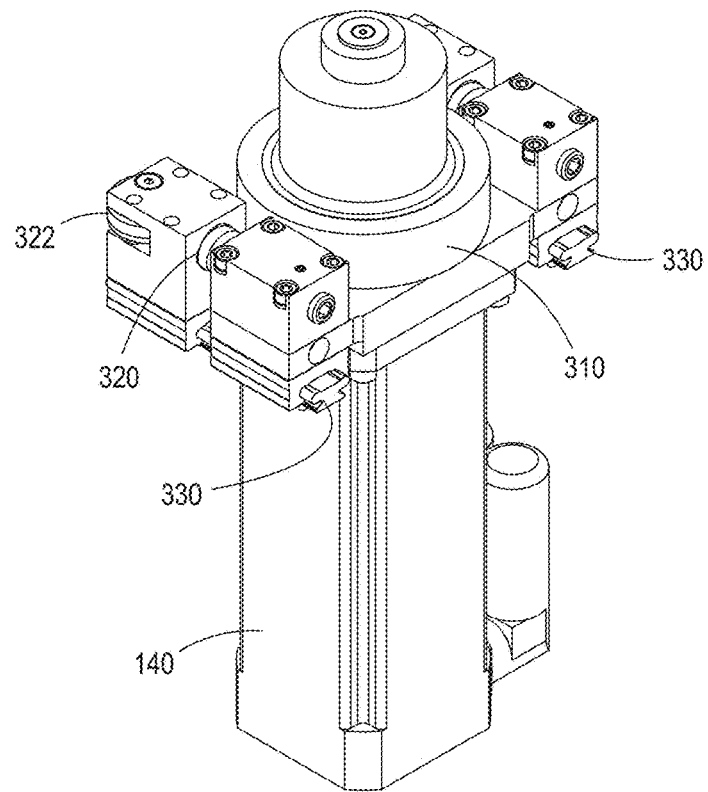
FIGS. 8 and 9 are, respectively, perspective and top views of the frictional horizontal drive of the embodiment of FIG. 4.
Figure 9:
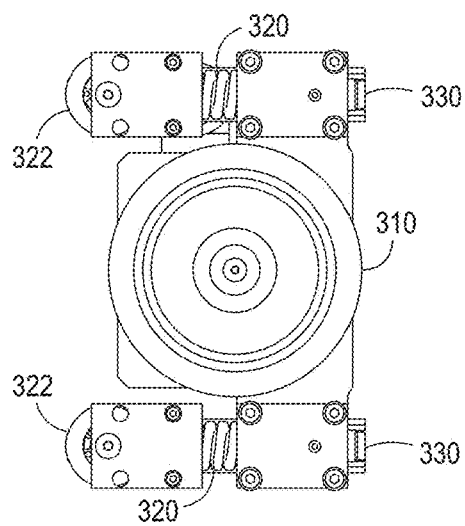

In an alternative configuration such as that depicted in FIGS. 4-10, the components of the system are modified to provide a track where support is provided on the exterior of the track and the drive and power interfaces are located on the interior surfaces of the track. As illustrated, for example in FIGS. 4-6, the alternative track 121 comprises an assembly of a plurality of extruded members joined end-to-end. The track cross-section is illustrated in FIGS. 5 and 6 which show, respectively, sectional views 5-5 and 6-6 of FIG. 4.

The track includes a generally planar upper web or surface 240, extending in a longitudinal direction. From the upper web 240, opposing sides 242 and 244 extend in a downward directed along each side of the upper web. The combination the upper surface and downward-extending sides form the interior portion of the track 121. Each of said opposing sides further includes a shoulder 246, 248, respectively, extending in an outward direction therefrom, where the shoulders are oriented perpendicular to the respective side. As further illustrated in the cross-sections, the track includes one or more enclosed channels 243 extending the entire length of each of the downward-extending sides, where the channels reduce the weight and increase the rigidity of the track section. The track sections may further include at least one T-slot 245 suitable for the insertion of a mounting component (e.g., screw or bolt head) therein to facilitate installation and suspension of the track from a ceiling or similar structure. Although not depicted, the track sections are designed to be connected end-to-end using studs or similar splicing members (e.g., a cam-lock splice) that span from the end of one member to the adjoining end of the next track member.

Figure 10:
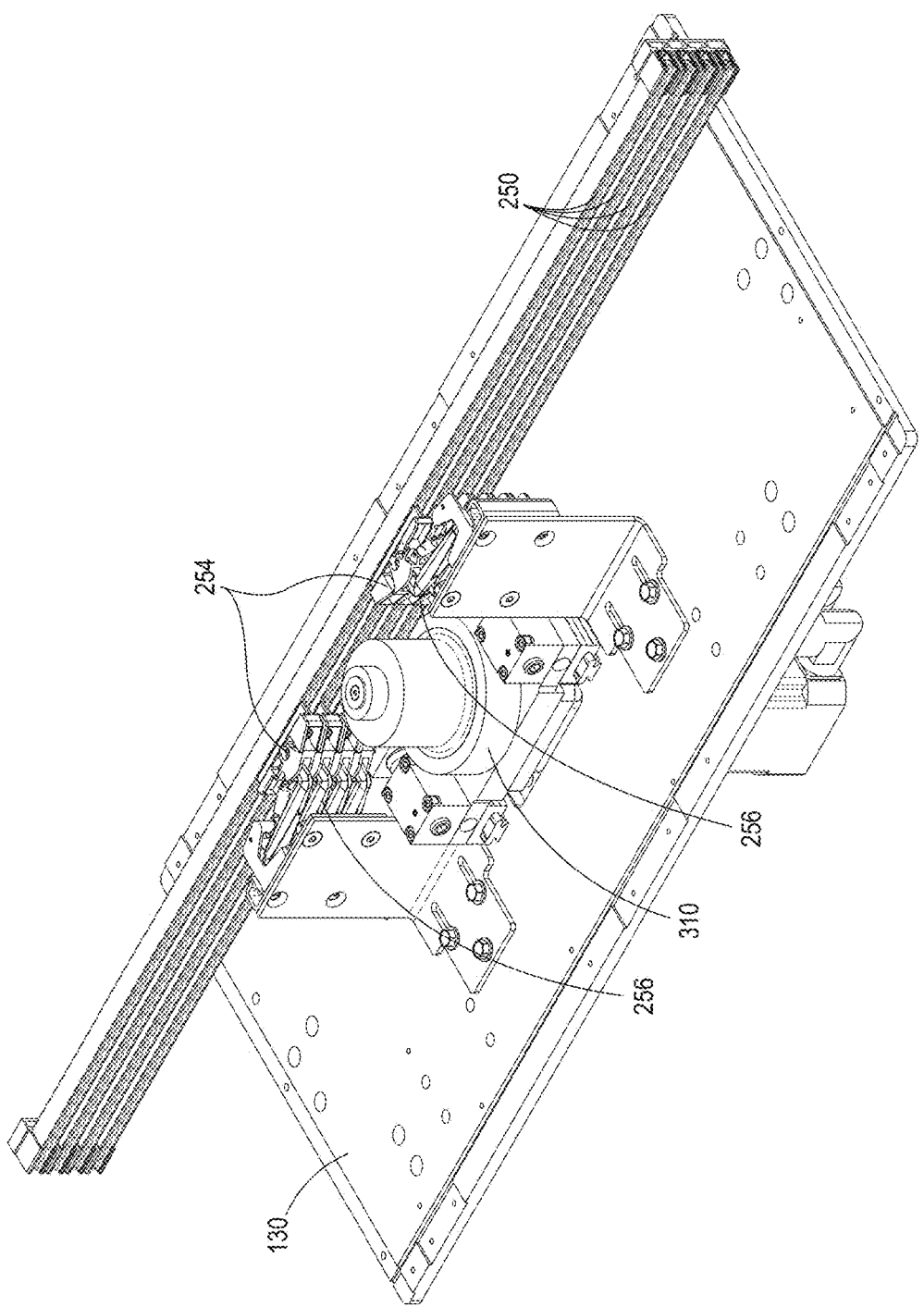
FIG. 10 is a perspective view of the embodiment of FIG. 4, including components on the interior of the track.

Multiple electric or power rails 250 are spaced along an interior portion of the track along one of the interior sidewalls for each portion of track over which the movable support unit travels. The rails are mounted to the track using insulated standoffs that are attached via internal T-slots provided in the interior of the track sides. Power is transferred from the rails to the control system and motors via one or more shoes 254 that are slidably engaged with the rails, and associated cabling, to ensure power is available. As illustrated in FIG. 10, for example, two shoe assemblies 256 and associated support structures are employed in the system in order to assure continuity of power as the movable support unit 104 travels along the track.

Referring also to FIGS. 6 and 8-10, the alternative frictional drive system will be described in further detail. Under the operative control of motor 140, the frictional drive employs a wheel 310 that is maintained in contact with an inner surface of the track, on the side opposite that which contains the power rails. In other words, the drive wheel 310 is biased away from the power rail side and into contact with the opposite side of the track. The biasing force applied to wheel 310 is supplied via springs 320 and idler wheels 322, where the idler wheels ride against the interior side of the track and force the drive wheel 310 into frictional contact with the opposite side. The drive assembly (FIG. 8) is allowed to slide or "float" relative to the support 130 as it is operatively coupled to the support 130 via slides 330. As a result of the disclosed alternative frictional drive mechanism, the first or horizontal drive 140 is slidably connected to the movable support, and the frictional drive mechanism is able to move relative to the support 130, along a direction that is generally perpendicular to the longitudinal axis of the track.

Planar support 130 is intended to be self-centering. That is to say that support 130 is maintained in a horizontal position that is generally centered relative to the track by the combination of at least four suspension assemblies 160 that are depicted in detail in FIG. 7. Each of the assemblies includes a top shoulder wheel 161 and a side shoulder wheel 162, where the top and side shoulder wheels each maintain contact with respective surfaces of the shoulder (246 or 248) extending outward from the track sides. In order to assure that the side shoulder and top shoulder wheels maintain contact and to assure proper tracking of the support, each suspension assembly further includes track idler wheels 164, along with cammed idler arms 165, that are pivotally attached to the assembly and operatively connected to one another via a toothed cam 167. Moreover, arms 165 are biased toward the track side surface that they contact by a spring 166. In this way the suspension assembly applies an equalizing force to the mounting block 168, which is in turn affixed to the support plate 130 to cause the plate to self-center during travel and while at rest. Having described the equipment and methodology for driving and controlling the support horizontally, attention is now turned to the balance of the system 100. Referring also to FIGS. 1-3, 11 and 14, the system further includes an actuator 400 attached to the movable support, where the actuator includes a second drive 410 and associated transmission 412, such as a worm-gear transmission, connected to and driving a rotatable drum 420. One advantage of employing a worm gear transmission is the speed reduction of the worm gear is resistant to movement and acts as a braking mechanism should the braking feature of the vertical drive motor 144 fail. The drum 420, is depicted in perspective view in FIG. 12. The second or belt drive 410 may be an ACOPOS servo drive produced by B&R in Austria (Model #1045) The drum has a strap 430, having a first end attached in a receptacle 422 and wound about an outer surface of the drum, with a second end of the strap ending in a coupler 432 to connect to a spreader bar 220 and support harness 222 (or similar supportive/assistive device) attached to support a person 110. The strap 430, and as a result the attached spreader bar and/or harness, is raised and lowered under the control of the belt drive 410. In one embodiment a harness having features such as that disclosed in U.S. Pat. Nos. 4,981,307 and 5,893,367 (both patents hereby incorporated by reference) may be employed with the disclosed system.

Although an exemplary strap and harness are depicted, it should be appreciated that various alternative harness configurations and support devices may be employed in accordance with the system, and that the intent is not to limit the scope of the disclosed system to the harness depicted. Alternative harness configurations and details may be employed, where several designs of the harness 222 are contemplated without the spreader bar. Harness 222 may include a backplate that is operatively connected, via straps or similar adjustable connections, to a sternum catch pad.

In another contemplated harness design a sternum catch pad has an opening through which the patient places his/her head, such that the pad is placed across the shoulders, over the head and then down the chest or front of the patient where the sternum catch pad is connected to torso pads that are similarly connected to the back plate and extend or wrap around respective sides of the patient's torso. Also, a pair of thigh pads may be provided, each one extending or wrapping around one of the patient's thighs (e.g., below the patient's quadriceps muscles), and each being adjustably connected to the backplate as well as to a connection on the sternum catch pad and/or optional junction pad. In one configuration the design includes a junction pad, a torso pad, sternum catch pad and thigh pads all connect to or through the junction pad. As will be appreciated, the harness 222 may have various configurations. Furthermore, one or more of the backplate and the pads attached thereto may include supporting structures such as metal rods, molded foam padding layers (possibly including impact hardening foam to disperse load forces), straps and associated adjustments and connectors, along with breathable materials such as meshes and the like.

Similarly, the strap 430 may be any elongate member suitable for suspending a person from the system, including rope, cable, etc. having braided, woven, or twisted construction, or possibly even linked or chain-type members. In one embodiment the strap is made from a sublimated polyester, and is intended to provide long life and resistance to stretching. As some therapeutic harnesses are presently adapted for use with strap-type support members, the following disclosure is generally directed to a strap-type member being wound around drum 420.

Figure 11:
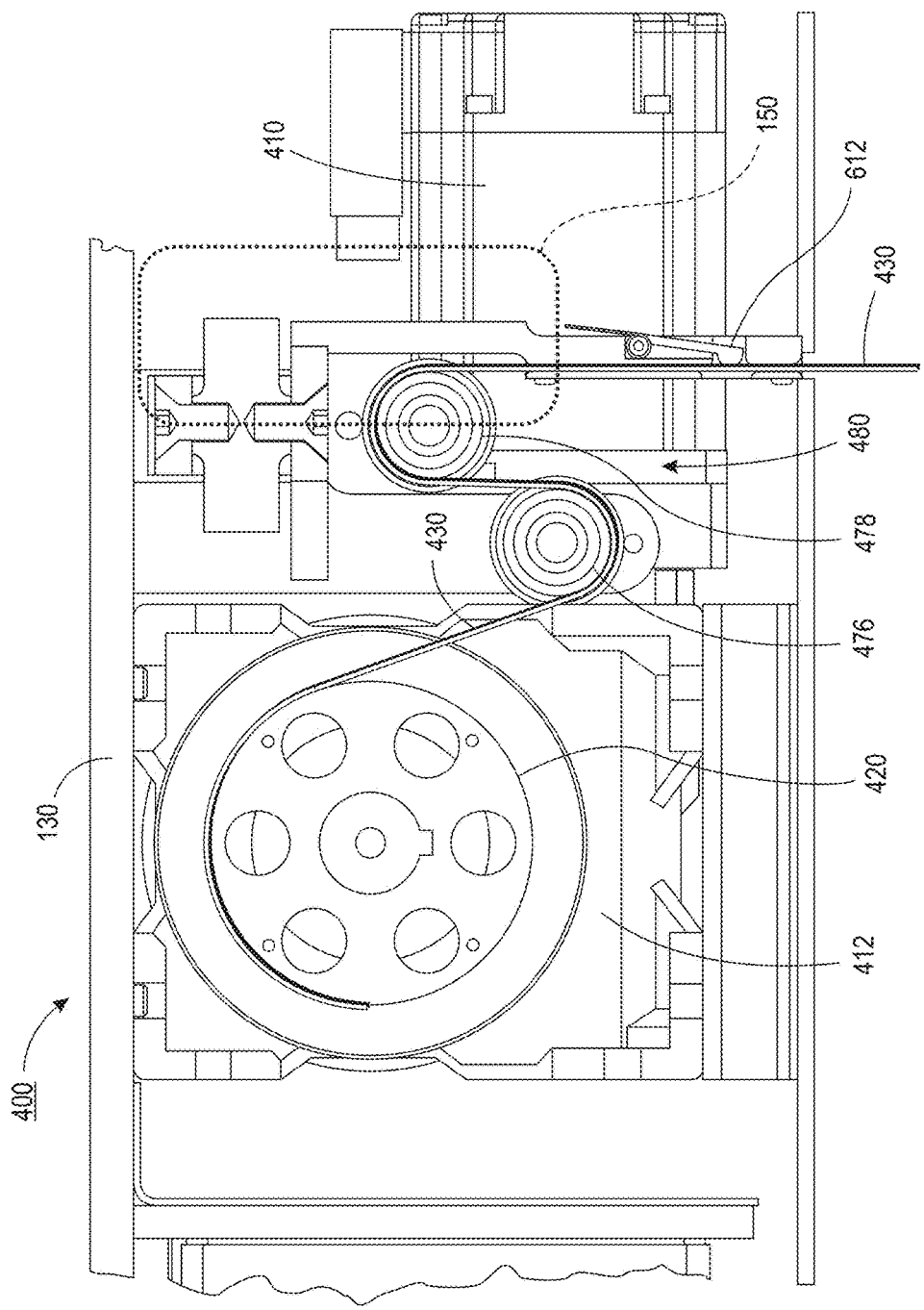
FIG. 11 is an enlarged view of a portion of the support including components of the vertical body weight support system.
Figure 12:
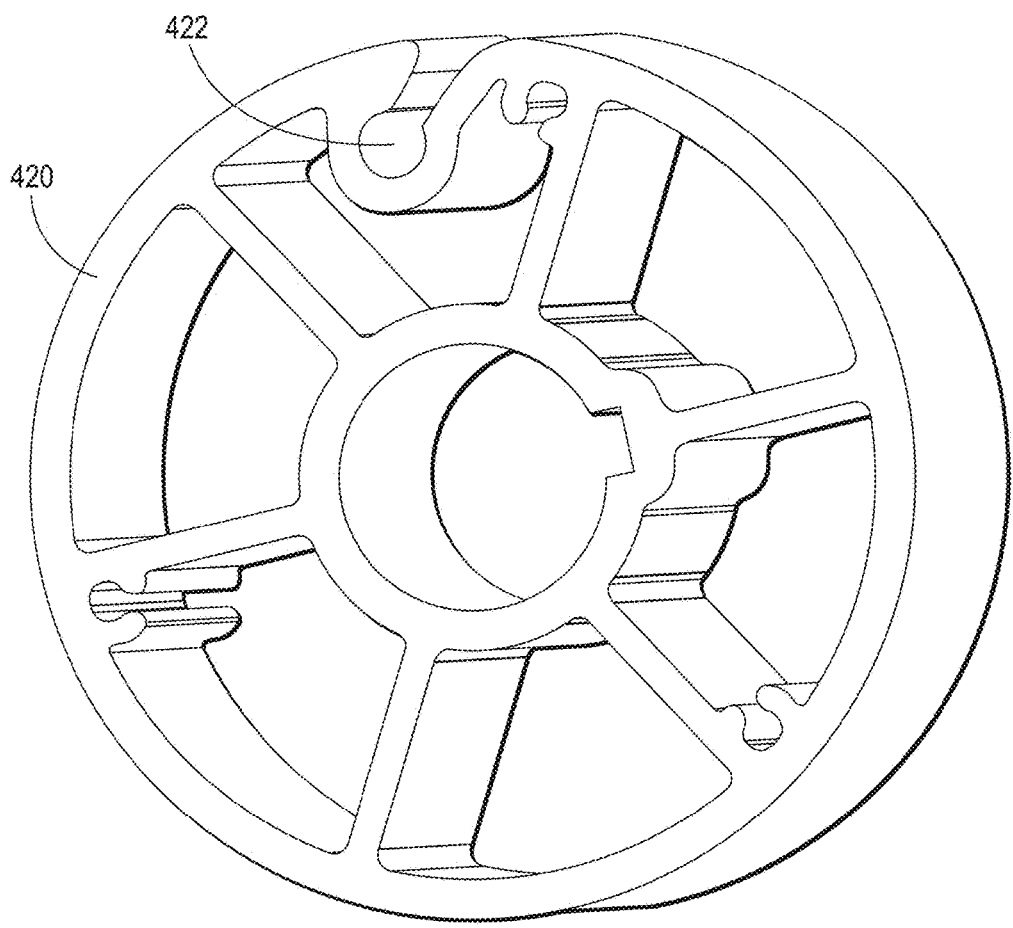
FIG. 12 is a perspective view of the drum used to wind the strap in the system of FIG. 11.
Figure 13:
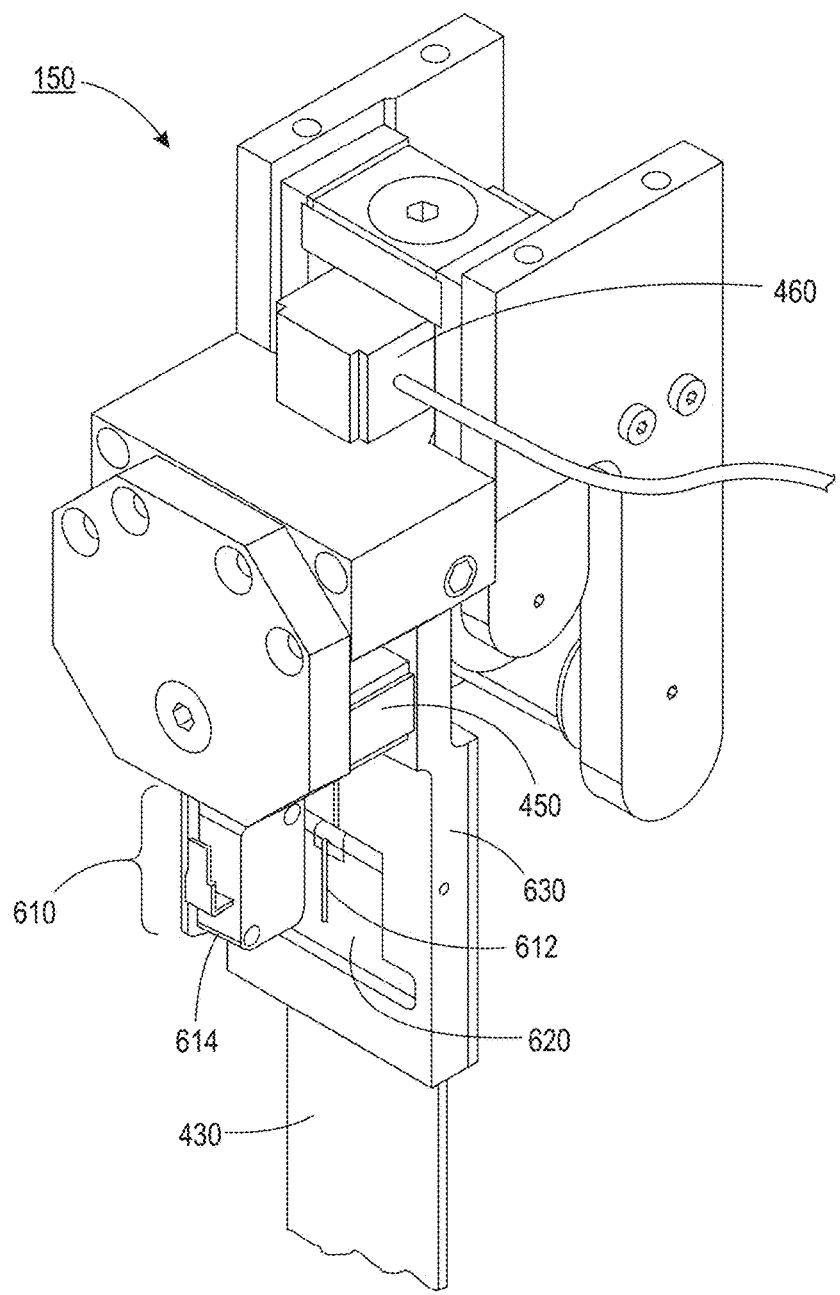
FIG. 13 is a perspective view of a strap slack/tension sensing system.

In one embodiment, as depicted in FIGS. 11 and 13 for example, the system includes a first or horizontal load sensor 450 for detecting a horizontal force applied to the support via the strap and a second, or vertical, load sensor 460 for sensing a vertical force applied to the strap. The load cell for the horizontal sensor 450 may be a bi-directional, in-line sensor suitable for axial force measurement.

Sensor 450 may be configured in a manner such that the sensor senses relative position change by a deflection in the downward-extending strap guide. More specifically, as the strap is moved forward or backward in the horizontal direction (H), sensor 450 generates a signal that provides a magnitude of the force applied in the horizontal direction, as well as the direction (e.g., +/−), and outputs the signal to the controller via cable 452. Thus, in one embodiment the horizontal force detection system detects a horizontal force via the strap using the strap guide operatively attached to and extending from the movable support unit, where the strap guide is operatively connected to a load cell in a manner that results in a change in the load cell output when the strap is pulled in a direction forward from or backward from vertical.

Figure 14:
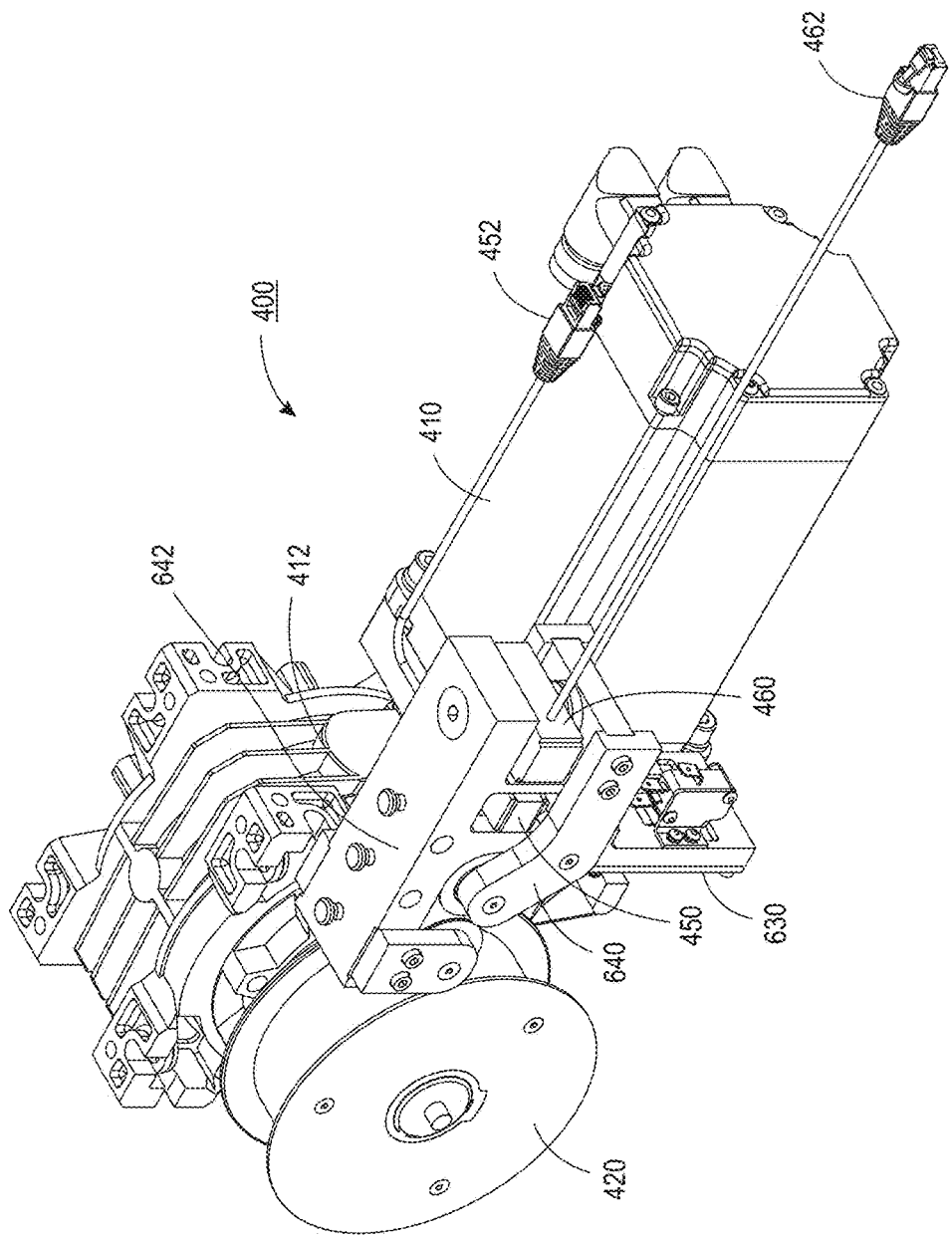
FIG. 14 is perspective view of a vertical drive, drum and strap sensing system in accordance with the support embodiment of FIG. 4.
Figure 15:
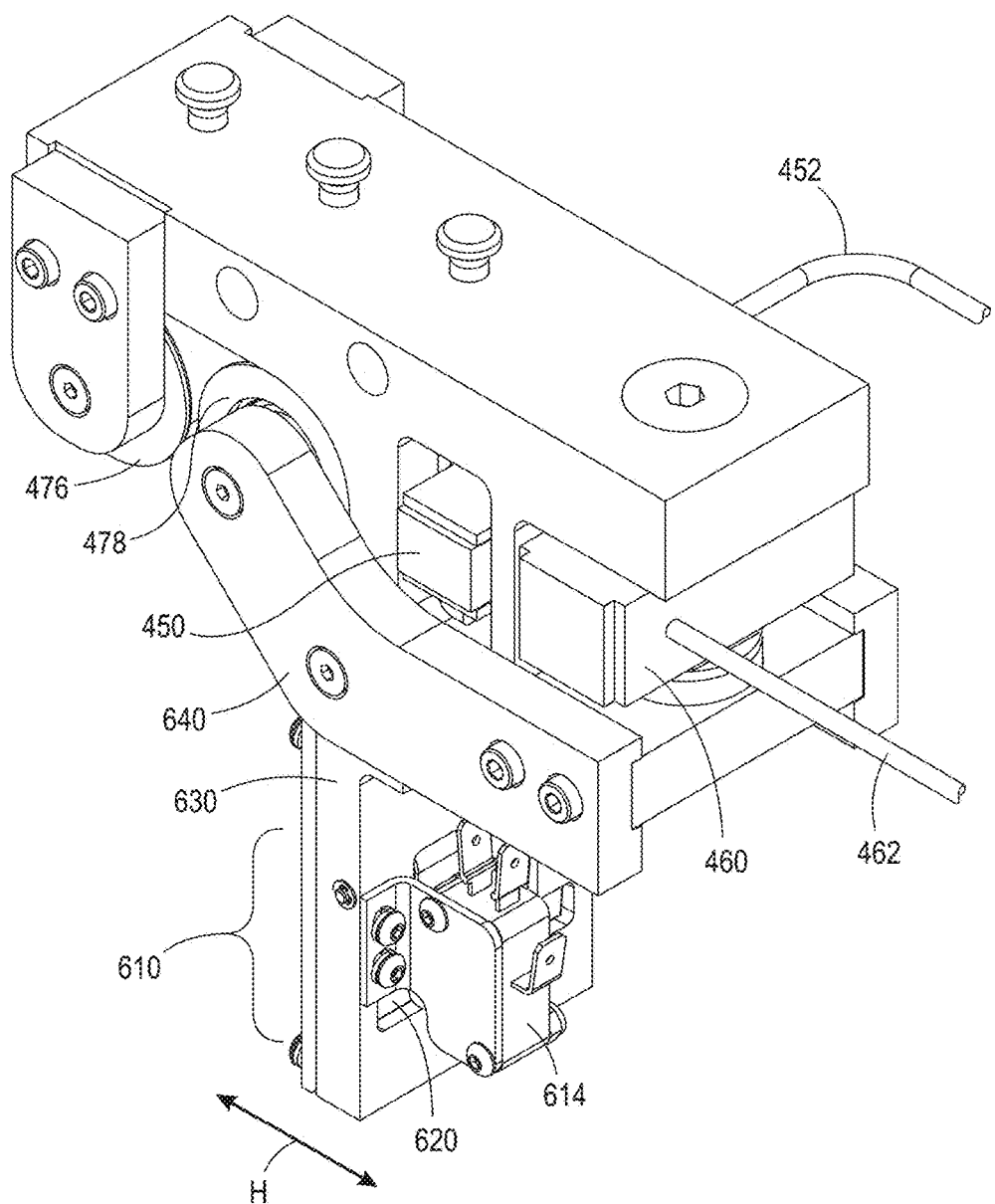
FIG. 15 is an enlarged view of the strap slack and tension sensing system in accordance with the embodiment of FIG. 4.

The strap or vertical force sensor 460, in order to provide increased resolution, may be employed in a compression-only configuration, to sense the force or tension in strap 430. In the system, the load sensor 460 is used for sensing a downward vertical force (tensile force) applied to the strap, and the sensor assembly includes at least two pulleys or rollers 476 and 478 in a single or double-reeved pulley system 480. The pulleys are located between the drum and strap guide 630. As illustrated in FIGS. 14 and 15, for example, the pulley is connected on one end of a pivoting arm 640; there the arm is pivotally attached near its mid-section to a frame member 642 coupled to the movable support plate 130. The opposite end of pivoting arm 640 is operatively associated with a load cell 460, so that a downward force applied via strap 430, results in a similar downward force being applied to pulley or roller 478. In turn, the downward force is transferred via arm 640 to apply a compression force on the load cell 460. Thus, load cell 460 is placed only in compression in response to a load suspended on the strap.

In response to signals generated by the load sensors 450 and 460, a control system, configured to receive signals from the first and second sensors and the user interface 172, controls the movement of at least the first and second drives to facilitate the support and movement of the person 110. Moreover, in accordance with one aspect of the disclosed system, the control system dynamically adjusts to provide constant support to the person (e.g., body weight support) via the strap and harness by altering at least the vertical force applied to the strap using the drum and second drive 410.

With respect to the vertical force, the controller operates, under programmable control to process signals from the vertical load sensor 460 via cable 462, in combination with prior inputs or pre-set information that sets vertical assistance to be applied to the person via the vertical drive and strap components. For example, the system may have various exercise or therapy modes such as those noted above, whereby the amount of vertical lift or support supplied is adjusted or modified based upon the particular exercise being conducted. For example, walking (gait tasks) over a flat surface the system may control the vertical force to allow the patient to experience about a 90% body weight, whereas on an incline or steps the percentage may be slightly lower, say at about a 70% body weight. To accomplish the control, the system must first determine the patient's body weight—either by sensing it directly in a full support mode or by having the weight (e.g., patient body weight, and optionally spreader bar and harness weight) entered via the user interface. Once determined, the vertical load sensor (load cell) 460 is then employed in a "float" mode to apply an adjusted force of say 10% (100−90) body weight to the strap and harness, and thereby reduce force experienced by the patient to approximately 90% of the patient's body weight.

Figure 16:
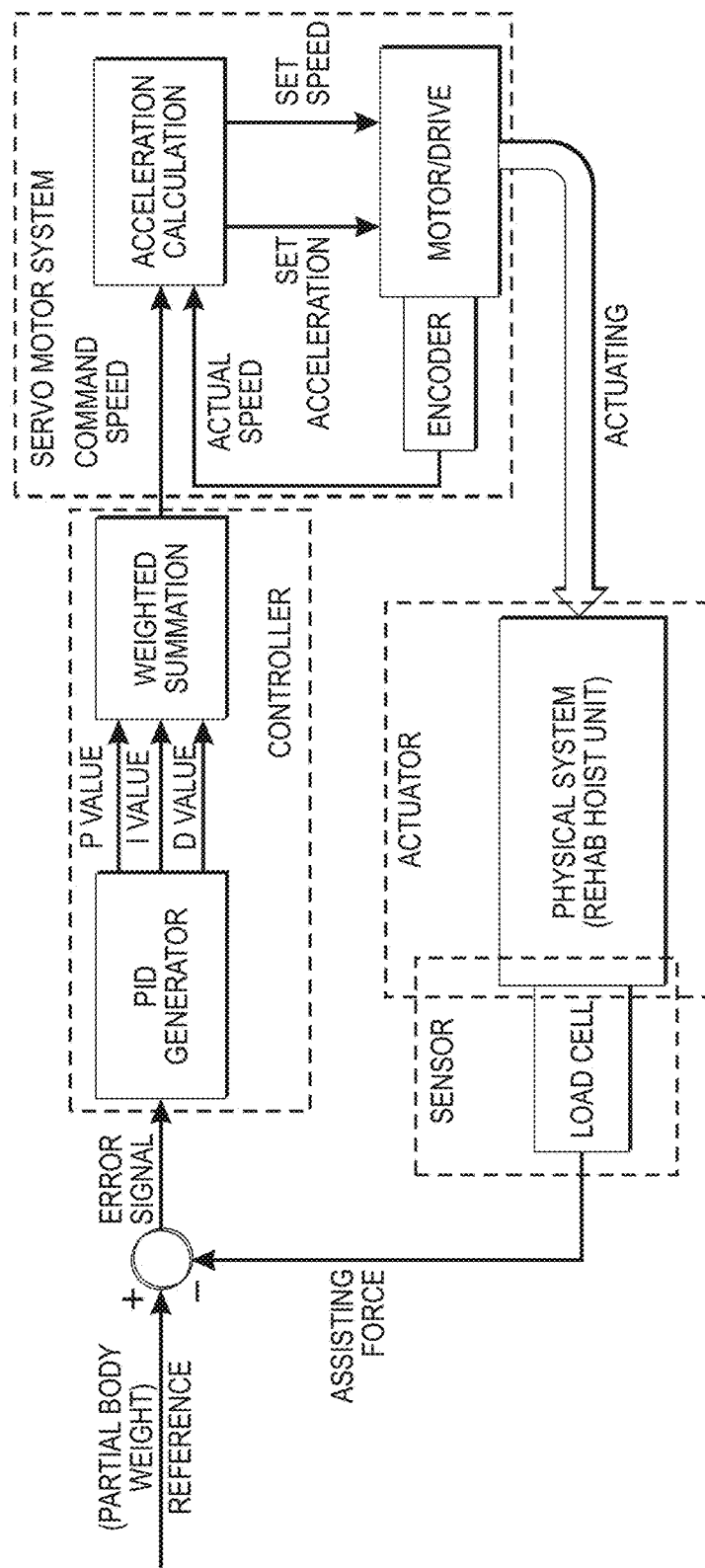
FIG. 16 is an illustration of the control flow for a disclosed embodiment of the rehab support system.

Referring briefly to FIG. 16, depicted therein is a control diagram indicating the relative relationship amongst system components, including the controller, drive servo motor system and the sensor feedback loop The closed-loop control system is applied in both directions (horizontal and vertical) using a PID control technique; proportional (P), integral (I) and derivative (D) gains. Moreover, an acceleration calculation routine is run prior to engaging a motor so that the motion profiles for the system drives are smooth.

In a manner similar to that of the vertical force sensor, horizontal load sensor 450 similarly senses the horizontal component of the load applied to the movable support by the user, via the strap 430. In this way, when the patient is engaging in an exercise or task that is intended to move along the track or path defined by track 120, the system 100, or more particularly the movable support 130 and associated components, may also index or move along the path in order to provide continued vertical support as the patient advances forward or rearward along the path, thereby minimizing the effect of the weight of the unit on the person. Another horizontal load sensing alternative contemplated is the use of a trolley suspension mechanism, with a moment arm associated with the suspended trolley having a load cell attached thereto, to sense changes in the force applied through the moment arm.

In one embodiment, the vertical and horizontal load and position control is accomplished using a programmable controller such as an ACOPOS servo drive, from B&R (e.g., Model #1045). Moreover, the functionality of the controller allows for the control of both the horizontal and vertical positions simultaneously so as to minimize or avoid any delay in the movement and to assure coordination of the control—particularly relative to limits, exercise modes, etc. as further described herein.

Referring also to FIGS. 11-15, the belt or strap 430 is wound on a drum 420 in a yo-yo-like fashion, so that the drum contains a plurality of coiled layers of the strap, and is fed through a reeved pulley system 480 to enable the reliable control of the strap and to facilitate sensing forces exerted on the strap. In view of the strap being wound upon itself, the position sensing mechanism associated with the vertical drive operates under the control of an algorithm that automatically adjusts the motion control to account for the change in radius as the strap is rolled or coiled onto and off drum 420. Also illustrated in FIGS. 13 and 15 is a belt tension sensing system 610, where a spring-biased arm 612 or similar contactor is in contact with the strap within a window 620 in guide 630. The arm pivots relative to the guide whenever the strap is slack, and in response to pivoting, the position is sensed by micro-switch 614 and causes a change in the state of the switch. Thus, when the strap is slack (i.e., not taught), the arm pivots under the spring force and the micro-switch is triggered to cause the system to stop further movement in either the vertical or horizontal mode—other than manually controlled movement.

Having described the general operation of the vertical and horizontal load control system, it will be appreciated that this system may be employed to enable multiple exercise modes for the patient such as those described above and represented in FIG. 38. For example, the user interface may be employed to select one or more of such exercise modes to be used. It may also be, as illustrated in FIGS. 17 and 18, that the exercise mode may be controlled via the location of the support relative to the track (e.g., 120). Referring to FIG. 17, for example, depicted therein is a track 120 that is laid out in a generally rectangular path or course. Along the path are a series of stations or zones 810a-810f, each of which may have one or more exercises to be completed at that station. For example, one station (810a) may be designed for walking on a flat surface and may have a set of parallel bars or railings for patient assistance. Another station (810e) may have an inclined ramp or stairs that the patient traverses, perhaps at a higher level of assistance (i.e., with a lower percentage of body weight being carried, thus a higher level of vertical support force applied via the strap).

As the movable support moves from one station to another around the loop as illustrated in FIGS. 17 and 18, the type and/or amount of assistance and the nature of the control may be pre-programmed according to the particular zone. It will be appreciated that the locations and characteristics of each zone may themselves be programmable via the user interface and that it is anticipated that loops or paths of varying size and configuration may be customized for the needs of particular patients, therapy centers, etc. And, as noted previously, such information may be stored in the database to facilitate subsequent programming of the system for a particular patient's therapy needs. For example, it may be possible to have a patient's programmatic information stored within a system, and when the patient arrives for therapy, the support system assigned to them is automatically programmed for the same or a slightly modified therapy session from the one that they experienced on their last visit.

As noted above, the use of multiple system units 100 is contemplated in one embodiment. However, it will also be appreciated that the use of multiple systems may require that such systems be able to avoid collisions and/or assure that a buffer space is maintained between adjacent patients. Thus, as illustrated in FIG. 17, the systems, either through a master controller suitable for monitoring the position of all systems, or through intercommunication between the systems themselves, maintain information related to the relative position of adjacent devices such that they maintain a safe separation distance D between the units. Although not illustrated, in the event of a system employing multiple system units, it is further contemplated that one or more units may be "parked" on a spur or other non-use location when not in use in order to allow unimpeded use of the entire therapy circuit by only a single user.

Figure 19:
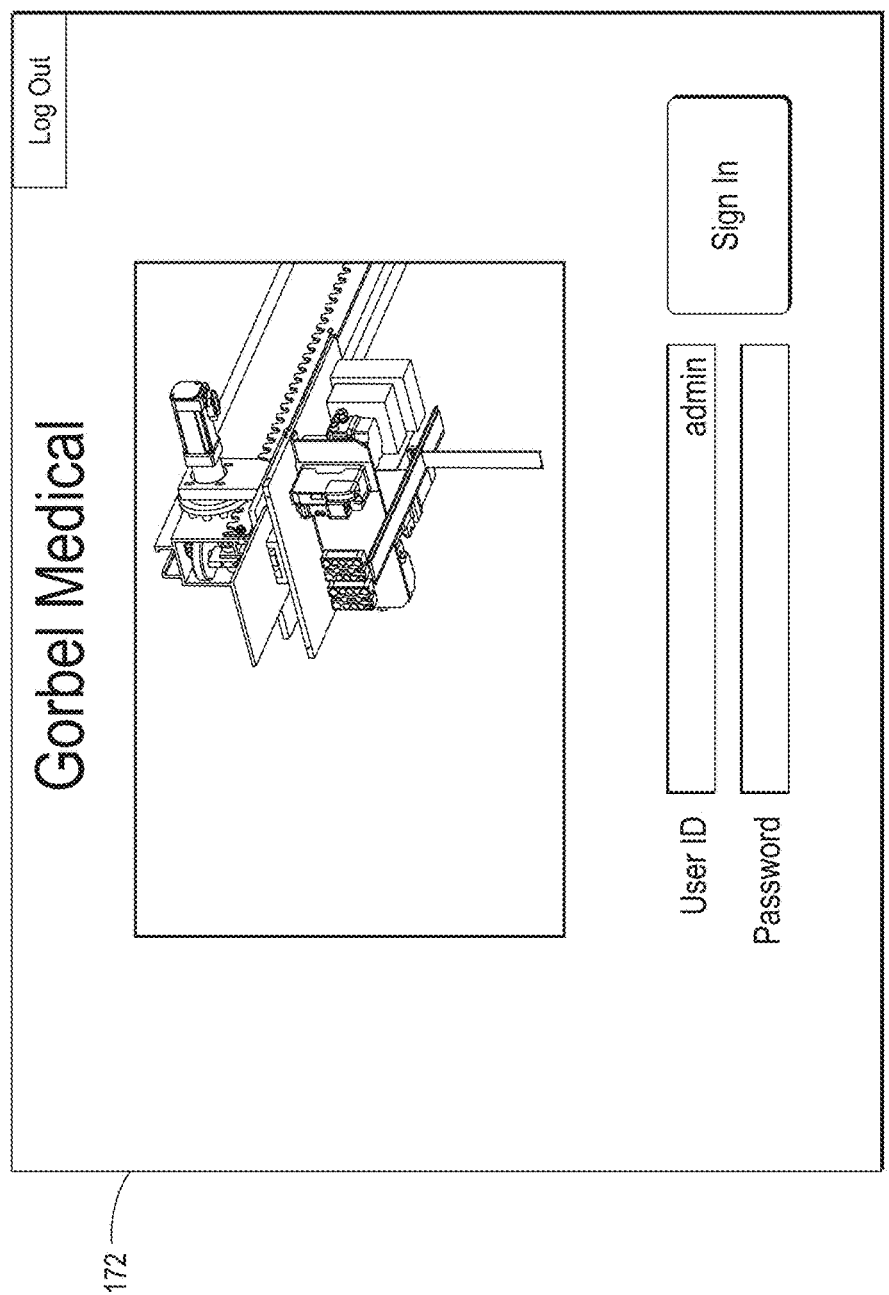
FIGS. 19-21 are illustrative examples of user interface screens for controlling basic operations of the rehab body weight support system.
Figure 20:
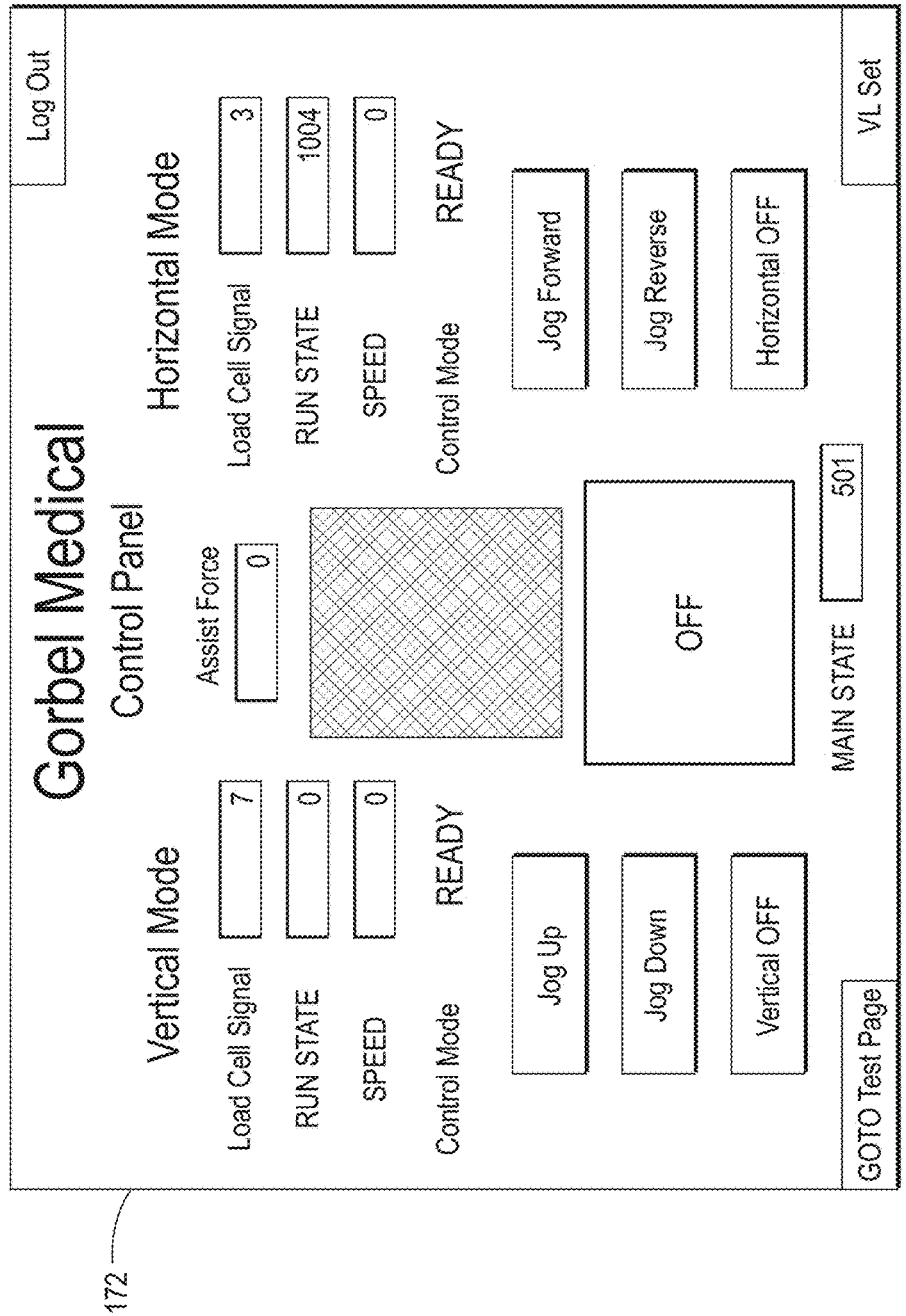

Referring again to FIGS. 19-21, depicted therein are exemplary user-interface screens to demonstrate operational features of the disclosed system. The screen depicted on U/I 172 in FIGS. 19 and 33 is a login screen to access the system control pages (interface), several examples of which are found in FIGS. 20-21. In FIG. 20, a control panel screen is illustrated for interface 172. The screen includes information for both the vertical and horizontal controls (modes), including fields indicating the respective load cell signals, run states and speeds. Also indicated is the control mode, in both cases showing READY, to indicate that the system is ready for use of both the vertical and horizontal controls.

In the lower part of the screen of FIG. 20, as well as in FIG. 40, there are shown a series of buttons permitting the manual control of the vertical and horizontal drives, respectively. Each subsystem may be jogged in either direction and the controls for that subsystem may also be disabled. Various system states, including systematic and/or actuator related state numbers, can be displayed for maintenance and/or troubleshooting. Also, the on/off controls for both horizontal and vertical motion are located on this page.

Also contemplated in accordance with the disclosed embodiments are one or more calibration techniques, whereby the various sensors (e.g., vertical load and horizontal force) are calibrated to assure accurate responsiveness to a patient. As noted herein, the load sensors are employed in different configurations and as a result the calibration techniques are also not the same. For example, the vertical force sensor may be employed in a compression-only configuration and thus gives a 1:1 correspondence between the load applied and the output of the load cell. On the other hand, the horizontal load sensor is not a 1:1 relationship to the load. However, the horizontal load sensing is slightly less critical to the operation and support of a patient and therefore a lower resolution/responsiveness may be tolerated for the horizontal load sensor.

Figure 21:
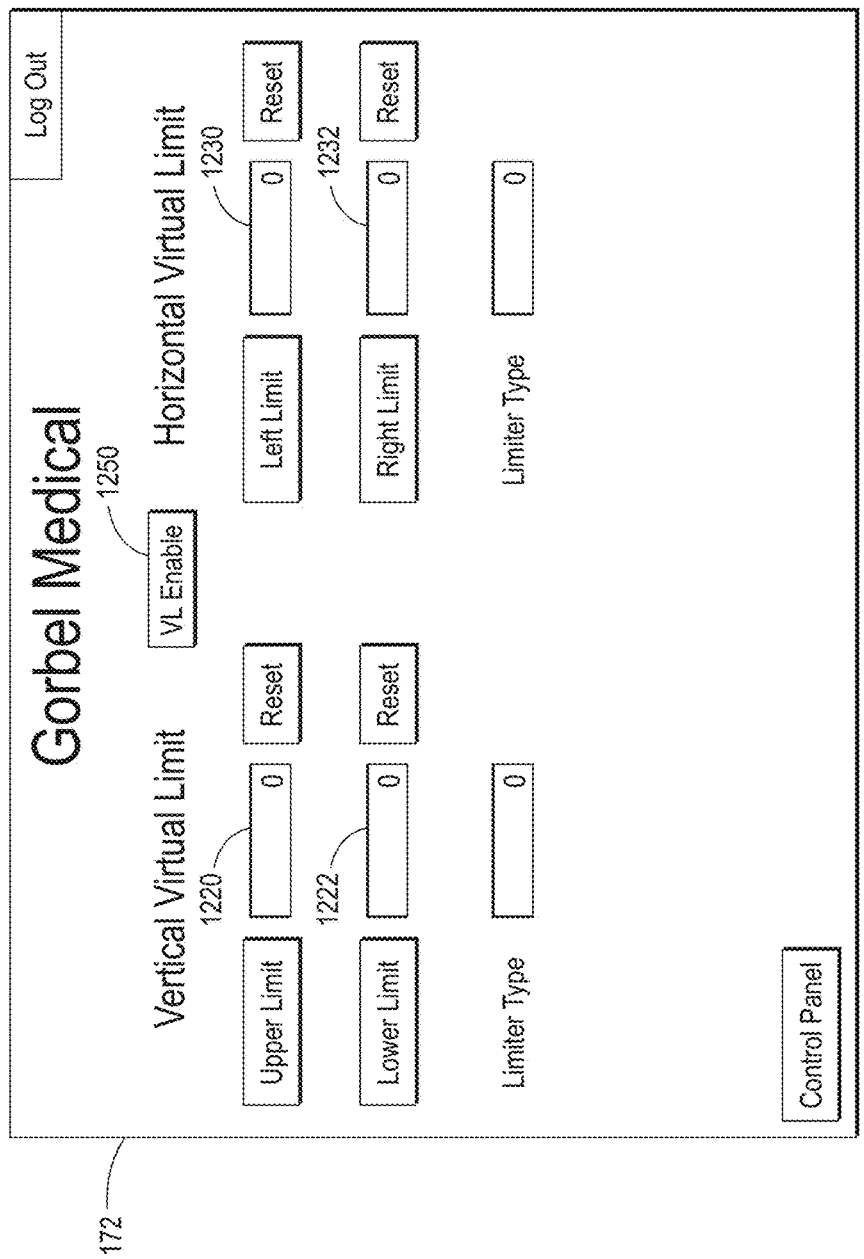

Another feature of the disclosed system is what is referred to as virtual limits. Referring also to FIG. 21, for example, a user interface for the virtual limits is depicted. In one embodiment, there may be several types of limits that are set for a particular system or patient. The limit type may specify a "hard stop" limit, or a soft or transitional limit (where the operation of float mode is adjusted or disabled). For example, in the case of hard stop limits, the limits are set based upon the position—both vertical and/or horizontal. Referring to FIG. 21, the upper and lower limits are entered into fields 1220 and 1222, respectively. And, use of the reset buttons adjacent to those fields allows the limits to be reset to a pre-determined or default level, or disabled. The left and right limits are similarly entered into fields 1230 and 1232, respectively, and they may also be reset to a pre-determined or default level or disabled. The depicted interface, as with those depicted in FIGS. 32-56, is responsive to user input via one of many input methods (e.g., touch-screen, mouse, stylus, keyboard, etc.), and the numeric values may be entered into the limit fields via a numeric keypad, scrollable window or other conventional user-interface techniques. Furthermore, such limits may be set by physically manipulating the unit into the position in which the limit is desired to be set, and then recording that location/position. It is further contemplated that the limits themselves may be set for particular zones 810, and that the values entered may be applicable over the entire system path or only over a portion (zone) thereof. It is also the case that the limits may be enabled or disabled via button 1250 on the screen of interface 172 as depicted in FIG. 21.

The user interface, as further illustrated in FIGS. 35-38 for example, is also contemplated to facilitate the collection, storage and display of information related to particular patients, including not only settings for the therapeutic exercises as noted above, but additional information as well.

For example, the interface may permit the collection and display of biometric information, user performance metrics, etc. The user interface may be enabled using various technologies in addition to or in place of the standing controller. Examples include wired and wireless devices or computing platforms as well as smartphones, tablets or other personal digital assistive devices, docking stations, etc. Moreover, the computing and/or control resources for the rehab body weight support system may reside in the kiosk controller 170, in the individual system units themselves, or in other locations that are easily accessed and interconnected through one or more wired or wireless connections.

The SafeGait™ 360° Balance and Mobility Trainer system also contemplates incorporating reporting functionality in the associated interfaces and storage devices, for example, the user interface directs queries to the database, and the system provides, in response to a query, one or more of the following reports or outputs:

Patient Record—Patient information is input by the user that can include demographic information, (Name, DOB, Height, Weight) provider information, (Subscriber ID) and clinical information (Prognosis, Date of Injury, Plan of Care, Progress Notes).

Task Outcomes—Provides task specific performance measures, (distance—for a gait task, Repetition—for a transfer task) in addition to non-task specific performance data, (time, # falls prevented, # BOOSTs (see BOOST description below), avg. body weight support (BWS) and speed. Therapists also have the option to capture the patient's rated perceived exertion.

Session Outcomes—As illustrated, for example in FIG. 47, the session record or report provides aggregate performance measures for an entire session: Active time, (time patient was engaged in tasks) distance, repetitions, # falls prevented, # BOOSTs, avg. BWS & Speed Historical Comparison—Allows therapists, patients and others to select and graphically compare historical performance by task and session.

Although generally described relative to patient data, also contemplated in the reporting features is the storage and reporting of data relative to the operation of the system(s) (e.g., number of patient records, cumulative usage of the system(s), usage time by therapist, etc.) in response to queries to the database, for purposes of tracking the performance of the system(s) as well.

Figure 22:
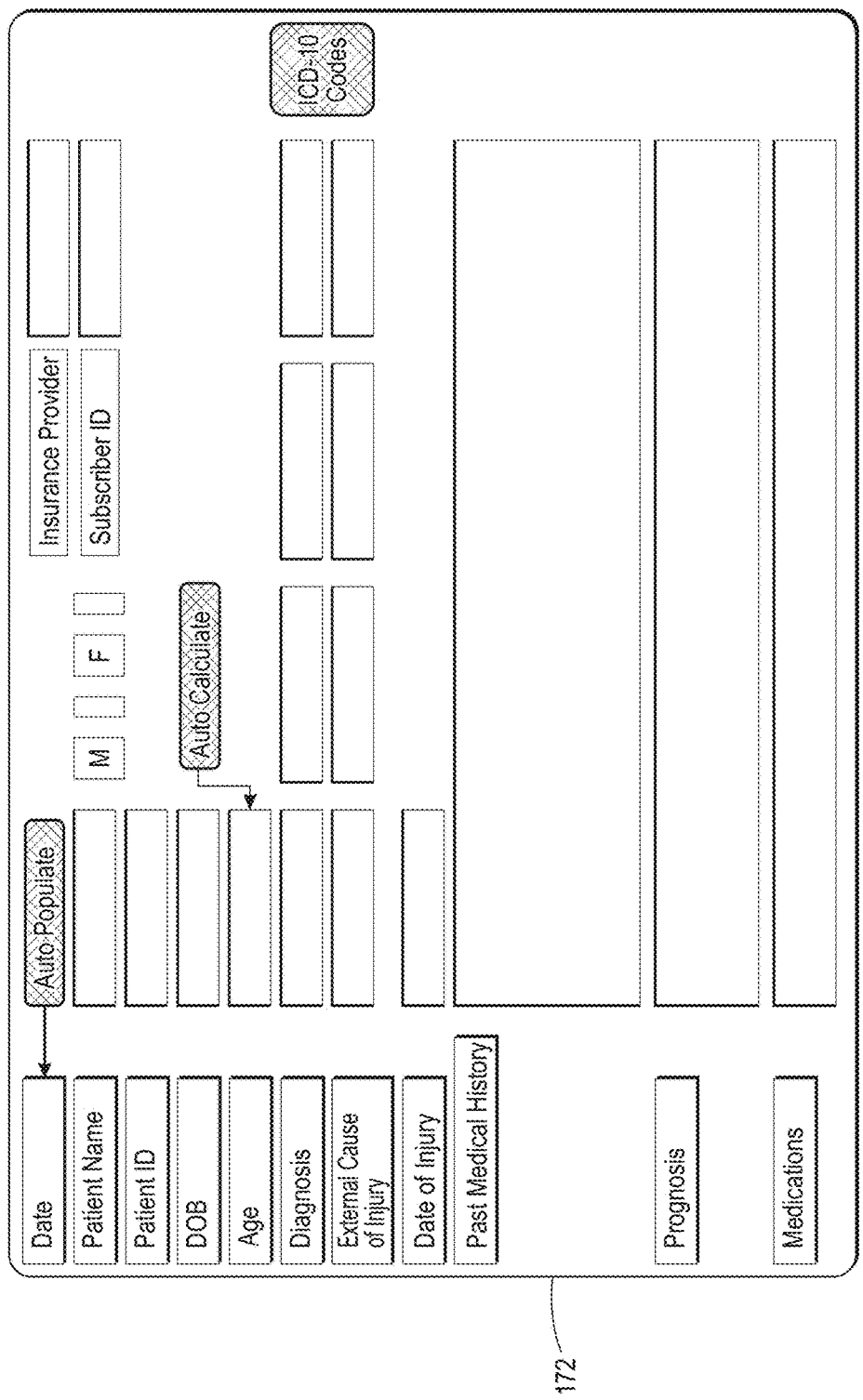
FIGS. 22-23 are illustrative examples of user interface windows for tracking and entering patient-specific information relating to use of a rehab body weight support system.
Figure 23:
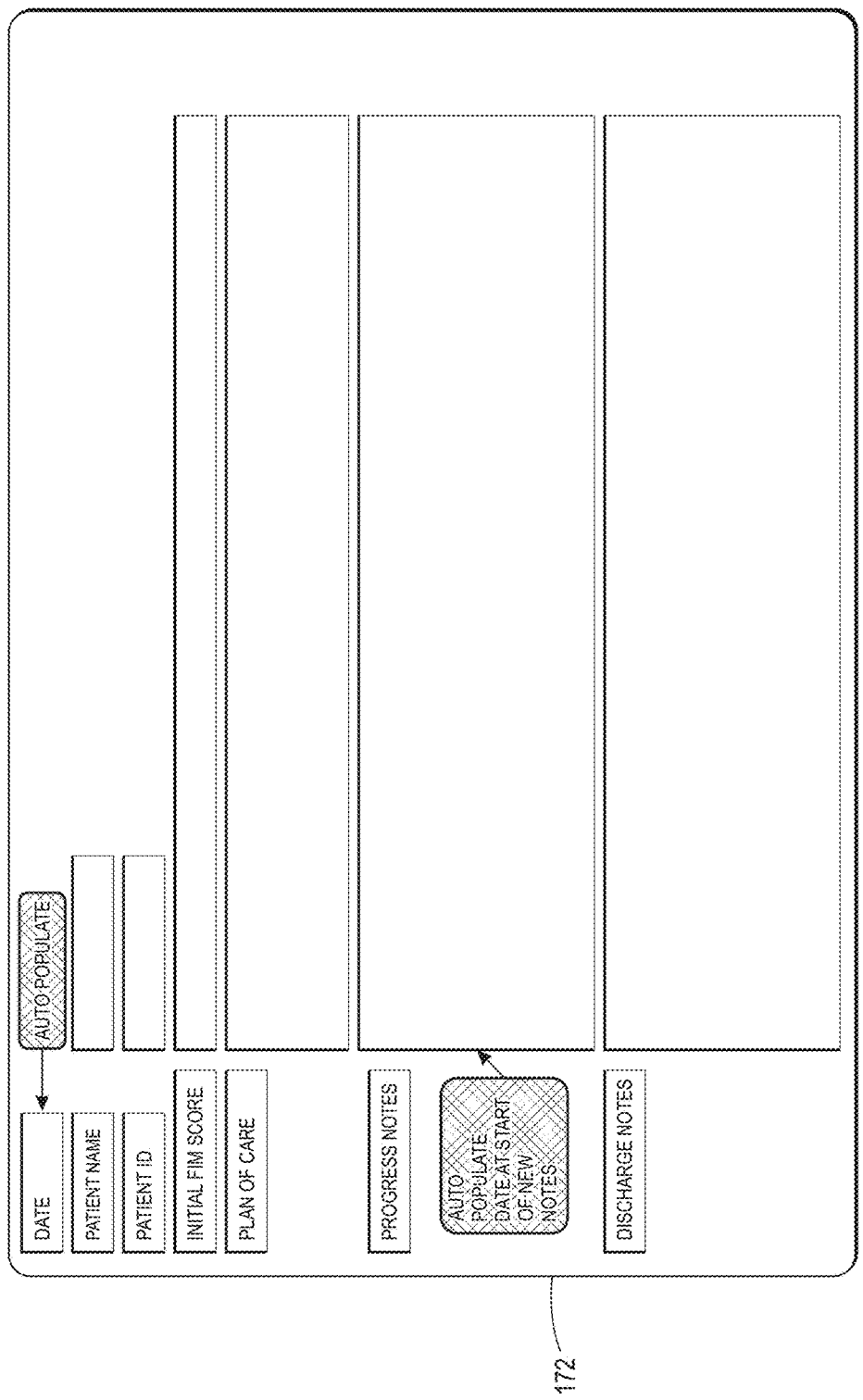

In one embodiment, in addition to a user interface, the system, particularly the movable support unit 104, may include one or a plurality of indicators such as light-emitting diodes (LEDs) that are under the control of and operated by the control system. The indicators may be provided on any external surface or housing of the support unit, and would be located in a position (e.g., FIG. 3, location 912) where they would be readily visible to a therapist and/or user of the system in order to provide a visual cue while the therapist is watching the patient using the system. The indicators would display an operational status of the system, and may further signal faults or other information based upon the LED color, mode (e.g., on, off, flashing speed) and combination with the other LEDs. As noted above, the user interface may include handheld as well as any permanently located devices such as touch screens and the like, may also be suitable for displaying information from the control system, and receiving information entered by a therapist to control an operation of the system (see e.g., FIGS. 19-21). As further illustrated by FIGS. 22-26, the system may include additional computing resources, such as memory or storage devices that enable the storage of data associated not only with system operation, but patient data as well. In one embodiment, the system includes an operation database for storing information relative to the operation of the system. Such a database may also store information relating to use of the system by different patients and their therapists. For example, FIGS. 22-23 are illustrative examples of user interface windows that may be used for tracking and entering patient-specific information relating to use of a rehab body weight support system. As shown in FIGS. 22 and 23, various fields are provided to both display and to enter patient information (or have it automatically populated from the database). Certain fields include patient record information for review by the therapist (e.g., date of injury, medical history, prognosis, medications in FIG. 22) while other fields allow the therapist to input information based upon the patient's use of the system (e.g., Initial FIM score, plan or care, progress notes, and discharge notes as illustrated in FIG. 23).

Figure 24:
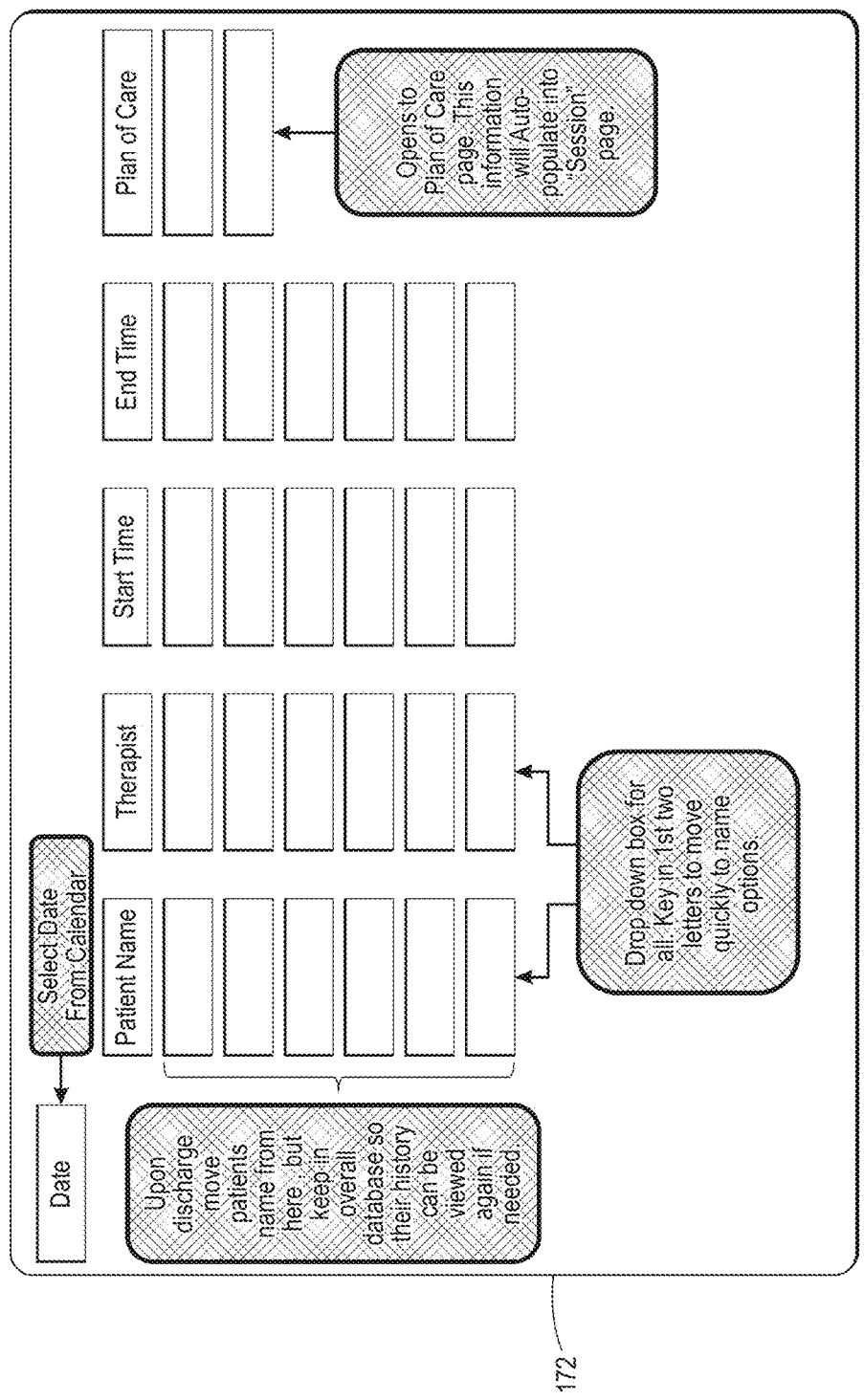
FIG. 24 is an illustrative example of a user interface day list window.
Figure 25:
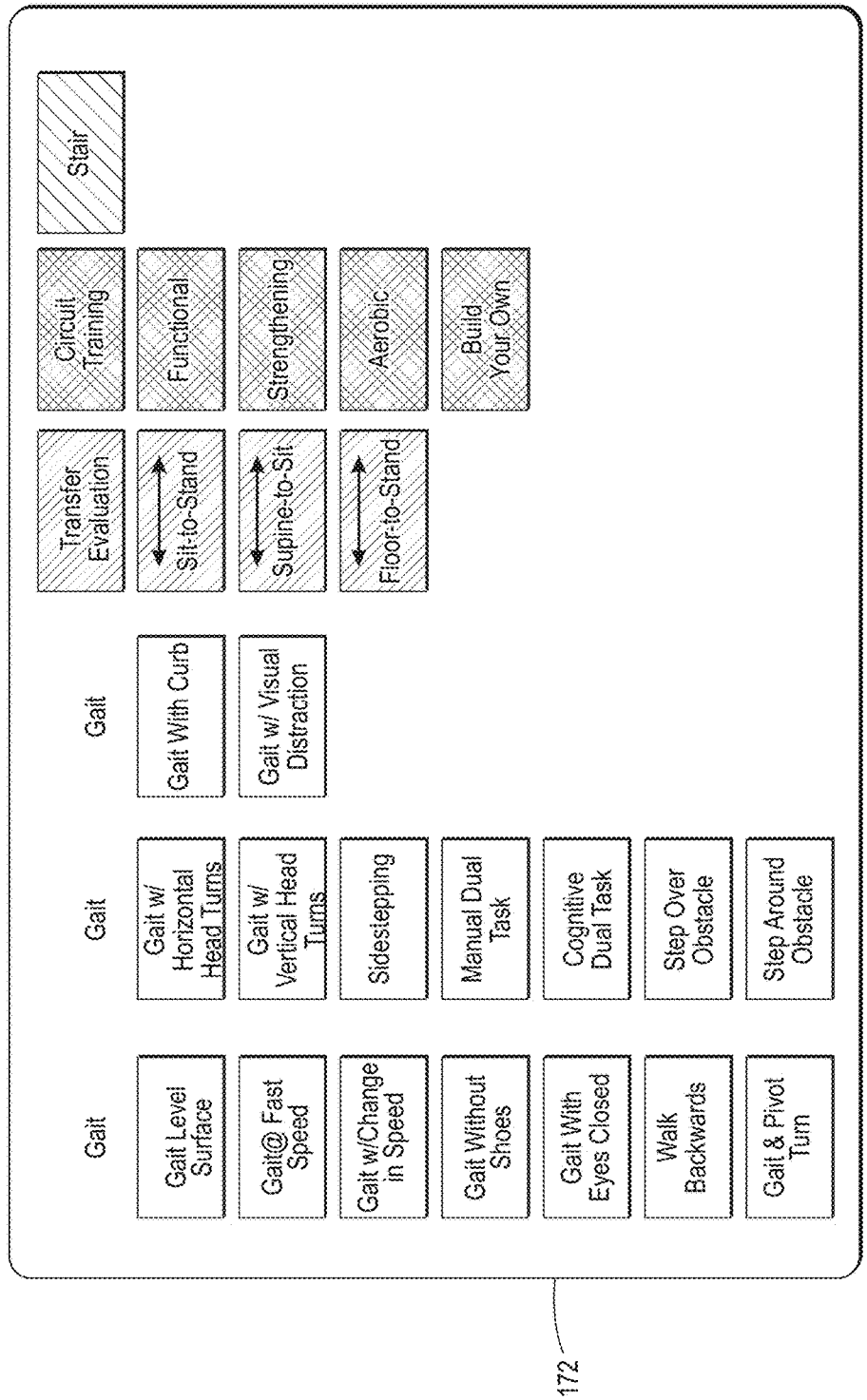
FIG. 25 is an illustrative example of a user interface plan of care window.
Figure 26:
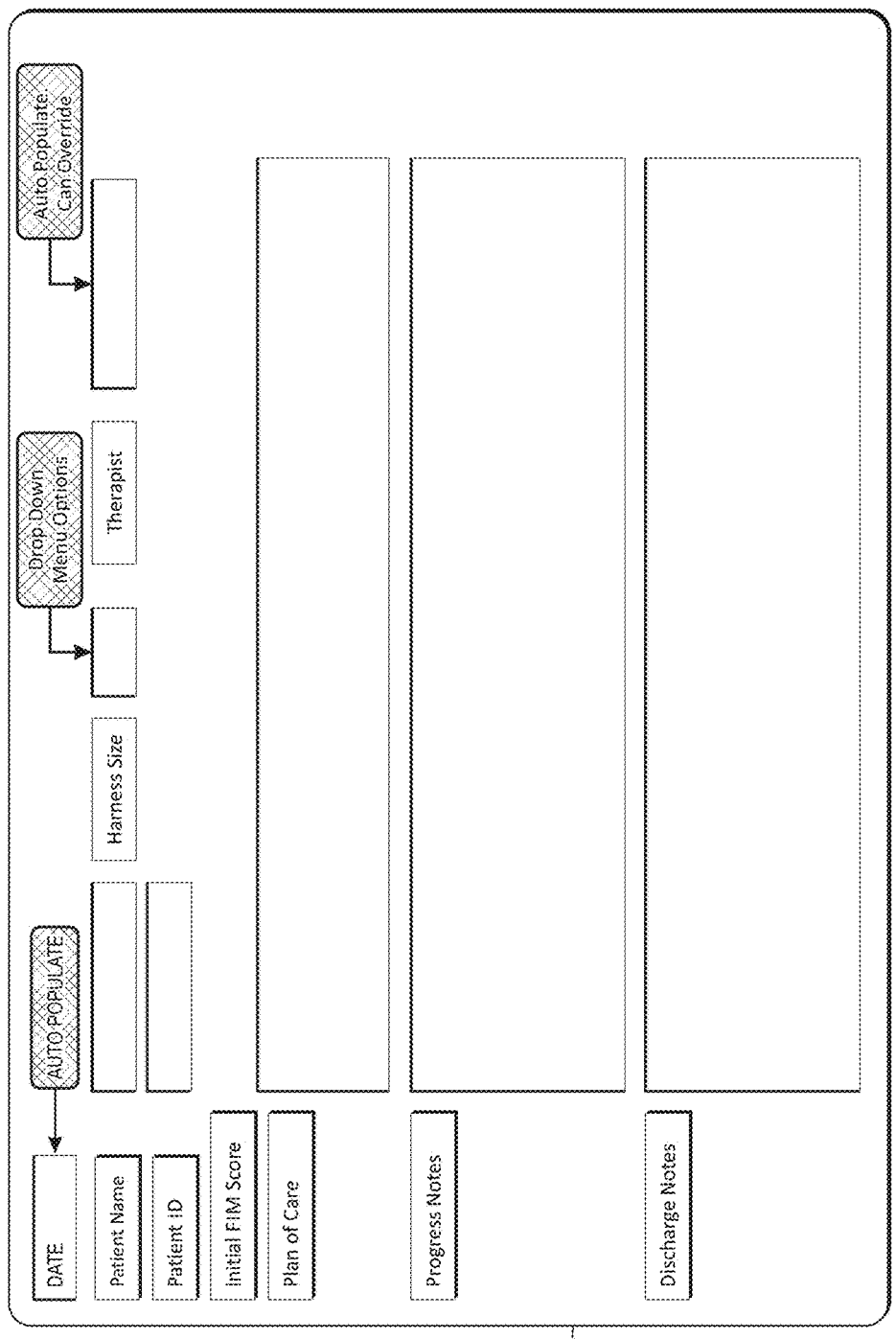
FIG. 26 is an illustrative example of a user interface window for review and entry of data for a patient session.

Referring briefly to FIG. 24, there is shown an illustrative example of a user interface 172 depicting a day list window that represents scheduling or usage of the system. As noted, some of the fields depicted on the interface window 172 of FIG. 24 may auto-populate from information contained in the system database, whereas other fields may be drop-down or similar data entry fields that are available to a therapist or other user of the system. Similarly, FIG. 25 provides an illustrative example of a user interface plan of care window on the user interface 172. In the plan of care window, a therapist may select from one or more pre-programmed activities for the patient. It will be appreciated that the various activities are subject to programmatic control and the input of certain patient-specific information that may be entered or previously stored in the database. Lastly, FIG. 26 provides an illustrative example of a user interface window for review and entry of data for a patient session. Once again, certain fields may be pre-populated with information based upon the patient ID or similar unique identifier. And, the patient session interface also includes fields for the therapist to enter information. It will be understood that the use and display of information is not limited to the particular interface screens depicted. Moreover, the system may also be able to track a patient's performance in order to measure the number of reps, amount of assistance, number of falls prevented, etc. in order to provide such data in the future, or as a performance measurement over time. The dynamic fall prevention aspects of the disclosed embodiments, particularly when the system controller is operated in what is referred to as a float mode, permits the sensing of dynamic fall events, and while preventing actual falls, the system can also log the occurrences for subsequent review and tracking.

In yet another embodiment, the SafeGait™ 360° Balance and Mobility Trainer system further includes or facilitates several additional features. The following features may be implemented on system 100 or a similarly configured system for providing assistance:

Dynamic Fall Protection—

Dynamic Fall Protection (DFP), as briefly mentioned above, and as represented in FIG. 44, enables the device to sense a fall instead of, or in addition to, setting a pre-defined fall limit (Descent Limit). This makes the response of the SafeGait system more intuitive for a therapist who does not need to pre-determine a height for fall arrest. It also provides fall protection in cases where a Descent Limit cannot be set or may have been set very low; for instance transfer tasks such as supine-to-stand requiring the patient's full vertical range of motion. When a fall is detected with DFP, further vertical movement in the downward direction is inhibited.

The patient is allowed movement in only the upward direction and horizontally, albeit at a reduced speed, making it easier to right themselves.

Dynamic Fall Protection (DFP) Sensitivity Levels—

The DFP Sensitivity Levels are set via an interface screen such as FIG. 44, and allows therapists to adjust fall protection sensitivity to one of a plurality of sensitivities to accommodate patients at varying stages of independence (e.g., High, Medium, Low). At High sensitivity, a fall is detected with very slight movement in the vertical direction. On the other hand, at Low sensitivity a fall is only detected with much more drastic vertical movement (approaching freefall).

There are at least two options for DFP monitoring, including detection of a change in force or a change in speed for the patient being supported by the system. In the force-based option, the force being applied via the strap 430 is continuously monitored for a change that is indicative of a possible fall or other rapid downward movement of the patient. In the speed-based option the speed of the downward vertical movement of strap 430 is monitored, and in the event of the speed exceeding a threshold the motion is dampened or stopped by the system. As will be appreciated, the thresholds applied for the force or speed, in the respective options, are possible variables that may be modified to adjust the sensitivity of the system for fall detection and prevention. Moreover, there may be other system performance metrics that could be used in fall detection (e.g., rapid change in strap angle), and it is also contemplated that a combination of two or more detection options may also be implemented in order to permit the system to detect other "fall" scenarios.

Descent Limit—

A secondary fall protection feature, referred to as Descent Limit (see FIG. 44), sets a maximum amount of downward travel of the strap 430 (and patient) and the limit is a variable level based on the patient's position and height. The descent limit can be toggled on or off at will during a task, and set to whatever height within the actuator's range is needed for the task to be performed. When a fall is detected with Descent Limit, further vertical movement of the strap in the downward direction is inhibited. The patient is allowed movement in the upward direction and horizontally, albeit at a reduced speed, once again making it easier to right themselves.

Boost Mode—

The system may be operated by a patient and/or therapist to provide a boost force via the strap during a particular activity that the patient is performing. Engaging the BOOST mode (e.g., via button on interface screen 172 in FIG. 42) provides an additional portion (e.g., fractional percentage) of body weight support for a period of time (e.g., seconds). For example, the system may provide an additional 20% body weight support (BWS) for 10 seconds. And, the amount of boost as well as the time period may be variables that are adjustable by the therapist or user of the system, and may, as described above, be similarly set, adjusted and/or stored on a patient by patient basis. The concept behind BOOST centers on being able to assist a patient in completing a task as they fatigue, (i.e. a final sit-to-stand repetition). BOOST mode allows the therapist to offer the patient added BWS for a short duration with a single action, (one click) as opposed to adjusting the body weight support settings twice (e.g., first adjusting it upward for more support followed by quickly adjusting it back to the previous level).

Also contemplated in the disclosed embodiments is the automatic population of certain pieces of operational information (fields), as well as operational settings for the system, based upon not only the information stored in the database, but the entry of data by the therapist as well. As a result, a user interface such as the examples set forth would be available to a therapist or other user of the system, and may display information selected in the form of a patient record window, a day list window showing use of the system, a plan of care selection window and/or a session data window.

It should be understood that various changes and modifications to the embodiments described herein will be apparent to those skilled in the art. Such changes and modifications can be made without departing from the spirit and scope of the present disclosure and without diminishing its intended advantages. It is therefore anticipated that all such changes and modifications be covered by the instant application.

What is claimed is:

1. A system for supporting weight-bearing therapies of a person, comprising:
a movable support unit operatively associated with and moveable along or relative to a support system, the movable support unit being movable along a path;
at least a first drive associated with the movable support unit, said first drive moving the movable support unit along the path;
an actuator attached to the movable support unit, said actuator including a second drive for driving a rotatable drum, said drum having a first end of a strap attached thereto, said strap wound in an overlapping coil fashion about an outer surface of the drum, and a second end of the strap being coupled to a support harness attached to support the person;
a first sensor configured to measure a magnitude and a direction of a horizontal force applied to the movable support unit via the strap;
a second sensor configured to measure, as a tensile force, at least a magnitude of a vertical force applied to the strap;
a control system configured to receive signals from the first and second sensors and a user interface, the control system configured to control, in response to the received signals, the movement of at least the first and second drives to facilitate the support during movement of the person, where the control system dynamically adjusts the amount of support provided to the person by moving the movable support unit horizontally along the track to follow the person and by dynamically altering the vertical force applied to the person via the strap, the drum and the second drive; and
a database for storing data representative of the operation of the system, said database being associated with the control system and where the user interface directs queries to said database, said system providing, in response to a query, at least one report selected from the group consisting of: a patient record, task outcomes, session outcomes, and historical comparisons.

2. The system according to claim 1, further comprising a dynamic fall prevention mode.

3. The system according to claim 2, wherein the dynamic fall protection mode has an adjustable sensitivity level.

4. The system according to claim 1 further comprising:
a plurality of indicators, operated by the control system, said indicators displaying an operational status of the system; and
said user interface further displaying information from said control system and said database, and also receiving information entered by a therapist to control at least one operation of the system.

5. The system according to claim 1, wherein the database stores information relative to the operation of the system and where the user interface further displays information in a format selected from the group consisting of: a patient record window; a day list window showing use of the system; a plan of care selection window; and a session data window.

6. The system according to claim 1, further comprising a boost mode, wherein when the system operates to support a portion of the body weight of the person a temporary increase in the amount of body weight support is applied by the system.

7. The system according to claim 1, wherein the path is defined by a track, and where the first drive is frictionally coupled to a surface of the track to control the horizontal position of the movable support unit along the track.

8. A system for supporting weight-bearing therapies of a person, comprising:
a movable support unit operatively associated with and moveable along or relative to a support system, the movable support unit being movable along a path;
at least a first drive associated with the movable support unit, said first drive moving the movable support unit along the path;
an actuator attached to the movable support unit, said actuator including a second drive for driving a rotatable drum, said drum having a first end of a strap attached thereto, said strap wound in an overlapping coil fashion about an outer surface of the drum, and a second end of the strap being coupled to a support harness attached to support the person;
a first sensor configured to measure a magnitude and a direction of a horizontal force applied to the movable support unit via the strap;
a second sensor configured to measure, as a tensile force, at least a magnitude of a vertical force applied to the strap;
a control system configured to receive signals from the first and second sensors and a user interface, wherein said user interface comprises at least one computing system spaced apart from said movable support unit, the control system configured to control, in response to the received signals, the movement of at least the first and second drives to facilitate the support during movement of the person, where the control system dynamically adjusts the amount of support provided to the person by moving the movable support unit horizontally along the track to follow the person and by dynamically altering the vertical force applied to the person via the strap, the drum and the second drive; and
a database for storing data representative of the operation of the system, said database being associated with the control system and where the user interface directs queries to said database, said system providing, in response to a query, at least one report selected from the group consisting of: a patient record, task outcomes, session outcomes, and historical comparisons.

9. The system according to claim 8 wherein said interface displays at least one operational setting selected from the group consisting of: user administration, patient administration; system management; actuator interface.

10. The system according to claim 9 wherein said interface displays at least one user administration operation selected from the group consisting of: Login; Logout; Add User; Update User; Reset Password; Change Password; and Disable/Enable User.

11. The system according to claim 9 wherein said interface displays at least one patient administration operation selected from the group consisting of: Add Patient; Update Patient; Add Session; Update Session; Get Tasks; Add Custom Task; Get Patient Sessions; Get Patient Goals; and Get Session Task Metrics.

12. The system according to claim 9 wherein said interface displays at least one system management operation selected from the group consisting of: Heartbeat Monitor; Actuator Connectivity Monitor; Kiosk/Remote Heartbeat; Grab System Control; Throw System Control; Get/Set Application Settings; and Exit App/Shutdown.

13. The system according to claim 9 wherein said interface displays at least one actuator interface operation selected from the group consisting of: StopAll; reset; move; stop; get status; get version; get serial number; begin task; end task; enable float mode; enable descent limit; set repetition lower limit; set repetition upper limit; set descent limit height; set body weight support; set Dfp sensitivity; apply boost; and clear fall.

14. The system according to claim 8 wherein said computing system is in wireless communication with said movable support unit.

15. The system according to claim 8 wherein said interface displays stored data for the person, retrieved from said database, to facilitate the selection of at least one therapy task for the person.

16. A method for supporting a person during rehabilitation therapy, comprising:
providing a track, the track including a plurality of extruded members joined end-to-end, and a plurality of electrical rails arranged longitudinally along an interior portion of the track for each portion of track, wherein at least one extruded member includes a generally planar upper surface extending in a longitudinal direction, opposing sides extending longitudinally and downward from each side of the upper surface, and where a combination of the upper surface and downward-extending sides form the interior portion of the track, each of said opposing sides further including a shoulder extending in an outward direction therefrom;
operatively attaching a movable support unit to the track, the movable support unit being movable along a path defined by the track in a first direction and in a second direction generally opposite to the first direction;
moving the movable support unit along the path defined by the track using a first drive attached to the movable support unit, wherein the first drive is operatively coupled to a surface of the track to control the horizontal position of the movable support along the track, and where the movable support unit is suspended from rollers resting on each of the shoulders extending from the opposing sides of the track;
controlling the vertical position of the person using an actuator attached to the movable support unit, said actuator including a second drive for driving a rotatable drum, said drum having a first end of a strap attached thereto and the strap wound in an overlapping coil fashion about an outer surface of the drum, and a second end of the strap being coupled to a support harness attached to support the person;
measuring a magnitude and a direction of a horizontal force applied to the movable support unit via the strap using a first sensor, the first sensor including a strap guide operatively attached to and extending from the movable support unit, the strap guide being attached to a first load cell in a manner causing a change in the first load cell output when the strap is pulled in a direction forward from or backward from vertical;

measuring at least a magnitude of a vertical force applied to the strap using a second sensor, the second sensor including at least one pulley between the drum and the person supported by the strap, wherein the pulley is connected on one end of a pivoting arm, said arm being pivotally attached near its midsection to a frame member coupled to the movable support unit, and where an opposite end of said pivoting arm is operatively associated with a second load cell such that the second load cell is placed only in compression in response to a load suspended on the strap;

providing a control system configured to receive signals from the first and second sensors, and a user interface, and to control the movement of at least the first and second drives to facilitate and support movement of the person, where the control system dynamically adjusts the amount of support provided to the person by moving the movable support unit horizontally along the track to follow the person; and storing, in a database, data representative of the operation of the control system, said database responding to a query to provide at least one report selected from the group consisting of: a patient record, task outcomes, session outcomes, and historical comparisons.

17. The method according to claim 16 further comprising:
displaying an operational status of the system using a plurality of indicators operated by the control system; and
providing a user interface suitable for displaying information from said control system, and receiving information entered by a therapist to control at least one operation of the system.

18. The method according to claim 17, further comprising a dynamic fall prevention mode.

19. The method according to claim 18, wherein the dynamic fall protection mode has an adjustable sensitivity level.

20. The method according to claim 16, wherein the database stores information relative to the operation of the system and where the user interface further displays information selected from the group consisting of: a patient record window; a day list window showing use of the system; a plan of care selection window; and a session data window.

21. The method according to claim 16, further comprising a boost mode, wherein when the system is operating to support a percentage of the body weight of a patient a temporary increase in the percentage body weight support is applied by the system.

* * * * *